(12) United States Patent
Gabriel et al.

(10) Patent No.: US 6,462,076 B2
(45) Date of Patent: Oct. 8, 2002

(54) BETA-AMINO ACID NITRILE DERIVATIVES AS CATHEPSIN K INHIBITORS

(75) Inventors: Tobias Gabriel, Loerrach; Michael Pech, Hartheim, both of (DE); Rosa Maria Rodriguez Sarmiento, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/872,927

(22) Filed: Jun. 1, 2001

(65) Prior Publication Data

US 2002/0016361 A1 Feb. 7, 2002

(30) Foreign Application Priority Data

Jun. 14, 2000 (EP) .................................................. 112577

(51) Int. Cl.[7] ......................... A61K 43/26; A61K 31/13; C07D 317/00; C07C 315/00
(52) U.S. Cl. ....................... 514/463; 558/430; 558/432; 549/469; 549/454; 514/465; 514/601; 514/613; 514/659
(58) Field of Search .................. 549/454, 469; 558/430, 432; 514/463, 465, 601, 613, 659

(56) References Cited

FOREIGN PATENT DOCUMENTS

| DE | 26 24 290 | 4/1977 |
|---|---|---|
| WO | WO 98/03540 | 1/1998 |
| WO | WO 99/24460 | 5/1999 |

OTHER PUBLICATIONS

Brömme, Drug News Perspect 1999, 12(2), 73–82.
Chapman et al., Annu. Rev. Phys. 1977, 59, 63–88.
Tezuka et al., J. Biol. Chem. 1994, 269, 1106–1109.
Lerner et al., J. Bone Min. Res. 1992, 7, 433–440.
Everts et al., J. Cell. Physiol. 1992, 150, 221–231.
Hummel et al., J. Rheumatol. 1998, 25(10) 1887–1894.
Sukhova et al., J. Clin. Invest. 1998, 102(3), 576–583.
Littlewood–Evans et al., Cancer Res. 1997, 57, 5386–5390.
Otto et al., Chem. Rev. 1997, 97, 133–171.
Thompson et al., Proc. Natl. Acad. Sci. USA 1997, 94, 14249–14254.
Maubach et al., Eur. J. Biochem. 1997, 250, 745–750.
Rink, Tetrahedron Lett. 1987, 28, 3787–3790.
Burgess et al., J. Am. Chem. Soc. 1968, 90, 4744–4745.
Kobayashi et al., Chem. Pharm. Bull. 1990, 38(2), 350–354.
Davies et al., J. Chem. Soc. Perkin Trans. 1994, 1, 1411–1415.

*Primary Examiner*—T. A. Solola
*Assistant Examiner*—Joseph Murray
(74) *Attorney, Agent, or Firm*—George W. Johnston; Dennis P. Tramaloni; F. Aaron Dubberley

(57) ABSTRACT

The present invention relates to beta-amino acid nitrile derivatives and pharmaceutically acceptable salts and/or pharmaceutically acceptable esters thereof. The compounds are cysteine protease inhibitors useful for the treatment of diseases associated with cysteine proteases, such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease.

294 Claims, No Drawings

BETA-AMINO ACID NITRILE DERIVATIVES AS CATHEPSIN K INHIBITORS

FIELD OF THE INVENTION

The present invention relates to novel beta-amino acid nitrile derivatives, their manufacture and use as medicaments. In particular, the invention relates to novel beta-amino acid nitrile derivatives of formula (I)

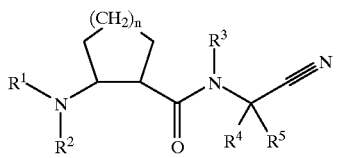

wherein $R^1$ represents hydrogen, aryl, —CO—$R^a$ or —$SO_2$—$R^b$, wherein
  $R^a$ represents lower-alkyl, lower-alkoxy, cycloalkyl, cycloalkyl-lower-alkyl, cycloalkyl-lower-alkoxy, cycloalkyloxy, aryl, aryloxy, aryl-lower-alkyl, aryl-lower-alkoxy, aryloxy-lower-alkyl, aryl-S-lower-alkyl, aryl-lower-alkenyl, heteroaryl, heteroaryl-lower-alkyl, or heteroaryl-lower-alkoxy,
  $R^b$ represents aryl, aryl-lower-alkyl, or heteroaryl $R^2$ represents hydrogen or lower-alkyl $R^3$ represents hydrogen or lower-alkyl $R^4$ represents hydrogen or lower-alkyl.

$R^5$ represents hydrogen, lower-alkyl, cycloalkyl, or aryl, n is 1 or 2, and pharmaceutically acceptable salts and/or pharmaceutically acceptable esters thereof.

BACKGROUND OF THE INVENTION

Cysteine proteases have been viewed as lysosomal mediators of terminal protein degradation. Several newly discovered members of this enzyme class, however, are regulated proteases with limited tissue expression, which implies specific roles in cellular physiology and thus would allow a specific targeting of these activities without interfering with the general lysosomal protein degragation. Development of inhibitors of specific cysteine proteases promises to provide new drugs for modifying immunity, osteoporosis, neurodegeneration, chronic inflammation, cancer and malaria (Brömme, *Drug News Perspect* 1999, 12(2), 73–82; Chapman et al., *Annu. Rev. Phys.* 1997, 59, 63–88).

Cysteine proteases can be grouped into two superfamilies: the family of enzymes related to interleukin $1_\beta$ converting enzyme (ICE), and the papain superfamily of cysteine proteases. Presently there are at least 12 human proteases of the papain family from which sequences have been obtained (cathepsin B, L, H, S, O, K, C, W, F, V(L2), Z(X) and bleomycin hydrolase). Cathepsin K was first discovered as a cDNA prominent in rabbit osteoclasts and referred to as OC-2 (Tezuka et al., *J. Biol. Chem.* 1994, 269, 1106–1109). Recent observations indicate that cathepsin K is the most potent mammalian elastase yet described. Cathepsin K, as well as cathepsins S and L, are also potent collagenases and gelatinases. Macrophages appear capable of mobilizing the active proteases within endosomal and/or lysosomal compartments to the cell surface under special circumstances. In this case, the cell surface/substrate interface becomes a compartment from which endogenous inhibitors are excluded and can be viewed as a physiological extension of the lysosome. This type of physiology is an innate trait of osteoclasts, a bone macrophage, and may also be exploited by other macrophages or cells in the context of inflammation. The abundance of cathepsin K in osteoclasts leads to the suggestion that cathepsin K plays an important role in bone resorption. Studies revealed that cathepsin K is the predominant cysteine protease in osteoclasts and is specifically expressed in human osteoclasts. A correlation between inhibition of cysteine protease activity and bone resorption has been reported (Lerner et al., *J. Bone Min. Res.* 1992, 7, 433; Everts et al., *J. Cell. Physiol.* 1992, 150, 221). Cathepsin K has been detected in synovial fibroblasts of RA patients, as well as in mouse hypertrophic chondrocytes (Hummel et al., *J. Rheumatol.* 1998, 25(10), 1887–1894). Both results indicate a direct role of cathepsin K in cartilage erosion. P. Libby (Sukhova et al., *J. Clin. Invest.* 1998, 102 (3), 576–583) reported that normal arteries contain little or no cathepsin K or S whereas macrophages in atheroma contained abundant immunoreactive cathepsins K and S. Most of the elastolytic activity of tissue extracts associated with human atheroma compared to non-atherosclerotic arteries could be inhibited with E64, a non-selective cysteine protease inhibitor.

Tumor progression and metastasis are characterized by the invasion of tumors into adjacent tissues as well as by the dissociation of cancer cells from primary tumors and the infiltration of metastatic cells into organs. These processes are associated with the degragation of extracellular matrix proteins and thus require proteolytic activity. Cathepsin K has been identified in primary breast tumors, as well as in breast tumor-derived bone metastasis (Littlewood-Evans et al., *Cancer Res.* 1997, 57, 5386–5390).

Different classes of compounds, such as aldehydes, α-ketocarbonyl compounds, halomethyl ketones, diazomethyl ketones, (acyloxy)methyl ketones, ketomethylsulfonium salts, epoxy succinyl compounds, vinyl sulfones, aminoketones, and hydrazides have been identified as cysteine protease inhibitors (Otto et al., *Chem. Rev.* 1997, 97, 133–171; Thompson et al., *Proc. Natl. Acad. Sci. USA* 1997, 94, 14249–14254). The shortcomings these compounds suffer from include lack of selectivity, poor solubility, rapid plasma clearance and cytotoxicity. A need therefore exists for novel inhibitors useful in treating diseases caused by pathological levels of proteases, especially cysteine proteases, including cathepsins, especially cathepsin K.

SUMMARY OF THE INVENTION

The beta-amino acid nitrile derivatives of formula (I) have an inhibitory activity on cysteine proteases, more paticulary on cysteine proteases of the papain superfamily, even more paticularly on cysteine proteases of the cathepsin family, most particularly on cathepsin K. It was surprisingly found, that this inhibiting effect on cathepsin K is selective with respect to other cathepsins. While compounds of formula (I) very efficiently inhibit cathepsin K, the inhibition of other protease inhibitors such as cathepsin S, cathepsin L and cathepsin B is much weaker. Therefore the new compounds of formula (I) are useful for specifically inhibiting cathepsin K. They can accordingly be used for the treatment of disorders which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fuigax, peripheral arterial occlusive disease, restenosis after angioplasty and stent placement, abdominal aortic aneurysm formation, inflammation, autoimmune disease, malaria, ocular fundus tissue cytopathy and respiratory disease. Accordingly, the present invention relates to a method for the prophylactic and/or therapeutic treatment of diseases which are associated with cystein proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease, which method comprises administering a compound of formula (I) to a human being or an animal. The present invention also relates to pharmaceutical compositions comprising a compound of formula (I) and a pharmaceutically acceptable carrier and/or adjuvant. Furthermore, the present invention relates to the use of such compounds for the preparation of medicaments for the treatment of disorders which are associated with cystein proteases. The present invention also relates to processes for the preparation of the compounds of formula (I).

DETAILED DESCRIPTION OF THE INVENTION

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "alkyl" refers to a branched or straight chain monovalent saturated aliphatic hydrocarbon radical of one to twenty carbon atoms, preferably one to sixteen carbon atoms. Alkyl groups can be substituted e.g. with halogen atoms.

The term "lower-alkyl" refers to a branched or straight chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "cycloalkyl" refers to a monovalent carbocyclic radical of 3 to 10 carbon atom(s), preferably 3 to 6 carbon atoms.

The term "halogen" refers to fluorine, chlorine, bromine and iodine, with fluorine, chlorine and bromine being preferred and chlorine and bromine being more preferred.

The term "alkoxy" refers to the group R'—O—, wherein R' is an alkyl The term "lower-alkoxy" refers to the group R'—O—, wherein R' is a lower-alkyl.

The term "alkenyl" stands for alone or in combination with other groups, a straight-chain or branched hydrocarbon residue containing an olefinic bond and up to 20, preferably up to 16 C-atoms. The term "lower-alkenyl" refers to a straight-chain or branched hydrocarbon residue containing an olefinic bond and up to 7, preferably up to 4 C-atoms.

The term "aryl" relates to the phenyl or naphthyl group which can optionally be mono-or multiply-substituted by alkyl, halogen, hydroxy, nitro, cyano, —CF₃, acetyl, acetylamino, —SCH₃, alkoxy, alkylcarbonyloxy, aryl, aryloxy, or aryl-alkoxy. Preferred substituents are lower-alkyl, fluorine, chlorine, bromine, hydroxy, lower-alkoxy, lower-alkylcarbonyloxy, phenyl, phenoxy, aryl-lower-alkyl, and aryl-lower-alkoxy. More preferred substituents are hydroxy, methyl, chlorine, bromine, and methoxy. The term aryl further relates to a substituted phenyl group which is the benzo[1,3]dioxol-5-yl group.

The term "heteroaryl" refers to an aromatic 5- or 6-membered ring which can contain 1, 2 or 3 atoms selected from nitrogen, oxygen or sulphur such as furyl, pyridyl, 1,2-, 1,3- and 1,4-diazinyl, thienyl, isoxazolyl, oxazolyl, imidazolyl, pyrrolyl, with furyl and thienyl being preferred. The term "heteroaryl" further refers to bicyclic aromatic groups comprising 2 5- or 6-membered rings, in which one or both rings can contain 1, 2 or 3 atoms selected from nitrogen, oxygen or sulphur such as e,g, benzo[1,2,5] oxadiazole or benzofuranyl. A heteroaryl group may have a substitution pattern as described earlier in connection with the term "aryl".

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

The term "pharmaceutically acceptable esters" embraces esters of the compounds of formula (1), in which hydroxy groups have been converted to the corresponding esters with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

The term "isolated sterioisomer" refers to a compound substantially free of isomers having different conformations at any chiral centers having a specified conformation in the compound's formula or name.

The term "therapeutically effective amount" refers to that amount of a compound which, when administered to a patient having a cysteine protease associated condition, ameliorates or relieves one or more symptoms of that condition.

In detail, the present invention refers to compounds of formula (I)

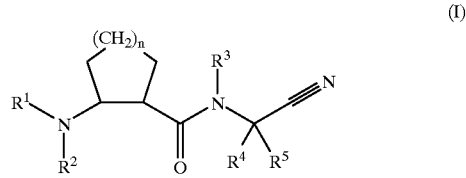

wherein
  $R^1$ represents hydrogen, aryl, —CO—$R^a$ or —SO₂—$R^b$, wherein
    $R^a$ represents lower-alkyl, lower-alkoxy, cycloalkyl, cycloalkyl-lower-alkyl, cycloalkyl-lower-alkoxy, cycloalkyloxy, aryl, aryloxy, aryl-lower-alkyl, aryl-lower-alkoxy, aryloxy-lower-alkyl, aryl-S-lower-alkyl, aryl-lower-alkenyl, heteroaryl, heteroaryl-lower-alkyl, or heteroaryl-lower-alkoxy,
    $R^b$ represents aryl, aryl-lower-alkyl, or heteroaryl
  $R^2$ represents hydrogen or lower-alkyl
  $R^3$ represents hydrogen or lower-alkyl
  $R^4$ represents hydrogen or lower-alkyl.

$R^5$ represents hydrogen, lower-alkyl, cycloalkyl, or aryl,
n is 1 or 2,
and pharmaceutically acceptable salts and/or pharmaceutically acceptable esters thereof.

The compounds of formula (I) have at least 2 asymmetric carbon atoms and can exist in the form of optically pure enantiomers or as racemates. The invention embraces all of these forms. Preferred compounds of formula (I) are compounds of formula (Ia)

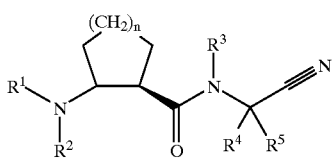

(Ia)

wherein $R^1$, $R^2$, $R^3$, $R^4$, $R^5$ and n have the significances given above and pharmaceutically acceptable salts and/or pharmaceutically acceptable esters thereof The compounds of formula (Ia) encompass cis- as well as trans-compounds. Other preferred compounds of formula (I) are cis-compounds of formula (Ib)

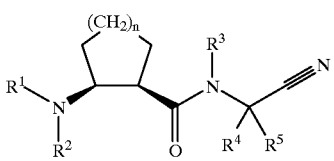

(Ib)

wherein $R^1$, $R^2$, $R^3$, $R^4$, $R^5$ and n have the significances given above and pharmaceutically acceptable salts and/or pharmaceutically acceptable esters thereof Further preferred compounds of formula (I) are compounds of formula (Ic)

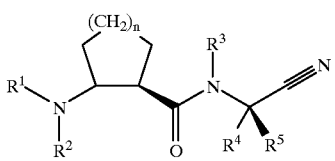

(Ic)

wherein $R^1$, $R^2$, $R^3$, $R^4$, $R^5$ and n have the significances given above and pharmaceutically acceptable salts and/or pharmaceutically acceptable esters thereof. The compounds of formula (Ic) encompasses cis- as well as trans-compounds.

Compounds of formula (I) in which n is 2 are preferred. Compounds of formula (I) in which $R^2$, $R^3$, and/or $R^4$ represent hydrogen are also preferred. Another preferred embodiment refers to compounds of formula (I) in which $R^5$ is aryl, particularly those compounds in which $R^5$ is phenyl or naphthyl, optionally substituted with lower-alkyl, halogen, hydroxy, lower-alkoxy, or lower-alkyl-carbonyloxy, or in which $R^5$ is benzo[1,3] dioxyl. Further, compounds of formula (I) in which $R^5$ represents phenyl or naphthyl, optionally substituted with hydroxy, methoxy, methyl, acetoxy, chlorine or bromine, or wherein $R^5$ is benzo[1,3] dioxyl are also preferred with phenyl, 3-hydroxy-phenyl, 3-methoxy-phenyl, 4-methoxy-phenyl, 3-methyl-phenyl, 2,4-dimethoxy-phenyl, 3,4-dimethoxy-phenyl, 3-chloro-phenyl, 3-bromo-phenyl, 4-bromo-phenyl, or benzo[1,3] dioxol-5-yl being especially preferred. Other preferred compounds of formula (I) are those wherein $R^5$ is hydrogen. Further preferred compounds of formula (I) are those wherein $R^5$ is cycloalkyl, more preferably cyclopropyl.

Compounds of formula (I) in which $R^1$ represents —CO—$R^a$ and $R^a$ is as defined above are preferred. Compounds of formula (I) in which $R^1$ represents —CO—$R^a$ and $R^a$ is cycloalkyl, cycloalkly-lower-alkyl, cycloalkyloxy, aryl, aryloxy, aryl-lower-alkyl, aryl-lower-alkoxy, aryloxy-lower-alkyl, aryl-S-lower-alklyl, aryl-lower-alkenyl, or heteroaryl-lower-alkoxy are especially preferred. A further preferred embodiment are compounds of formula (I) in which $R^1$ represents —CO—$R^a$ and $R^a$ is phenyl, optionally substituted with phenyl, cyano, and/or fluoro, or $R^a$ is benzyloxy optionally substituted with methyl, chloro, fluoro, methoxy, nitro, and/or $CF_3$, or $R^a$ is phenylvinylene, thiophenyl-methylene-oxy, cyclopentyloxy, thiophenyl-ethylene-oxy, naphthyloxy, thiophenyl-trimethylene-oxy, or phenoxy. Particularly preferred are compounds of formula (I) wherein $R^1$ represents—CO—$R^a$ and $R^a$ is benzyloxy, phenylvinylene, thiophen-2-yl-methylene-oxy, or thiophen-3-yl-methylene-oxy. Another preferred embodiment relates to compounds of formula (I) wherein $R^1$ represents —$SO_2$— $R^b$ and $R^b$ is as defined above. Preferrably $R^b$ represents phenyl optionally substituted with chlorine, cyano and/or methylcarbonyl-amino, or $R^b$ is benzyl or benzo[1,2,5] oxadiazole. Most preferrably, $R^b$ represents 4-chloro-phenyl. A further preferred embodiment relates to compounds of formula (I) wherein $R^1$ represents phenyl optionally substituted with ethoxy. Other preferred compounds of formula (I) are those wherein $R^1$ represents —CO—$R^a$ and $R^a$ is benzyl optionally substituted with chloro, or phenyl optionally substituted with lower-alkyl, lower-alkoxy, or cyano, preferably those wherein $R^a$ is 4-ethyl-phenyl, 4-methoxy-phenyl, 4-ethoxy-phenyl, 4-cyano-phenyl, 4-tert.-butyl-phenyl, or 4-chloro-benzyl. Further preferred compounds of the present invention are those wherein $R^1$ represents —CO—$R^a$ and $R^a$ is heteroaryl, preferably those in which $R^a$ is 5-methoxy-benzofuran-2-yl.

Preferred compounds of formula (I) are those selected from the group consisting of
(1R,2R)-(2-{(S)-[Cyano-(3-hydroxy-phenyl)-methyl]-carbamoyl}-cyclohexyl)-carbamic acid benzyl ester,
cis-2-(3-Phenyl-acryloylamino)-cyclohexanecarboxylic acid [(R)- and (S)-cyano-(3,4-dimethoxy-phenyl)-methyl]-amide,
(R)-{2-[(S)-(Cyano-phenyl-methyl)-(R)-carbamoyl]-cyclohexyl}-carbamic acid benzyl ester,
syn-{2-[(S)-(Cyano-phenyl-methyl)-carbamoyl]-cyclohexyl}-carbamic acid benzyl ester,
cis-(2-{(R)- and (S)-[Cyano-(2,4-dimethoxy-phenyl)-methyl]-carbamoyl}-cyclohexyl)-carbamic acid benzyl ester,
trans-2-(4-Chloro-benzenesulfonylamino)-cyclohexanecarboxylic acid [cyano-(3-hydroxy-phenyl)-methyl]-amide,
trans-{2-[(Benzo[1,3]dioxol-5-yl-cyano-methyl)-carbamoyl]-cyclohexyl}-carbamic acid benzyl ester,
cis-(2-{[Cyano-(3-hydroxy-phenyl)-methyl]-carbamoyl}-cyclohexyl)-carbamic acid benzyl ester,
trans-(2-{[Cyano-(3-hydroxy-phenyl)-methyl]-carbamoyl}-cyclohexyl)-carbamic acid benzyl ester,
cis-2-(3-Phenyl-acryloylamino-cyclohexanecarboxylic acid ((R)- and (S)-cyano-phenyl-methyl-amide,
(2-{[Cyano- (3,4-dimethoxy-phenyl)-methyl]-carbamoyl}-cyclohexyl)-carbamic acid benzyl ester (1cis-racemate), cis-{2-[(R)- and (S)-(Cyano-m-tolyl-methyl)-carbamoyl]-cyclohexyl}-carbamic acid benzyl ester,
(2-{[Cyano-(3-hydroxy-phenyl)-methyl]-carbamoyl}-cyclohexyl)-carbamic acid thiophen-3-ylmethyl ester,
cis-(2-{(R)- and (S)-[Cyano-(4-methoxy-phenyl)-methyl]-carbamoyl}-cyclohexyl)-carbamic acid benzyl ester,
cis-(2-{(R)- and (S)-[Cyano-(3-methoxy-phenyl)-methyl]-carbamoyl}-cyclohexyl)-carbamic acid benzyl ester,
trans-(2-{[Cyano-(3-hydroxy-phenyl)-methyl]-carbamoyl}-cyclohexyl)-carbamic acid thiophen-2-ylmethyl ester,
cis-(2-{(R)- and (S)-[(3-Chloro-phenyl)-cyano-methyl]-carbamoyl}-cyclohexyl)-carbamic acid benzyl ester,
cis-{2-[(Cyano-phenyl-methyl)-carbamoyl]-cyclohexyl}-carbamic acid benzyl ester,
trans-(2-{[(3-Bromo-phenyl)-cyano-methyl]-carbamoyl}-cyclohexyl)-carbamic acid benzyl ester,
cis-(2-{(R)- and (S)-[(4-Bromo-phenyl)-cyano-methyl]-carbamoyl}-cyclohexyl)-carbamic acid benzyl ester,
cis-(2-{[(R)- and (S)-Cyano-(3,4-dimethoxy-phenyl)-methyl]-carbamoyl}-cyclohexyl)-carbamic acid cyclopentyl ester,
trans-(2-{[Cyano-(3-hydroxy-phenyl)-methyl]-carbamoyl}-cyclohexyl)-carbamic acid 2-thiophen-2-yl-ethyl ester,
trans-(2-{[Cyano-(3-hydroxy-phenyl)-methyl]-carbamoyl}-cyclohexyl)-carbamic acid 2-methyl-benzyl ester,
trans-2-Phenylmethanesulfonylamino-cyclohexanecarboxylic acid [cyano-(3-hydroxy-phenyl)-methyl]-amide,
trans-(2-{[Cyano-(3-hydroxy-phenyl)-methyl]-carbamoyl}-cyclohexyl)-carbamic acid 2-chloro-benzyl ester,
cis-(2-{(R)- and (S)-[(4-Chloro-phenyl)-cyano-methyl]-carbamoyl}-cyclohexyl)-carbamic acid benzyl ester,
(2-{[Cyano-(3-hydroxy-phenyl)-methyl]-carbamoyl}-cyclohexyl)-carbamic acid 4-fluoro-benzyl ester,
cis-{2-[(R)- and (S)-(Cyano-phenyl-methyl-carbamoyl]-cyclohexyl}-carbamic acid naphthalene-2-yl ester,
cis-{2-[(R)- and (S)-(Cyano-naphthalene-2-yl-methyl)-carbamoyl]-cyclohexyl}-carbamic acid benzyl ester,
trans-(2-{[Cyano-(3-hydroxy-phenyl)-methyl]-carbamoyl}-cyclohexyl)-carbamic acid 3-thiophen-2-yl-propyl ester,
trans-2-(4-Cyano-benzenesulfonylamino)-cyclohexanecarboxylic acid [cyano-(3-hydroxy-phenyl)-methyl]-amide,
trans-(2-{[(3-Bromo-phenyl)-cyano-methyl]3-carbamoyl}-cyclohexyl)-carbamic acid benzyl ester,
cis-Acetic acid 4-(R)- and (S)-[(2-benzyloxycarbonylamino-cyclohexanecarbonyl)-amino]-cyano-methyl}-phenyl ester,
trans-{2-[(Cyano-phenyl-methyl)-carbamoyl]-cyclohexyl}-carbamic acid benzyl ester,
cis-N-(2-{[(R)- and (S)-Cyano-(3,4-dimethoxy-phenyl)-methyl]-carbamoyl}-cyclohexyl)-benzamide,
trans-(2-{[(3-Bromo-4-methoxy-phenyl)-cyano-methyl]-carbamoyl}-cyclohexyl)-carbamic acid benzyl ester,
cis-{2-[(R)- and (S)-(Cyano-naphthalene-1-yl-methyl)-carbamoyl]-cyclohexyl}-carbamic acid benzyl ester,
trans-(2-{[Cyano-(3-hydroxy-phenyl)-methyl]-carbamoyl}-cyclohexyl)-carbamic acid 2-methoxy-benzyl ester,
(1R,2R)-(2-{(R)-[Cyano-(3-hydroxy-phenyl)-methyl]-carbamoyl}-cyclohexyl)-carbamic acid benzyl ester,
trans-(2-{[(3-Bromo-4-methoxy-phenyl)-cyano-methyl]-carbamoyl}-cyclohexyl)-carbamic acid benzyl ester,
trans-[2-(Cyanomethyl-carbamoyl)-cyclohexyl]-carbamic acid benzyl ester,
trans-(2-{[Cyano-(3-hydroxy-phenyl)-methyl]-carbamoyl}-cyclohexyl)-carbamic acid 3-chloro-benzyl ester,
trans-(2-{[Cyano-(3-hydroxy-phenyl)-methyl]-carbamoyl}-cyclohexyl)-carbamic acid 3-methyl-benzyl ester,
cis-Biphenyl-4-carboxylic acid (2-{[(R)- and (S)-cyano-(3,4-dimethoxy-phenyl)-methyl]-carbamoyl}-cyclohexyl)-amide,
cis-{2-[(R)- and (S)-(Cyano-phenyl-methyl-carbamoyl]-cyclohexyl}-carbamic acid phenyl ester,
trans-2-(4-Acetylamino-benzenesulfonylamino)-cyclohexanecarboxylic acid [cyano-(3-hydroxy-phenyl)-methyl]-amide,
cis-N-{2-[(R)- and (S)-(Cyano-phenyl-methyl-carbamoyl]-cyclohexyl}-benzamide,
trans-2-{[Cyano-(3-hydroxy-phenyl)-methyl]-carbamoyl}-cyclohexyl)-carbamic acid 3-methoxy-benzyl ester,
trans-(2-{[Cyano-(3-hydroxy-phenyl)-methyl]-carbamoyl}-cyclohexyl)-carbamic acid 4-methyl-benzyl ester,
cis-{2-[(Benzo[1,3]dioxol-5-yl-cyano-methyl)-carbamoyl]-cyclohexyl}-carbamic acid benzyl ester,
trans-4-Cyano-N-(2-{[cyano-(3-hydroxy-phenyl)-methyl]-carbamoyl}-cyclohexyl)-benzamide,
trans-(2-{[Cyano-(3-hydroxy-phenyl)-methyl]-carbamoyl}-cyclohexyl)-carbamic acid 4-methoxy-benzyl ester,
cis-2-(3-Cyclopentyl-propionylamino)-cyclohexanecarboxylic acid [(R)- and (S)-cyano-(3,4-dimethoxy-phenyl)-methyl]-amide,
(2-{[Cyano-(3,4-dimethoxy-phenyl)-methyl]-carbamoyl}-cyclohexyl)-carbamic acid benzyl ester (1cis-racemate),
cis-{2-[(R)- and (S)-(Cyano-phenyl-methyl-carbamoyl]-cyclohexyl}-carbamic acid 4-nitro-benzyl ester,
cis-(2-{[(R)- and (S)-Cyano-(3,4-dimethoxy-phenyl)-methyl]-carbamoyl}-cyclohexyl)-carbamic acid 4-nitro-benzyl ester,
cis-2-(3-Phenyl-propionylamino)-cyclohexanecarboxylic acid [(R)- and (S)-cyano-(3,4-dimethoxy-phenyl)-methyl]-amide,
cis-2-(Cyclopropanecarbonyl-amino)-cyclohexanecarboxylic acid [(R)- and (S)-cyano-(3,4-dimethoxy-phenyl)-methyl]-amide,
cis-{2-[(R)- and (S)-(Cyano-phenyl-methyl-carbamoyl]-cyclohexyl}-carbamic acid cyclopentyl ester,
trans-(2-{[Cyano-(3-hydroxy-phenyl)-methyl]-carbamoyl}-cyclohexyl)-carbamic acid 3-p-tolyl-propyl ester,
cis-[2-((R)- and (S)-1-Cyano-3-methyl-butylcarbamoyl)-cyclohexyl]-carbamic acid benzyl ester,
cis-2-(2-Phenoxy-acetylamino)-cyclohexanecarboxylic acid [(R)- and (S)-cyano-(3,4-dimethoxy-phenyl)-methyl]-amide,
trans-2-(2-Phenoxy-acetylamino)-cyclohexanecarboxylic acid [cyano-(3-hydroxy-phenyl)-methyl]-amide,
cis-(2-{(R)- and (S)-[Cyano-(2,4-dimethyl-phenyl)-methyl]-carbamoyl}-cyclohexyl)-carbamic acid benzyl ester,
cis-2-[2-(4-Chloro-phenoxy)-acetylamino]-cyclohexanecarboxylic acid [(R)- and (S)-cyano-(3,4-dimethoxy-phenyl)-methyl]-amide,
cis-2-(2-Phenylsulfanyl-acetylamino)-cyclohexanecarboxylic acid ((R)- and (S)-cyano-phenyl-methyl-amide,
trans-(2-{[Cyano-(3-hydroxy-phenyl)-methyl]-carbamoyl}-cyclohexyl)-carbamic acid 3-(4-chloro-phenyl)-propyl ester,
cis-2-(2-Phenylsulfanyl-acetylamino)-cyclohexanecarboxylic acid [(R)- and (S)-cyano-(3,4-dimethoxy-phenyl)-methyl]-amide,
trans-2-(Benzo[1,2,5]oxadiazole-4-sulfonylamino)-cyclohexanecarboxylic acid [cyano-(3-hydroxy-phenyl)-methyl]-amide,
trans-N-(2-{[Cyano-(3-hydroxy-phenyl)-methyl]-carbamoyl}-cyclohexyl)-4-fluoro-benzamide, cis-2-[2-(4-Chloro-phenoxy-acetylamino]-
cyclohexanecarboxylic acid ((R)- and (S)-cyano-phenyl-methyl-amide,
cis-2-(3-Phenyl-propionylamino)-cyclohexanecarboxylic acid (cyano-phenyl-methyl)-amide,
cis-2-Phenylacetylamino-cyclohexanecarboxylic acid [(R)- and (S)-cyano-(3,4-dimethoxy-phenyl)-methyl]-amide,
cis-2-Phenylmethanesulfonylamino-cyclohexanecarboxylic acid [(R)- and (S)-cyano-(3,4-dimethoxy-phenyl)-methyl]-amide,
trans-2-(2-Phenylsulfanyl-acetylamino)-cyclohexanecarboxylic acid [cyano-(3-hydroxy-phenyl)-methyl]-amide,
cis-[2-((R)- and (S)-1-Cyano-hexylcarbamoyl)-cyclohexyl]-carbamic acid benzyl ester
cis-2-(2-Phenoxy-acetylamino-cyclohexanecarboxylic acid ((R)- and (S)-cyano-phenyl-methyl-amide,
trans-Isoxazole-5-carboxylic acid (2-{[cyano-(3-hydroxy-phenyl)-methyl]-carbamoyl}-cyclohexyl)-amide,
cis-2-(3-Cyclohexylcarbonylamino)-cyclohexanecarboxylic acid [(R)- and (S)-cyano-(3,4-dimethoxy-phenyl)-methyl3-amide,
(2-{[Cyano-(3-hydroxy-phenyl)-methyl]-carbamoyl}-cyclohexyl)-carbamic acid 4-trifluoromethyl-benzyl ester,
cis-2-(Cydobutanecarbonyl-amino)-cyclohexanecarboxylic acid [(R)- and (S)-cyano-(3,4-dimethoxy-phenyl)-methyl]-amide,
cis-2-[2-(4-Chloro-phenyl-acetylamino]-cyclohexanecarboxylic acid ((R)- and (S)-cyano-phenyl-methyl-amide,
cis-2-(Cyclopentanecarbonyl-amino-cyclohexanecarboxylic acid ((R)- and (S)-cyano-phenyl-methyl-amide,
cis-2-[2-(4-Chloro-phenyl)-acetylamino]-cyclohexanecarboxylic acid [(R)- and (S)-cyano-(3,4-dimethoxy-phenyl)-methyl]-amide,
(1S,2R)-{2-(R)- and (S)-[(Cyano-phenyl-methyl)-carbamoyl]-cyclohexyl}-carbamic acid benzyl ester,
(1S,2R)-(2-(R)- and (S)-{[Cyano-(3-methoxy-phenyl)-methyl]-carbamoyl}-cyclohexyl)-carbamic acid benzyl ester,
trans-N-(2-{[Cyano-(3-hydroxy-phenyl)-methyl-carbamoyl}-cyclohexyl)-4-fluoro-benzamide,
cis-2-(2-Benzyloxy-acetylamino)-cyclohexanecarboxylic acid [(R)- and (S)-cyano-(3,4-dimethoxy-phenyl)-methyl]-amide,
trans-2-(2-Thiophen-2-yl-acetylamino)-cyclohexanecarboxylic acid [cyano-(3-hydroxy-phenyl)-methyl]-amide,
cis-[2-((R)- and (S)-1-Cyano-propylcarbamoyl)-cyclohexyl]-carbamic acid benzyl ester,
cis-2-Phenylacetylamino-cyclohexanecarboxylic acid ((R)- and (S)-cyano-phenyl-methyl-amide,
cis-2-(2-Benzyloxy-acetylamino)-cyclohexanecarboxylic acid ((R)- and (S)-cyano-phenyl-methyl-amide,
cis-2-(Cyclopropanecarbonyl-amino-cyclohexanecarboxylic acid ((R)- and (S)-cyano-phenyl-methyl-amide,
cis-2-(3-Cyclopentyl-propionylamino-cyclohexanecarboxylic acid ((R)- and (S)-cyano-phenyl-methyl-amide,
cis-2-(Cyclopentanecarbonyl-amino)-cyclohexanecarboxylic acid [(R)- and (S)-cyano-(3,4-dimethoxy-phenyl)-methyl]-amide,
trans-Thiophene-2-carboxylic acid (2-{[cyano-(3-hydroxy-phenyl)-methyl]-carbamoyl}-cyclohexyl)-amide,
cis-2-(3-Phenyl-propionylamino)-cyclohexanecarboxylic acid ((R)- and (S)-cyano-phenyl-methyl-amide,
cis-2-Phenylmethanesulfonylamino-cyclohexanecarboxylic acid ((R)- and (S)-cyano-phenyl-methyl-amide,
trans-(2-{[Cyano-(3-methoxy-phenyl)-methyl]-carbamoyl}-cyclohexyl)-carbamic acid benzyl ester,
cis-2-(4-Ethoxy-phenylamino)-cyclohexanecarboxylic acid [cyano-(3-hydroxy-phenyl)-methyl]-amide,
2-(4-Ethoxy-phenylamino)-cyclohexanecarboxylic acid (cyano-phenyl-methyl)-amide,
cis-2- (4-Ethoxy-phenylamino)-cyclohexanecarboxylic acid [(3-bromo-phenyl)-cyano-methyl]-amide,
cis-2-(4-Ethoxy-phenylamino)-cyclohexanecarboxylic acid (benzo[1,3]dioxol-5-yl-cyano-methyl)-amide,
cis-2-(4-Ethoxy-phenylamino)-cyclohexanecarboxylic acid [cyano-(4-methoxy-phenyl)-methyl]-amide,
cis-2-Phenylamino-cyclohexanecarboxylic acid (benzo[1,3]dioxol-5-yl-cyano-methyl)-amide,
2-Phenylamino-cyclohexanecarboxylic acid (cyano-phenyl-methyl)-amide,
cis-(2-{(R)- and (S)-[Cyano-(3,4-dimethoxy-phenyl)-methyl]-carbamoyl}-cyclopentyl)-carbamic acid benzyl ester,
trans-(2-{[(3-Chloro-phenyl-cyano-methyl]-carbamoyl-cyclopentyl-carbamic acid benzyl ester,
trans-(2-{[Cyano-(3-methoxy-phenyl-methyl]-carbamoyl}-cyclopentyl-carbamic acid benzyl ester,
trans-{2-[(Cyano-phenyl-methyl-carbamoyl]-cyclopentyl}-carbamic acid benzyl ester, and
trans-{2-[(Cyano-m-tolyl-methyl-carbamoyl]-cyclopentyl}-carbamic acid benzyl ester, and pharmaceutically acceptable salts and/or pharmaceutically acceptable esters thereof.

Especially preferred compounds of formula (I) are
(1R,2R)-(2-{(S)-[Cyano-(3-hydroxy-phenyl)-methyl]-carbamoyl}-cyclohexyl)-carbamic acid benzyl ester,
cis-2-(3-Phenyl-acryloylamino)-cyclohexanecarboxylic acid [(R)- and (S)-cyano-(3,4-dimethoxy-phenyl)-methyl]-amide,
(R)-{2-[(S)-(Cyano-phenyl-methyl)-(R)-carbamoyl]-cyclohexyl}-carbamic acid benzyl ester,
syn-{2-[(S)-(Cyano-phenyl-methyl)-carbamoyl]-cyclohexyl}-carbamic acid benzyl ester,
cis-(2-{(R)- and (S)-[Cyano-(2,4-dimethoxy-phenyl)-methyl]-carbamoyl}-cyclohexyl)-carbamic acid benzyl ester,
trans-2-(4-Chloro-benzenesulfonylamino)-cyclohexanecarboxylic acid [cyano-(3-hydroxy-phenyl)-methyl]-amide,
trans-{2-[(Benzo[1,3]dioxol-5-yl-cyano-methyl)-carbamoyl]-cyclohexyl}-carbamic acid benzyl ester,
cis-(2-{[Cyano-(3-hydroxy-phenyl)-methyl]-carbamoyl}-cyclohexyl)-carbamic acid benzyl ester,
trans-(2-{[Cyano-(3-hydroxy-phenyl)-methyl]-carbamoyl}-cyclohexyl)-carbamic acid benzyl ester,
cis-2-(3-Phenyl-acryloylamino)-cyclohexanecarboxylic acid ((R)- and (S)-cyano-phenyl-methyl-amide,
(2-{[Cyano-(3,4-dimethoxy-phenyl)-methyl]-carbamoyl}-cyclohexyl)-carbamic acid benzyl ester (1cis-racemate),
cis-{2-[(R)- and (S)-(Cyano-m-tolyl-methyl]-carbamoyl]-cyclohexyl}-carbamic acid benzyl ester,
(2-{[Cyano-(3-hydroxy-phenyl)-methyl]-carbamoyl}-cyclohexyl)-carbamic acid thiophen-3-ylmethyl ester,
cis-(2-{(R)- and (S)-[Cyano-(4-methoxy-phenyl)-methyl]-carbamoyl}-cyclohexyl)-carbamic acid benzyl ester,
cis-(2-{(R)- and (S)-[Cyano-(3-methoxy-phenyl)-methyl]-carbamoyl}-cyclohexyl)-carbamic acid benzyl ester,
trans-(2-{[Cyano-(3-hydroxy-phenyl)-methyl]-carbamoyl}-cyclohexyl)-carbamic acid thiophen-2-ylmethyl ester, cis-(2-{(R)- and (S)-[(3-Chloro-phenyl)-cyano-methyl]-carbamoyl}-cyclohexyl)-carbamic acid benzyl ester,
cis-{2-[(Cyano-phenyl-methyl)-carbamoyl]-cyclohexyl}-carbamic acid benzyl ester,
trans-(2-1{[(3-Bromo-phenyl)-cyano-methyl]-carbamoyl}-cyclohexyl)-carbamic acid benzyl ester,
cis-(2-{(R)- and (S)-[(4-Bromo-phenyl)-cyano-methyl]-carbamoyl}-cyclohexyl)-carbamic acid benzyl ester, and
cis-(2-{(R)- and (S)-[Cyano-(3,4-dimethoxy-phenyl)-methyl]-carbamoyl}-cyclopentyl)-carbamic acid benzyl ester,
and pharmaceutically acceptable esters thereof.

Other preferred compounds of formula (I) are those selected from the group consisting of
Cis{2-[(Cyano-cyclopropyl-methyl)-carbamoyl]-cyclohexyl}-carbamic acid benzyl ester,
Cis-[2-(Cyanomethyl-carbamoyl)-cyclohexyl]-carbamic acid 2-chloro-benzyl ester,
Cis-[2-(Cyanomethyl-carbamoyl)-cyclohexyl]-carbamic acid 2-bromo-benzyl ester,
Cis-[2-(Cyanomethyl-carbamoyl)-cyclohexyl]-carbamic acid 3-nitro-benzyl ester,
Cis-[4-(Cyanomethyl-carbamoyl)-cyclohexyl]-carbamic acid 4-chloro-benzyl ester,
Cis-[4-(Cyanomethyl-carbamoyl)-cyclohexyl]-carbamic acid 3,4-dichloro-benzyl ester,
Cis-[4-(Cyanomethyl-carbamoyl)-cyclohexyl]-carbamic acid 3-chloro-benzyl ester,
Trans-[4-(Cyanomethyl-carbamoyl)-cyclohexyl]-carbamic acid 2-chloro-benzyl ester,
Trans-[4-(Cyanomethyl-carbamoyl)-cyclohexyl]-carbamic acid 2-bromo-benzyl ester,
Trans-[4-(Cyanomethyl-carbamoyl)-cyclohexyl]-carbamic acid 3-nitro-benzyl ester,
Trans-[4-(Cyanomethyl-carbamoyl)-cyclohexyl]-carbamic acid phenyl ester,
Trans-[4-(Cyanomethyl-carbamoyl)-cyclohexyl]-carbamic acid 3,4-dichloro-benzyl ester,
Cis-5-Methoxy-benzofuran-2-carboxylic acid 12-(cyanomethyl-carbamoyl)-cyclohexyl]-amide,
Trans-5-Methoxy-benzofuran-2-carboxylic acid [2-(cyanomethyl-carbamoyl)-cyclohexyl]-amide,
Trans-N-[2-(Cyanomethyl-carbamoyl)-cyclohexyl]-2-chloro-4-fluoro-benzamide,
Trans-N-[2-(Cyanomethyl-carbamoyl)-cyclohexyl]-2-methoxy-3-methyl-benzamide,
Trans-N-[2-(Cyanomethyl-carbamoyl)-cyclohexyl]-2,6-dichloro-4-methoxy-benzamide,
Cis-N-[2-(Cyanomethyl-carbamoyl)-cyclohexyl]-3-fluoro-4-methyl-benzamide,
Cis-N-[2-(Cyanomethyl-carbamoyl)-cyclohexyl]-3-chloro-4-methyl-benzamide,
Trans-N-[2-(Cyanomethyl-carbamoyl)-cyclohexyl]-3-bromo-4-methyl-benzamide,
Trans-N-[2-(Cyanomethyl-carbamoyl)-cyclohexyl]-4-cyanomethyl-benzamide,
Cis-N-[2-(Cyanomethyl-carbamoyl)-cyclohexyl]-3,5-di-trifluoromethyl-benzamide,
Cis-N-[2-(Cyanomethyl-carbamoyl)-cyclohexyl]-4-tert-butyl-benzamide,
Cis-N-[2-(Cyanomethyl-carbamoyl)-cyclohexyl]-3-chloro-6-methoxy-benzamide,
Trans-N-[2-(Cyanomethyl-carbamoyl)-cyclohexyl]-3-chloro-6-methoxy-benzamide,
Cis-N-[2-(Cyanomethyl-carbamoyl)-cyclohexyl]-3-chloro-benzamide,
Cis-N-[2-(Cyanomethyl-carbamoyl)-cyclohexyl]-3-acetylamino-benzamide,
Trans-N-(2-(Cyanomethyl-carbamoyl)-cyclohexyl]-3-acetylamino-benzamide,
Cis-N-[2-(Cyanomethyl-carbamoyl)-cyclohexyl]-4-acetylamino-benzamide,
Trans-N-[2-(Cyanomethyl-carbamoyl)-cyclohexyl]-4-acetylamino-benzamide,
Cis-N-[2-(Cyanomethyl-carbamoyl)-cyclohexyl]-4-acetyl-benzamide,
Trans-N-[2-(Cyanomethyl-carbamoyl)-cyclohexyl]-4-acetyl-benzamide,
Cis-N-[2-(Cyanomethyl-carbamoyl)-cyclohexyl]-2-chloro-5-(methylthio)-benzamide,
Cis-N-[2-(Cyanomethyl-carbamoyl)-cyclohexyl]-2,3-dichloro-benzamide,
Trans-N-[2-(Cyanomethyl-carbamoyl)-cyclohexyl]-2,3-dichloro-benzamide,
Cis-N-[2-(Cyanoethyl-carbamoyl)-cyclohexyl]-2,4-dichloro-benzamide,
Cis-N-[2-(Cyanomethyl-carbamoyl)-cyclohexyl]-2,5-dichloro-benzamide,
Cis-N-[2-(Cyanomethyl-carbamoyl)-cyclohexyl]-2,6-dichloro-benzamide,
Cis-N-[2-(Cyanomethyl-carbamoyl)-cyclohexyl]-3,4-dichloro-benzamide,
Trans-N-[2-(Cyanomethyl-carbamoyl)-cyclohexyl]-3,4-dichloro-benzamide,
Cis-N-[2-(Cyanomethyl-carbamoyl)-cyclohexyl]-3,4-dichloro-benzamide,
Trans-N-[2- (Cyanomethyl-carbamoyl)-cyclohexyl]-3,5-dichloro-benzamide,
Cis-2-{[(4-chlophenyl)acetyl}amino]-N-[cyano(cyclopropyl)methyl]cyclo-hexanecarboxamide,
Cis-N-[cyano(cyclopropyl)methyl]-2-{[3-(3-methoxyphenyl)propanoyl]amino}cyclohexanecarboxamide,
Cis-N-[2-({[cyano(cyclopropyl)methyl]amino}carbonyl)cyclohexyl]-4-ethylbenzamide,
Cis-N-[2-({[cyano(cyclopropyl)metbyl]amino}carbonyl)cyclohexyl]-4-ethoxybenzamide,
Cis-N-[2-({[cyano(cyclopropyl)methyl]amino}carbonyl)cyclohexyl]-4-methoxybenzamide,
Trans-N-[2-({[cyano(cyclopropyl)methyl]amino}carbonyl)cyclohexyl]-4-methoxybenzamide,
Trans-N-[2-({[cyano(cyclopropyl)methyl]amino}carbonyl)cyclohexyl]-4-ethylbenzamide,
Cis-N-[2-({[cyano(cyclopropyl)methyl]amino}carbonyl)cyclohexyl]-3,4-difluorobenzamide,
Cis-N-[2-({[cyano(cyclopropyl)methyl]amino}carbonyl)cyclohexyl]-4-cyanobenzamide,
Cis-N-[2-({[cyano(cyclopropyl)methyl]amino}carbonyl)cyclohexyl]-4-tert-butylbenzamide, and
Cis-N-[2-({[cyano(cyclopropyl)methyl]amino}carbonyl)cyclohexyl]-3,4,5-trimethoxybenzamide, and pharmaceutically acceptable esters thereof Other especially preferred compounds of formula (I) are
Cis-5-Methoxy-benzofuran-2-carboxylic acid [2-(cyanomethyl-carbamoyl)-cyclohexyl]-amide,
Trans-5-Methoxy-benzofuran-2-carboxylic acid [2-(cyanomethyl-carbamoyl)-cyclohexyl]-amide,
Cis-2-{[(4-chlorophenyl)acetyl]amino}-N-[cyano(cyclopropyl)methyl]cyclohexanecarboxamide,
Cis-N-[2-({[cyano(cyclopropyl)methyl]amino}carbonyl)cyclohexyl]-4-ethylbenzamide,
Cis-N-[2-({[cyano(cyclopropyl)methyl]amino}carbonyl)cyclohexyl]-4-ethoxybenzamide,
Cis-N-[2-({[cyano(cyclopropyl)methyl]amino}carbonyl)cyclohexyl]-4-methoxybenzamide, Trans-N-[2-({[cyano(cyclopropyl)methyl]amino}carbonyl)cyclohexyl]-4-methoxybenzamide,
Trans-N-[2-({[cyano(cyclopropyl)methyl]amino}carbonyl)cyclohexyl]-4-ethylbenzamide,
Cis-N-[2-({[cyano(cyclopropyl)methyl]amino}carbonyl)cyclohexyl]-4-cyanobenzamide, and
Cis-N-[2-({[cyano(cyclopropyl)methyl]amino}carbonyl)cyclohexyl]-4-tert-butylbenzamide,
and pharmaceutically acceptable esters thereof.

The invention also relates to the use of compounds of formula (I) as defined above for the treatment or prophylaxis of diseases which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In a preferred embodiment, the invention relates to the use of compounds as defined above for the treatment or prophylaxis of osteoporosis, instable angina pectoris or plaque rupture.

Further, the invention relates to compounds as defined above for use as therapeutic active substances, in particular in context with diseases which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In a preferred embodiment, the invention relates to compounds as defined above for use as therapeutic active substances, in particular in context with osteoporosis, instable angina pectoris or plaque rupture.

The invention also relates to pharmaceutical compositions comprising a compound as defined above and a pharmaceutically acceptable carrier and/or adjuvant, in particular for use in context with diseases which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In a preferred embodiment, the invention relates to pharmaceutical compositions comprising a compound as defined above and a pharmaceutically acceptable carrier and/or adjuvant for use in context with osteoporosis, instable angina pectoris or plaque rupture.

A further embodiment of the present invention refers to the use of compounds as defined above for the preparation of medicaments for the treatment or prophylaxis of diseases which are associated with cystein proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In a preferred embodiment, the invention relates to the use of compounds as defined above for the preparation of medicaments for the treatment or prophylaxis of osteoporosis, instable angina pectoris or plaque rupture. Such medicaments comprise a compound as defined above.

An additional embodiment of the invention relates to a method for the prophylactic and/or therapeutic treatment of disorders in which cathepsin K plays a significant pathological role, such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease, which method comprises administering a compound as defined above to a human being or an animal. A preferred embodiment of the invention relates to a method for the prophylactic and/or therapeutic treatment of osteoporosis, instable angina pectoris or plaque rupture, which method comprises administering a compound as defined above to a human being or an animal.

The invention further relates to a process for the manufacture of compounds of formula (I) which process comprises reacting a compound of formula (II)

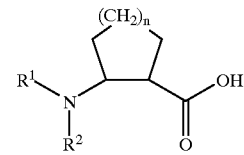

(II)

with a compound of formula (III)

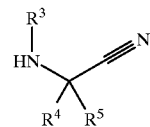

(III)

wherein $R^1$, $R^2$, $R^3$, $R^4$, $R^5$, and n have the significances given above, or reacting a compound of formula (IV)

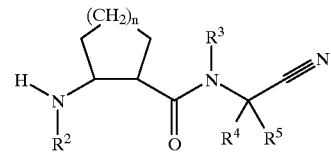

(IV)

with a compound of formula (V) or (VI)

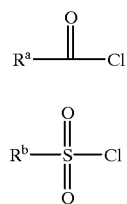

wherein $R^2$, $R^3$, $R^4$, $R^5$, $R^a$, $R^b$ and n have the significances given above.

The invention also relates to a process as described above, which process comprises the preparation of pharmaceutically acceptable salts and/or pharmaceutically acceptable esters. The formation of the esters and/or salts can be carried out at different stages of the process, e.g. with the compound of formula (I) or with the corresponding starting materials.

The reaction of a compound of formula (II) with a compound of formula (III) can be carried out by methods known to the person skilled in the art. The reaction can conveniently be carried out by dissolving compound (II), compound (III), TPTU (O-1,2-Dihydro-2-oxo-1-pyridyl)-N,N,N',N'-tetramethyluronium tetrafluoroborate) and Hünigsbase (N-Ethyldiisopropylamine) in MeCN and stirring the mixture at room temperature for 6 to 16 hours. The reaction mixture can be concentrated and the product can be obtained by methods known to the person skilled in the art, e.g. by extraction and column chromatography. Alternatively, a compound of formula (II) can be dissolved in $CH_2Cl_2$ and reacted for 6 to 16 hours at room temperature with a compound of formula (III) in the presence of N-methylmorpholin, HOBT and EDCI. The product can be isolated by methods known per se, e.g. by extraction and HPLC.

The reaction of a compound of formula (IV) with a compound of formula (V) or (VI) is conveniently carried out by preparing a solution of compound (IV) in $CH_2Cl_2$ and adding a solution of compound (V) or (VI) in $CH_2Cl_2$. To this mixture, Triethylamin is added and after shaking 6 to 16 hours at room temperature formic acid is added. The product can be isolated and purified by methods known per se, e.g. by evaporation of the solvent and HPLC.

In order to prepare pharmaceutically acceptable salts and/or pharmaceutically acceptable esters of compounds of formula (I), it is possible to prepare the corresponding esters and/or salts starting from the compounds of formula (I). It is also possible, to form the esters and/or salts at an earlier stage, e.g. to form the corresponding salts an/or esters of the corresponding starting materials. The methods to prepare pharmaceutically acceptable salts and/or pharmaceutically acceptable esters as defined before are known in the art.

Compounds of formula (II) are prepared by methods known to the person skilled in the art. See, for example, the procedures cited in the novabiochem 2000 catalog, pp. 1–34. Conveniently, the corresponding amino acid is linked to the desired substituent $R^1$ analogously to the methods described in the examples. The resulting compound (II) is isolated by methods known per se, e.g. by extraction and evaporation of the solvent.

Compounds of formula (III) can conveniently be obtained by adding a solution of the corresponding aldehyde in $CH_2Cl_2$ to a solution of $NH_4Cl$ and NaCN in $H_2O$ and MeOH at 0° C. The corresponding aldehydes are available from Aldrich or can be prepared by methods known in the art from aldehydes available from Aldrich. The mixture is stirred and allowed to warm to room temperature. After addition of $NH_3$ solution and completion of the reaction the resulting compound of formula (III) is isolated and purified by methods known to the person skilled in the art, e.g. by extraction. The corresponding hydrochlorid can be prepared by methods known per se.

Chiral compounds of formula (III) can conveniently be obtained by adding ammonium bicarbonate to a mixed anhydride (prepared from a suitable t-BOC protected amino acid and di-tert-butyl dicarbonate) at 15° C. The reaction mixture is stirred at room temperature for 1–5 h. After completion of the reaction the resulting t-BOC protected amino acid amide is isolated and purified by methods known to the person skilled in the art, e.g. by extraction. The Boc protected amino acid amide and triethylamine are dissolved in THF and trifluoroacetic acid anhydride at 0° C. The mixture is stirred for 2 h at –10° C. After isolation and purification of the resulting intermediate product, e.g. by evaporation of the solvent and flash chromatography, the t-BOC protective group can be cleaved off with HCl in acetic acid to yield the desired compound of formula (III).

Compounds of formula (IV) can conveniently be obtained by reacting the corresponding t-BOC protected amino acid with a compound of formula (III) analogous to the method described above. The corresponding t-BOC protected amino acids can be prepared by methods known to the person skill in synthetic organic chemistry. See, for example, procedures cited in novabiochem 2000 calatog above. After isolation and purification of the resulting intermediate product, e.g. by evaporation of the solvent and flash chromatography, the t-BOC protective group can be cleaved off with trifluoroacetic acid to yield the desired compound of formula (IV) with trifluoro-acetic acid.

Compounds of formula (V) and (VI) are either commercially available or can be obtained by methods known in the art.

The following scheme (corresponds to method G in the experimental section) shows another possibility to prepare compounds of the present invention by solid phase synthesis.

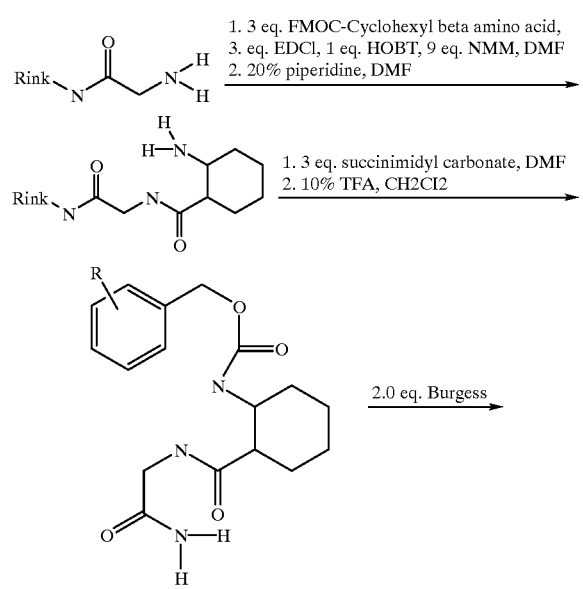

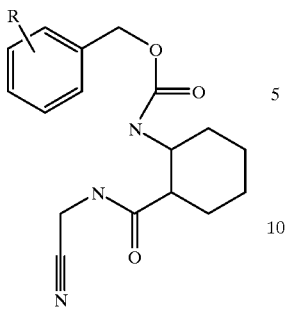

R = any combination of H, alkyl, halogen, acetyl, amino acetyl, alkoxy, nitro, thio, thioalkyl, sulfonyl, sulfoxyl To 1 eq of Rink resin bound glycine (see Rink, *Tetrahedron Lett.* 1987, 28, 3787) in DMF is added 1 eq of educt 1 (a cyclohexanecarboxylic acid derivative available from Aldrich or Acros), EDCI, HOBT, and NMM (N-methylmorpholine). The reaction is shaken overnight at RT. The solvent is removed and the resin washed with dichloromethane, methanol, and again with dichloromethane. The resin is then suspended in DMF and 20% piperidine is added. After 30 minutes reaction time at RT, the solvent is removed by filtration. The resin is washed with dichloromethane, methanol, and again with dichloromethane. The resin is again suspended in DMF and 3 eq. of the corresponding succinimidyl carbonate (educt 2, available from Aldrich or Acros) is added. The reaction is shaken overnight at RT. The resin is then filtered and washed with dichloromethane, methanol, and again with dichloromethane. The resin is then suspended in a 10% solution of trifluoroacetic acid in dichloromethane. After 30 minutes reaction time at room temperature, the resin is filtered and washed with dichloromethane. The filtrate is concentrated to dryness to yield the amide. The amide is subjected to dehydration using Burgess reagent (Methoxycarbonylsulfamoyl-triethylammonium hydroxide, see Atkins, G. M., Burgess, E. M. *J. Am. Chem. Soc.* 1968, 90, 4744). The amide is diluted in dichloromethane or in the trans case 1,4-dioxane. One eq. of Burgess reagent is added and the reaction is stirred for 2 h at RT, after which a second eq. of Burgess is added and the reaction is stirred for an additional 2 h. The crude reaction mixture is evaporated to dryness and then diluted in ethyl acetate. The desired compound is isolated and purified by methods known to the person skilled in the art, e.g by extraction and by preparative HPLC.

The following scheme (corresponds to method H in the experimental section) shows another possibility to prepare compounds of the present invention by solid phase synthesis.

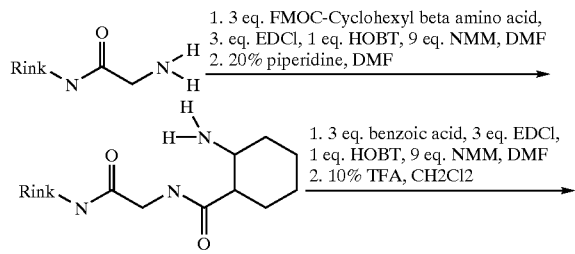

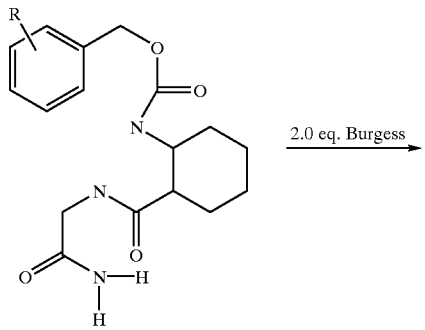

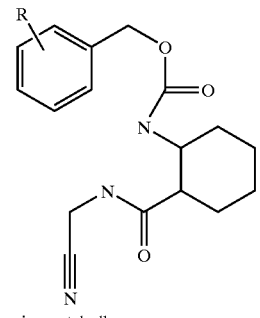

R = any combination of H, alkyl, halogen, acetyl, amino acetyl, alkoxy, nitro, thio, thioalkyl, sulfonyl, sulfoxyl To 1 eq of Rink resin bound glycine (see Rink, *Tetrahedron Lett.* 1987, 28, 3787) in DMF is added 1 eq. of educt 1 (a cyclohexanecarboxylic acid derivative), EDCI, HOBT, and NMM. The reaction is shaken overnight at RT. The solvent is removed and the resin washed with dichloromethane, methanol, and again with dichloromethane. The resin is then suspended in DMF and 20% piperidine is added. After 30 minutes reaction time at RT, the solvent is removed by filtration. The resin is washed with dichloromethane, with methanol, and again with dichloromethane. The resin is again suspended in DMF and 3 eq. the corresponding carboxylic acid (educt 2) is added, along with EDCI, HOBT, and NMM. The reaction is shaken overnight at RT. The resin is then filtered and washed with dichloromethane, methanol, and again with dichloromethane. The resin is then suspended in a 10% solution of trifluoroacetic acid in dichloromethane. After 30 minutes reaction time at RT, the resin is filtered and washed with dichloromethane. The filtrate is concentrated to dryness to yield the amide. The amide is subjected to dehydration using Burgess reagent (Methoxycarbonylsulfamoyl-triethylammonium hydroxide, see Atkins, G. M., Burgess, E. M. *J. Am. Chem. Soc.* 1968, 90, 4744). The amide is diluted in dichloromethane or in the trans case 1,4-dioxane. One eq. of Burgess is added and the reaction stirred for 2 h at RT, after which a second eq. of Burgess is added and the reaction stirred for an additional 2 h. The crude reaction mixture is evaporated to dryness and then diluted in ethyl acetate. The desired compound is isolated and purified by methods known to the person skilled in the art, e.g by extraction and by preparative HPLC.

All educts used to prepare compounds by solid phase synthesis are either commercially available or can be obtained by methods known in the art or by methods described herein.

The following scheme (corresponds to methods I and F in the experimental section) shows another possibility to prepare compounds of the present invention.

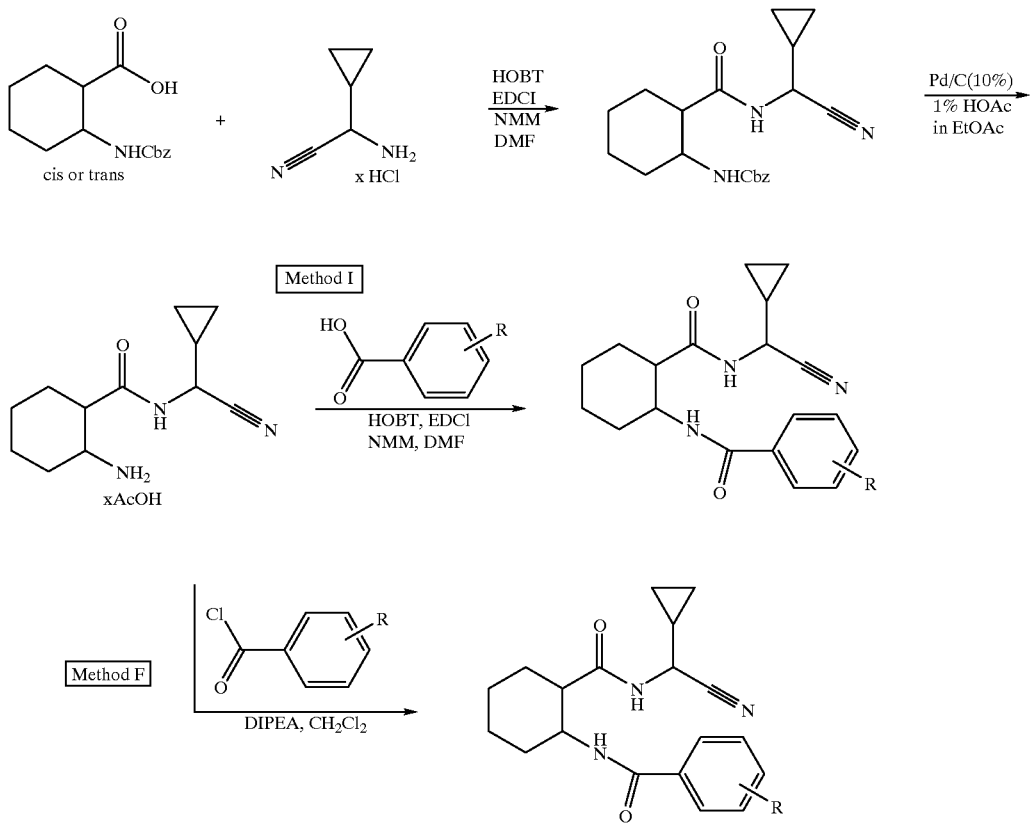

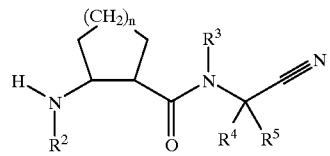

HOBT is added to a solution of the acid in DMF. The mixture is stirred at room temperature for 1 hour and 2-Amino-cyclohexanecarboxylic acid(1-cyano-1-cyclopropyl-methyl)-amide acetic acid salt, EDCI and NMM (N-methylmorpholine) are added. The mixture is stirred at room temperature overnight and concentrated. The desired compound is isolated and purified by methods known to the person skilled in the art, e.g by extraction and by preparative TLC. Starting materials for this method can be purchased from Aldrich or Acros or can be prepared from reagents purchased from Aldrich or Acros by methods known in the art.

DIPEA (diisopropylethylamine) is added to a solution of 2-Amino-cyclohexanecarboxylic acid(1-cyano-1-cyclopropyl-methyl)-amide acetic acid salt in $CH_2Cl_2$. The mixture is stirred at room temperature for 45 minutes. The acid chloride is added and the reaction mixture is stirred at room temperature under $N_2$ overnight. The desired compound is isolated and purified by methods known to the person skilled in the art, e.g by extraction and by preparative TLC (PathF). Starting materials for this method can be purchased from Aldrich or Acros or can be prepared from reagents purchased from Aldrich or Acros by methods known in the art.

The isolated cis- and trans-forms of the product are obtained by starting from the corresponding cis- or trans-form of the cyclohexane derivative.

The present invention relates to all compounds of formula (I), as prepared by one of the processes described above.

The invention also relates to compounds of formula (IV)

(IV)

wherein $R^2$, $R^3$, $R^4$, $R^5$ and n are as defined above.

The inhibitory activity of the compounds against cathepsin K, S, L and B was tested at room temperature in 96-wells opaque white polystyrene plates (Costar). The cathepsin K inhibitory activity was tested as follows:

5 μl of an inhibitor diluted in 5 mM sodium phosphate, NaCl 15 mM pH 7.4 containing 1% DMSO (final concentrations: 10–0.0001 μM) were preincubated for 10 min with 35 μl of human recombinant cathepsin K (final concentration: 1 nM) diluted in assay buffer (100 mM sodium acetate pH 5.5 containing 5 mM EDTA and 20 mM cysteine). After addition of 10 μl of the fluorogenic substrate Z-Leu-Arg-MCA diluted in assay buffer (final concentration: 5 μM), increase of fluorescence (excitation at 390 nm and emission at 460 nm) was measured for 7.5 min every 45 sec. The initial velocity (RFU/min) was derived from the linear fit of the 11 reading points.

The cathepsin B inhibitory activity was assayed under the same conditions as the cathepsin K inhibitory activity using human liver cathepsin B (Calbiochem) at a final concentration of 1 nM.

The cathepsin L inhibitory activity was assayed under the same conditions as the cathepsin K inhibitory activity using, human liver cathepsin L (Calbiochem) at a final concentration of 3 nM.

Cathepsin S inhibitory activity was assayed analogeously to the cathepsin K inhibitory activity, except that the buffer was 100 mM potassium phosphate, 5 mM EDTA, 5 mM DTT (freshly added), 0.01% Triton X-100, pH 6.5 and the fluorogenic substrate was Z-Val-Val-Arg-MCA (Bachem) (final concentration: 20 µM). Human recombinant cathepsin S (Maubach et al., *Eur. J. Biochem.* 1997, 250, 745–750) was used at a final concentration of 0.5 nM.

The results are given as $IC_{50}$ values which denote the concentration of the inhibitor at which the enzymatic activity is inhibited by 50%. The $IC_{50}$ values are determined from a linear regression curve from a logit-log plot.

| Example | Cathepsin K $IC_{50}$ (µMol/l) | Cathepsin S $IC_{50}$ (µMol/l) | Cathepsin L $IC_{50}$ (µMol/l) | Cathepsin B $IC_{50}$ (µMol/l) |
|---|---|---|---|---|
| 8.1 | 0.005 | >10 | 4.7 | 4.6 |
| 8.2 | 0.016 | 0.64 | 1.2 | 0.095 |
| 8.15 | 0.016 | 1.26 | 0.58 | 0.44 |
| 8.12 | 0.029 | 2.61 | 1.38 | 0.64 |
| 8.7 | 0.027 | >10 | 4.69 | 1.38 |

It will be appreciated that the compounds of formula (I) in this invention may be derivatised at functional groups to provide derivatives which are capable of conversion back to the parent compounds in vivo.

As mentioned earlier, medicaments containing a compound of formula (I) are also an object of the present invention, as is a process for the manufacture of such medicaments, which process comprises bringing one or more compounds of formula (I) and, if desired, one or more other therapeutically valuable substances into a galenical administration form.

The pharmaceutical compositions may be administered orally, for example in the form of tablets, coated tablets, dragees, hard or soft gelatine capsules, solutions, emulsions or suspensions. Administration can also be carried out rectally, for example using suppositories; locally or percutaneously, for example using ointments, creams, gels or solutions; or parenterally, e.g. intravenously, intramuscularly, subcutaneously, intrathecally or transdermally, using for example injectable solutions. Furthermore, administration can be carried out sublingually or as opthalmological preparations or as an aerosol, for example in the form of a spray.

For the preparation of tablets, coated tablets, dragees or hard gelatine capsules the compounds of the present invention maybe admixed with pharmaceutically inert, inorganic or organic excipients. Examples of suitable excipients for tablets, dragees or hard gelatine capsules include lactose, maize starch or derivatives thereof, talc or stearic acid or salts thereof.

Suitable excipients for use with soft gelatine capsules include for example vegetable oils, waxes, fats, semi-solid or liquid polyols etc.; according to the nature of the active ingredients it may however be the case that no excipient is needed at all for soft gelatine capsules.

For the preparation of solutions and syrups, excipients which may be used include for example water, polyols, saccharose, invert sugar and glucose.

For injectable solutions, excipients which may be used include for example water, alcohols, polyols, glycerine, and vegetable oils.

For suppositories, and local or percutaneous application, excipients which may be used include for example natural or hardened oils, waxes, fats and semi-solid or liquid polyols.

The pharmaceutical compositions may also contain preserving agents, solubilising agents, stabilising agents, wetting agents, emulsifiers, sweeteners, colorants, odorants, salts for the variation of osmotic pressure, buffers, coating agents or antioxidants. As mentioned earlier, they may also contain other therapeutically valuable agents.

It is a prerequisite that all adjuvants used in the manufacture of the preparations are non-toxic.

Intravenous, intramuscular or oral administration is a preferred form of use. The dosages in which the compounds of formula (I) are administered in effective amounts depend on the nature of the specific active ingredient, the age and the requirements of the patient and the mode of application. In general, daily dosages of about 1 mg–1000 mg, preferably 5 mg–500 mg, per day come into consideration.

The following Examples shall illustrate preferred embodiments of the present invention but are not intended to limit the scope of the invention.

The corresponding starting materials are either commercially available or can be obtained by methods known in the art (e.g. from: DE 26 24 290; WO 98/0354; Chem. Pharm. Bull., 38(2), 350–354 (1990), Chiral Synthon Obtained with Pig Liver Esterase: Introduction of Chiral Centers into Cyclohexene Skeleton; J. Chem. Soc. Perkin Trans., 1, 1411–1415 (1994), Asymmetric Synthesis of (−)-(1R,2S)-Cispentacin and Related cis- and trans-2-Amino Cyclopentane- and Cyclohexane-1-carboxylic Acids) or can be obtained by methods analogous to the methods described before.

EXAMPLE 1

Preparation of (R,S)-α-Amino-3-Bromophenylacetonitrile $NH_4Cl$ (2.14 g, 40 mmol) and NaCN (1.96 g, 40 mmol) are dissolved in 20 ml $H_2O$ 20 ml MeOH and cooled to 0° C. A solution of 3-bromobenzaldehyde (4.68 ml, 40 mmol) in 15 ml $CH_2Cl_2$ and 15 MeOH is added dropwise over 30 min. The mixture is allowed to warm to RT and stirred for 0.5 h. $NH_3$ solution (25 % in $H_2O$) (6 ml, 80 mmol) is added. The mixture is stirred for 16 h at RT. The organic solvents are evaporated and $H_2O$ is added (5 to 10 ml). The water layer is extracted with $CH_2Cl_2$ (2×50 ml) and the latter is washed with $H_2O$ (20 ml) and brine (20 ml), dried over $Na_2SO_4$ and evaporated. The oily residue is dissolved in 75 ml ether. While stirring vigorously dropwise a 4 M HCl solution in dioxane is added. A solid precipitates and is filtered and dried. To recrystallize the solid is dissolved in as little MeOH as possible (do not heat!). Now, while stirring, ether is added until precipitation has finished. The precipitate is filtered and dried in vacuo.

Yield: 40% MS: 229 (MNH4+)

EXAMPLE 2

Preparation of Chiral Amino Nitriles:

(S)-(Carbamoyl-phenyl-methyl)-carbamic Acid Tert-butyl Ester 0.628 g (7.95 mmol, 1 eq) ammonium bicarbonate is added to the mixed anhydride (prepared from 7.95 mmol (S)-BOC-phenyl glycine and 10.4 mmol di-tert-butyl dicarbonate in 40 ml dioxane and 2.39 mmol pyridine) at 15 ° C. The mixture is stirred for 8 h at this temperature and concentrated. The residue is dissolved in 20 ml ethyl acetate, washed with saturated sodium bicarbonate, 2N HCL, brine, dried over sodium sulfate and evaporated.

Yield: 92%, MS: 251 (MH+), $[\alpha]_D^{25}$=−120.4 (1.00, EtOH) (R)-(Carbamoyl-phenyl-methyl)-carbamic acid tert-butyl ester is prepared analogously to (S)-(Carbamoyl-phenyl-methyl)-carbamic acid tert-butyl ester.

Preparation of (S)-(Cyano-phenyl-methyl)-carbamic Acid Tert-butyl Ester (S)-(Carbamoyl-phenyl-methyl)-carbamic acid tert-butyl ester (1.8 g, 7.19 mmol) and triethylamine (2.2 ml, 15.8 mmol) are dissolved in THF (40 ml) at −10° C. Trifluoroacetic acid anhydride (1.1 ml, 7.91 mmol) is added over 30 min. The mixture is stirred at −10° C. for 2 h and evaporated. Dichloromethane and water are added. The organic phase is separated, dried over sodium sulfate and evaporated. The crude product is purified by chromatography (silica gel, ethyl acetate/hexane=4:1, $R_f$=0.5).

Yield: 81%, MS: 231 (M-H)⁻, $[\alpha]_D^{25}$=+4.1 (1.00, EtOH) (R)-(Cyano-phenyl-methyl)-carbamic acid tert-butyl ester is prepared analogously to (S)-(Cyano-phenyl-methyl)-carbamic acid tert-butyl ester.

Preparation of (S)-Amino-phenyl-acetonitrile Hydrochloride (S)-(Cyano-phenyl-methyl)-carbamic acid tert-butyl ester (0.5 g, 2.15 mmol) is dissolved in 5 ml HCl/abs. AcOH (10%). The mixture is stirred at RT for 2 h and evaporated. The product is washed with dietyl ether and dried in vacuo.

Yield: 98%, MS: 192 (M+Na)⁺, $[\alpha]_D^{25}$=+38.6 (1.00, water) (R)-Amino-phenyl-acetonitrile hydrochloride is prepared analogously to (S)-Amino-phenyl-acetonitrile hydrochloride.

EXAMPLE 3

Preparation of Cis-(2-{(R)- and (S)-[Cyano-(2,4-dimethoxy-phenyl)-methyl]-carbamoyl}-cyclohexyl)-carbamic Acid Benzyl Ester A solution of 0.7 mmol cis-2-Benzyloxycarbonylamino-cyclohexane carboxylic acid (educt 1), 5.2 mmol N-methylmorpholin, 0.15 mmol HOBT and 1.78 mmol EDCI in 12 ml CH₂Cl₂ is added to 0.97 mmol Amino-(3,4-dimethoxy-phenyl)-acetonitrile; hydrochloride (educt 2). After shaking overnight the reaction mixture is extracted with 10 ml 1N HCl and the CH₂Cl₂ is evaporated. The compound is purified by HPLC:

| column: | HP-CombiHT XDB-C18, 21.2 mmI.D. × 50 mm, Series No DN 1020 |
|---|---|
| method: | Flow: 40 ml/min |
| 0 min | 80% water, 20% acetonitrile |
| 0.2 min | 80% water, 20% acetonitrile |
| 3.5 min | 5% water, 95% acetonitrile |
| 4.7 min | 5% water, 95% acetonitrile |
| 4.8 min | 80% water, 20% acetonitrile |
| 4.9 min | 80% water, 20% acetonitrile |
| machine: | Prep HPLC System Dynamax Model SD-1, UV-1 |
| Yield: | 59%, MS: 452(MH+) |

EXAMPLE 4

Preparation of (1S,2R)-{2-(R)- and (S)-[(Cyano-phenyl-methyl)-carbamoyl]-cyclohexyl}-carbamic Acid Benzyl Ester A solution of 0.18 mmol (1S,2R)-2-Benzyloxycarbonylamino-cyclohexane carboxylic acid (educt 1), 0.72 mmol N-ethyldiisopropylamine and 0.18 mmol TPTU in 10 ml acetonitrile is added to 0.18 mmol Amino-phenyl-acetonitrile hydrochloride (educt 2). After stirring overnight the solvent is evaporated. The residue is dissolved in ethyl acetate, extracted with sodium hydrogen-carbonate solution (3×) and brine. The solution is dried over sodium sulfate and evaporated. The compound is purified by flash chromatography (silicagel, ethyl acetate/hexane 7:3).

Yield: 83%, MS: 390(M-H)

EXAMPLE 5

Preparation of Trans-2-(4-Chloro-benzenesulfonylamino)-cyclohexanecarboxylic Acid Trans-2-Aminocyclohexanecarboxylic acid (0.150 g, 1.05 mmol) is dissolved in 1.5 ml of water and NaOH (0.09 g, 2.25 mmol) in 1.5 ml of water is added at 0° C. 4-Chlorobenzene sulfonyl chloride (0.243 g, 1.15 mmol) in 1.5 ml of toluene is added. The reaction mixture is stirred at room temperature for 16 hours. The toluene layer is separated and the aqueous layer is washed twice with toluene. The toluene layers are discarded. Ethyl acetate is added to the aqueous layer (15 ml) and 2M HCl until pH<7. The two phases are separated and the aqueous layer is extracted with ethyl acetate (3×15 mL). The combined organic phases are washed with brine (20 ml), dried over MgSO₄ and the ethyl acetate is removed under reduced pressure leaving a white solid that is dissolved in toluene (2×10 ml) and concentrated .The product is dried in vacuum.

Yield: 70%, MS: 316 (M-H)

Preparation of Trans-2-(4-Chloro-benzenesulfonylamino)-cyclohexanecarboxylic Acid [Cyano-(3-hydroxy-phenyl)-methyl]-amide Trans-2-(4-Chloro-benzenesulfonylamino)-cyclohexanecarboxylic acid (0.095 g, 0.3 mmol) is dissolved in CH₃CN. O-1,2-Dihydro-2-oxo-1-pyridyl)-N,N,N',N'-tetramethyluronium tetrafluoroborate (TPTU, 90.2 mg, 0.3 mmol), N-Ethyldiisopropylamine (DIPEA, 0.208 ml, 1.21 mmol) are added. The amino-(3-hydroxy-phenyl)-acetonitrile in CH₃CN (1.5 ml) is added. The mixture is stirred at RT for 16 hours. The solution is filtered and concentrated. The residue is dissolved in CH₂Cl₂ (15 mL) and extracted with NH₄Cl (2×10 ml). The H₂O layers are extracted with CH₂Cl₂ (2×15 ml). The collected CH₂Cl₂ layers are dried over MgSO₄ and evaporated. The solid is purified by preparative HPLC.

| column: | YMC; CombiPrep ODS_AQ; 50*20 mmI.D; S-5 um, 120A |
|---|---|
| method: | Flow: 40 ml/min |
| 0 min | 90% water, 10% acetonitrile |
| 0.1 L | 90% water, 10% acetonitrile |
| 3.5 min | 5% water, 95% acetonitrile |
| 5.5 min | 5% water, 95% acetonitrile |
| 5.7 min | 80% water, 20% acetonitrile |
| 5.8 min | 80% water, 20% acetonitrile |
| machine: | Prep HPLC System Dynamax Model SD-1, UV-1. |
| Yield: | 26%, MS: 470(MNa+) |

EXAMPLE 6

Preparation of Carbonic Acid 4-Nitro-phenyl Ester Thiophen-2-ylmethyl Ester

To a solution of the Thiophen-2-yl-methanol (0.412 g, 3.6 mmol) in CH₂Cl₂ (6 ml) is added pyridine (0.291 ml, 3.6 mmol) and 4-Nitrophenylchloroformate (0.728 g, 3.6 mmol) at 0° C. After shaking overnight, the reaction mixture is extracted with NH₄Cl (5 ml) and the CH₂Cl₂ is evaporated leaving a white solid which is used without further purification.

Preparation of cis-2-(Thiophen-2-ylmethoxycarbonylamino)-cyclohexanecarboxylic Acid To a solution of Trans-2-amino-1-cyclohexane carboxylic acid (100 mg, 0.7 mmol) in 1 mL of water is added 2M aqueous Na₂CO₃ until pH=9–10 (2 mL). A solution of the carbonic acid 4-nitro-phenyl ester thiophen-2-ylmethyl ester (195 mg, 0.7 mmol) in THF (1 mL) is added at 0° C. and, after 10 minutes, 1 ml of the 2M Na₂CO₃ is added to the reaction. The mixture is allowed to warm to RT and vigorously stirred overnight. The reaction mixture is diluted with 0.5N HCl until pH=4-3 and the water layer is extracted three times with CH₂Cl₂ (10 ml). The organic phases are combined, dried (MgSO₄), and concentrated under reduced pressure. The resulting product is used in the next step without further purification.

Yield 68% MS: 282 (M-H)

Preparation of Trans-(2-{[Cyano-(3-hydroxy-phenyl)-methyl]-carbamoyl}-cyclohexyl)-carbamic Acid Thiophen-2-ylmethyl Ester Trans-(2-[Cyano-(3-hydroxy-phenyl)-methyl]-carbamoyl}-cyclohexyl)-carbamic acid thiophen-2-ylmethyl ester (0.094 g, 0.33 mmol) is dissolved in DMF (1 ml). O-1,2-Dihydro-2-oxo-1-pyridyl)-N,N,N',N'-tetramethyluronium tetrafluoroborate (TPTU, 0.099 mg, 0.33 mmol) and N-Ethyldiisopropylamine (DIPEA, 0.228 ml, 1.32 mmol) are added. The amino-(3-hydroxy-phenyl)-acetonitrile in DMF (1.5 ml) is added and the mixture is stirred overnight at RT. The reaction mixture is filtered and the product is obtained by HPLC.

| | |
|---|---|
| column: | YMC; CombiPrep ODS_AQ; 50*20 mml.D; S-5 um, 120A |
| method: | Flow: 40 ml/min |
| 0 min | 90% water, 10% acetonitrile |
| 0.1 L | 90% water, 10% acetonitrile |
| 3.5 min | 5% water, 95% acetonitrile |
| 5.5 min | 5% water, 95% acetonitrile |
| 5.7 min | 80% water, 20% acetonitrile |
| 5.8 min | 80% water, 20% acetonitrile |
| machine: | Prep HPLC System Dynamax Model SD-1, UV-1. |
| Yield | 24%, MS: 436(MNa+) |

EXAMPLE 7

Preparation of 2-Amino-cyclohexanecarboxylic Acid [Cyano-(3,4-dimethoxy-phenyl)-methyl]-amide; Compound with Trifluoro-acetic Acid To a solution of 15.7 mmol 2-tert-Butoxycarbonylamino-cyclohexanecarboxylic acid, 17.2 mmol (R,S)-Amino-(3,4-dimethoxy-phenyl)-acetonitrile; hydrochloride, 1.57 mmol HOBT and 18.8 mmol EDCI in 150 ml CH₂Cl₂ is added 109.7 mmol N-methylmorpholine. After stirring overnight at RT the reaction mixture is extracted with 150 ml 10% KHSO₄ and 150 ml sat. NaHCO₃, dried over MgSO₄, evaporated and purified by flash chromatography (4 cm Glassfrit, 2 cm silicagel 0.04–0.063, eluent 400 ml CH₂Cl₂). BOC-cleavage is performed with 17 ml TFA in 50 ml CH₂Cl₂ within 4 hours at RT. Evaporation yields a brown oil which is used without further purification.

Preparation of cis-2-(3-Phenyl-acryloylamino)-cyclohexanecarboxylic Acid [(R)- and (S)-Cyano-(3,4-dimethoxy-phenyl)-methyl]-amide To a solution of 0.17 mmol cis-2-Amino-cyclohexanecarboxylic acid [cyano-(3,4-dimethoxy-phenyl)-methyl]-amide; compound with trifluoro-acetic acid (educt 1) in 3 ml CH₂Cl₂ is added a solution of 0.187 mmol trans-Cinnamoyl cholride (educt 2) in 1 ml CH₂Cl₂. To this mixture is added 0.36 mmol triethylamine. After shaking overnight at RT formic acid is added, the CH₂Cl₂ is evaporated and the compound purified by HPLC:

| | |
|---|---|
| column: | HP-CombiHT XDB-C18, 21.2 mmI.D. × 50 mm, Series No DN 1020 |
| method: | Flow: 40 ml/min |
| 0 min | 80% water, 20% acetonitrile |
| 0.2 min | 80% water, 20% acetonitrile |
| 3.5 min | 5% water, 95% acetonitrile |
| 4.7 min | 5% water, 95% acetonitrile |
| 4.8 min | 80% water, 20% acetonitrile |
| 4.9 min | 80% water, 20% acetonitrile |
| machine: | Prep HPLC System Dynamax Model SD-1, UV-1 |
| Yield: | 19%, MS: 448 (MH+) |

EXAMPLE 8

Preparation of other Compounds of Formula (I)

Several additional compounds of formula (I) have been prepared. The following table shows an overview of the products, the educts and the method used for the preparation.

| No. | Compound | Method | Educt 1 | Educt 2 | MW | MS |
|---|---|---|---|---|---|---|
| 1 | (1R,2R)-(2-{(S)- [Cyano-(3-hydroxy-phenyl) -methyl]-carbamoyl }-cyclohexyl)-carbamic acid benzyl ester | A-2 | (1R,2R)-trans-2-Benzyloxycarbonylamino-cyclohexane carboxylic acid | 2-Amino-2-(3-hydroxyphenyl) acetonitrile | 407.47 | 408 (MH+) |
| 2 | cis-2-(3-Phenyl-acryloylamino)-cyclohexanecarboxylic acid [(R)-and (S)-cyano-(3,4-dimethoxy-phenyl)-methyl]-amide | B | cis-2-Amino-cyclohexanecarboxylic acid [cyano-(3,4-dimethoxy-phenyl)-methyl]-amide; compound with trifluoro-acetic acid | trans-Cinnamoyl oyl chloride | 447.53 | 448(MH+) |
| 3 | (R)-{2-[(S)-(Cyano-phenyl-methyl)-(R)-carbamoyl]-cyclohexyl}-carbamic acid benzyl ester | A-2 | (1R,2R)-trans-2-Benzyloxycarbonylamino-cyclohexane carboxylic acid | (S)-Amino-phenyl-acetonitrile; hydrochloride | 391.47 | 409 (MNH4+) |

-continued

| No. | Compound | Method | Educt 1 | Educt 2 | MW | MS |
|---|---|---|---|---|---|---|
| 4 | syn-{2-[(S)-(Cyano-phenyl-methyl)-carbamoyl]-cyclohexyl}-carbamic acid benzyl ester | A-2 | cis-2-Benzyloxycarbonylamino-cyclohexane carboxylic acid | (S)-Amino-phenyl-acetonitrile; hydrochloride | 391.47 | 409 (MNH4+) |
| 5 | cis-(2-{(R)- and (S)-[Cyano-(2,4-dimethoxy-phenyl)-methyl]-carbamoyl }-cyclohexyl)-carbamic acid benzyl ester | A | cis-2-Benzyloxycarbonylamino-cyclohexane carboxylic acid | Amino-(3,4-dimethoxy-phenyl)-acetonitrile; hydrochloride | 451.52 | 452 (MH+) |
| 6 | trans-2-(4-Chloro-benzenesulfonylamino)-cyclohexanecarboxylic acid [cyano-(3-hydroxy-phenyl)-methyl]-amide | C | trans-2-(4-Chloro-benzenesulfonylamino)-cyclohexanecarboxylic acid | Amino-(3-hydroxy-phenyl)-acetonitrile | 447.94 | 470 (MNa+) |
| 7 | trans-{2-[(Benzo[1,3]dioxol-5-yl-cyano-methyl)-carbamoyl]-cyclohexyl}-carbamic acid benzyl ester | A-2 | trans-2-Benzyloxycarbonylamino-cyclohexane carboxylic acid | Amino-benzo[1,3]dioxol-5-yl-acetonitrile; hydrochloride | 435.48 | 436 (MH+) |
| 8 | cis-(2-{[Cyano-(3-hydroxy-phenyl)-methyl]-carbamoyl }-cyclohexyl)-carbamic acid benzyl ester | A-2 | cis-2-Benzyloxycarbonylamino-cyclohexane carboxylic acid | 2-Amino-2-(3-hydroxyphenyl) acetonitrile | 407.47 | 425 (MNH4+) |
| 9 | trans-(2-{[Cyano-(3-hydroxy-phenyl)-methyl]-carbamoyl}-cyclohexyl)-carbamic acid benzyl ester | A-2 | trans-2-Benzyloxycarbonylamino-cyclohexane carboxylic acid | 2-Amino-2-(3-hydroxyphenyl) acetonitrile | 407.47 | 425 (MNH4+) |
| 10 | cis-2-(3-Phenyl-acryloylamino-cyclohexanecarboxylic acid ((R)- and (S)-cyano-phenyl-methyl-amide | B | cis-2-Amino-cyclohexanecarboxylic acid (cyano-phenyl-methyl)-amide; compound with trifluoro-acetic acid | trans-Cinnamoyl cholride | 387.48 | 487 (MH+) |
| 11 | (2-{[Cyano-(3,4-dimethoxy-phenyl)-methyl]-carbamoyl}-cyclohexyl)-carbamic acid benzyl ester (1 cis-racemate) | A-2 | cis-2-Benzyloxycarbonylamino-cyclohexane carboxylic acid | Amino-(3,4-dimethoxy-phenyl)-acetonitrile; hydrochloride | 451.53 | 474 (MNa+) |
| 12 | cis-{2-[(R)- and (S)-(Cyano-m-tolyl-methyl)-carbamoyl]-cyclohexyl}-carbamic acid benzyl ester | A | cis-2-Benzyloxycarbonylamino-cyclohexane carboxylic acid | Amino-m-tolyl-acetonitrile; hydrochloride | 405.5 | 406 (MH+) |
| 13 | (2-{[Cyano-(3-hydroxy-phenyl)-methyl]-carbamoyl}-cyclohexyl)-carbamic acid thiophen-3-ylmethyl ester | D | cis-2-(Thiophen-3-ylmethoxycarbonylamino)-cyclohexanecarboxylic acid | 2-Amino-2-(3-hydroxyphenyl)acetonitrile | 413.5 | 436 (MNa+) |
| 14 | cis-(2-{(R)- and (S)-[Cyano-(4-methoxy-phenyl)-methyl-carbamoyl]-cyclohexyl)-carbamic acid benzyl ester | A | cis-2-Benzyloxycarbonylamino-cyclohexane carboxylic acid | Amino-(4-methoxy-phenyl)-acetonitrile; hydrochloride | 421.49 | 394 (MNa+) |
| 15 | cis-(2-{(R)- and (S)-[Cyano-(3-methoxy-phenyl)-methyl]-carbamoyl}-cyclohexyl)-carbamic acid benzyl ester | A | cis-2-Benzyloxycarbonylamino-cyclohexane carboxylic acid | Amino-(3-methoxy-phenyl)-acetonitrile; hydrochloride | 421.49 | 444 (MNa+) |
| 16 | trans-(2-{[Cyano-(3-hydroxy-phenyl)-methyl]-carbamoyl}-cydohexyl)-carbamic acid thiophen-2-ylmethyl ester | D | trans-2-(Thiophen-2-ylmethoxycarbonylamino)-cyclohexanecarboxylic acid | 2-Amino-2-(3-hydroxyphenyl) acetonitrile | 413.5 | 436 (MNa+) |
| 17 | cis-(2-{(R)- and (S)-[(3-Chloro-phenyl)-cyano-methyl]-carbamoyl}-cyclohexyl)-carbamic acid benzyl ester | A | cis-2-Benzyloxycarbonylamino-cyclohexane carboxylic acid | Amino-(3-chloro-phenyl)-acetonitrile hydrochloride | 425.91 | 448 (MNa+) |
| 18 | cis-{2-[(Cyano-phenyl-methyl)-carbamoyl]-cydohexyl}-carbamic acid benzyl ester | A-2 | cis-2-Benzyloxycarbonylamino-cyclohexane carboxylic acid | Amino-phenyl-acetonitrile; hydrochloride | 391.47 | 414 (MNa+) |
| 19 | trans-(2-{[(3-Bromo-phenyl)-cyano-methyl]-carbamoyl}-cyclohexyl)-carbamic acid benzyl ester | A-2 | cis-2-Benzyloxycarbonylamino-cyclohexane carboxylic acid hydrochloride | Amino-(3-bromo-phenyl)-acetonitrile | 470.38 | 493 (MNa+) |
| 20 | cis-(2-{(R)- and (S)-[(4-Bromo-phenyl)-cyano-methyl]-carbamoyl}-cyclohexyl)-carbamic acid benzyl ester | A | cis-2-Benzyloxycarbonylamino-cyclohexane carboxylic acid | Amino-(4-bromo-phenyl)-acetonitrile; hydrochloride | 470.37 | 470 (MH+) |
| 21 | cis-(2-{[(R)- and (S)-Cyano-(3,4-dimethoxy-phenyl)-methyl]-carbamoyl}-cyclohexyl)-carbamic acid cyclopentyl ester | B | cis-2-Amino-cyclohexanecarboxylic acid [cyano-(3,4-dimethoxy-phenyl)-methyl]-amide; compound with trifluoro-acetic acid | Cyclopentyl chloroformate | 429.51 | 430 (MH+) |
| 22 | trans-(2-{[Cyano-(3-hydroxy-phenyl)-methyl]-carbamoyl}-cyclohexyl)-carbamic acid 2-thiophen-2-yl-ethyl ester | D | trans2-(2-Thiophen-2-yl-ethoxycarbonylamino)-cyclohexanecarboxylic acid | 2-Amino-2-(3-hydroxyphenyl) acetonitrile | 427.52 | 428 (MH+) |
| 23 | trans-(2-{[Cyano-(3-hydroxy-phenyl)-methyl]-carbamoyl}-cyclohexyl)-carbamic acid 2-methyl-benzyl ester | D | trans-2-(2-Methyl-benzyloxycarbonylamino)-cyclohexanecarboxylic acid | 2-Amino-2-(3-hydroxyphenyl) acetonitrile | 421.49 | 444 (MNa+) |
| 24 | trans-2-Phenylmethanesulfonylamino-cyclohexanecarboxylic acid [cyano-(3-hydroxy-phenyl)-methyl]-amide | C | trans-2-Phenylmethanesulfonylamino-cydohexanecarboxylic acid | Amino-(3-hydroxy-phenyl)-acetonitrile | 427.52 | 428 (MH+); 450 (M + Na) |
| 25 | trans-(2-{[Cyano-(3-hydroxy-phenyl)-methyl]-carbamoyl}-cyclohexyl)-carbamic acid 2-chloro-benzyl ester | D | trans-2-(2-Chloro-benzyloxycarbonylamino)-cyclohexanecarboxylic acid | 2-Amino-2-(3-hydroxyphenyl) acetonitrile | 441.91 | 464 (MNa+) |
| 26 | cis-(2-{(R)- and (S)-[(4-Chloro-phenyl)-cyano-methyl]-carbamoyl}-cyclohexyl)-carbamic acid benzyl ester | A | cis-2-Benzyloxycarbonylamino-cyclohexane carboxylic acid | Amino-(3-chloro-phenyl)-acetonitrile hydrochloride | 441.91 | 464 (MNa+) |

-continued

| No. | Compound | Method | Educt 1 | Educt 2 | MW | MS |
|---|---|---|---|---|---|---|
| 27 | (2-{[Cyano-(3-hydroxy-phenyl)-methyl]-carbamoyl}-cyclohexyl)-carbamic acid 4-fluoro-benzyl ester | D | 2-(4-Fluoro-benzyloxycarbonylamino)-cyclohexanecarboxylic acid | 2-Amino-2-(3-hydroxyphenyl) acetonitrile | 425.46 | 448 (MNa+) |
| 28 | cis-{2-[(R)-and (S)-(Cyano-phenyl-methyl)-carbamoyl]-cyclohexyl}-carbamic acid naphthalen-2-yl ester | B | cis-2-Amino-cyclohexanecarboxylic acid (cyano-phenyl-methyl)-amide; compound with trifluoro-acetic acid | Chloroformic acid 2-naphthyl ester | 427.5 | 428 (MH+) |
| 29 | cis-{2-[(R)- and (S)-(Cyano-naphthalen-2-yl-methyl)-carbamoyl]-cyclohexyl}-carbamic acid benzyl ester | A | cis-2-Benzyloxycarbonylamino-cyclohexane carboxylic acid | Amino-naphthalen-2-yl-acetonitrile; hydrochloride | 441.53 | 442 (MH+) |
| 30 | trans-(2-{[Cyano-(3-hydroxy-phenyl)-methyl]-carbamoyl}-cyclohexyl)-carbamic acid 3-thiophen-2-yl-propyl ester | D | trans-2-(3-Thiophen-2-yl-propoxycarbonylamino)-cyclohexanecarboxylic acid | 2-Amino-2-(3-hydroxyphenyl) acetonitrile | 413.5 | 436 (MNa+) |
| 31 | trans-2-(4-Cyano-benzenesulfonylamino)-cyclohexanecarboxylic acid [cyano-(3-hydroxy-phenyl)-methyl]-amide | C | trans-2-(4-Cyano-benzenesulfonylamino)-cyclohexanecarboxylic acid | Amino-(3-hydroxy-phenyl)-acetonitrile | 438.51 | 461 (MNa+) |
| 32 | trans-(2-{[(3-Bromo-phenyl)-cyano-methyl]-carbamoyl}-cyclohexyl)-carbamic acid benzyl ester | A-2 | trans-2-Benzyloxycarbonylamino-cyclohexane carboxylic acid | Amino-(3-bromo-phenyl)-acetonitrile hydrochloride | 470.38 | 493 (MNa+) |
| 33 | cis-Acetic acid 4-(R) and (S)-[(2-benzyloxycarbonylamino-cyclohexanecarbonyl)-amino]-cyano-ethyl}-phenyl ester | A | cis-2-Benzyloxycarbonylamino-cyclohexane carboxylic acid | Acetic acid 4-(amino-cyano-methyl)-phenyl | 449.5 | 394 (MNa+) |
| 34 | trans-{2-[(Cyano-phenyl-methyl)-carbamoyl]-cyclohexyl}-carbamic acid benzyl ester | A-2 | trans-2-Benzyloxycarbonylamino-cyclohexane carboxylic acid | Amino-phenyl-acetonitrile; hydrochloride | 391.47 | 414 (MNa+) |
| 35 | cis-N-(2-{[(R) and (S)-Cyano-(3,4-dimethoxy-phenyl)-methyl]-carbamoyl}-cyclohexyl)-benzamide | B | cis-2-Amino-cyclohexanecarboxylic acid [cyano-(3,4-dimethoxy-phenyl)-methyl]-amide; compound with trifluoro-acetic acid | Benzoic acid chloride | 421.49 | 422(MH+) |
| 36 | trans-(2-{[(3-Bromo-4-methoxy-phenyl)-cyano-methyl]-carbamoyl}-cyclohexyl)-carbamic acid benzyl ester | A-2 | trans-2-Benzyloxycarbonylamino-cyclohexane carboxylic acid hydrochloride | Amino-(3-bromo-4-methoxy-phenyl)-acetonitrile; | 500.4 | 519 (MNH4+) |
| 37 | cis-{2-[(R) and (S)-(Cyano-naphthalen-1-yl-methyl)-carbamoyl]-cyclohexyl}-carbamic acid benzyl ester | A | cis-2-Benzyloxycarbonylamino-cyclohexane carboxylic acid | Amino-naphthalen-1-yl-acetonitrile; hydrochloride | 441.53 | 464 (MNa+) |
| 38 | trans-(2-{[Cyano-(3-hydroxy-phenyl)-methyl]-carbamoyl}-cyclohexyl)-carbamic acid 2-methoxy-benzyl ester | D | trans-2-(2-Methoxy-benzyloxycarbonylamino)-cyclohexanecarboxylic acid | 2-Amino-2-(3-hydroxyphenyl) acetonitrile | 437.49 | 460 (MNa+) |
| 39 | (1R,2R)-(2-{(R)-[Cyano-(3-hydroxy phenyl)-methyl]-carbamoyl}-cyclohexyl)-carbamic acid benzyl ester | A-2 | (R,R)-2-Benzyloxycarbonylamino-cyclohexane carboxylic acid | 2-Amino-2-(3-hydroxyphenyl) acetonitrile | 407.47 | 408 (MH+) |
| 40 | trans-(2-{[(3-Bromo-4-methoxy-phenyl)-cyano-methyl]-carbamoyl}-cyclohexyl)-carbamic acid benzyl ester | A-2 | trans-2-Benzyloxycarbonylamino-cyclohexane carboxylic acid | Amino-(3-bromo-4-methoxy-phenyl)-acetonitrile; hydrochloride | 500.4 | 519 (MNH4+) |
| 41 | trans-[2-(Cyanomethyl-carbamoyl)-cyclohexyl]-carbamic acid benzyl ester | A-2 | trans-2-Benzyloxycarbonylamino-cyclohexane carboxylic acid | Acetaminoacetonitrile bisulfate | 315.38 | 316 (MH+) |
| 42 | trans-(2-{[Cyano-(3-hydroxy-phenyl)-methyl]-carbamoyl}-cyclohexyl)-carbamic acid 3-chloro-benzyl ester | D | trans-2-(3-Chloro-benzyloxycarbonylamino)-cyclohexanecarboxylic acid | 2-Amino-2-(3-hydroxyphenyl) acetonitrile | 441.91 | 464 (MNa+) |
| 43 | trans-(2-{[Cyano-(3-hydroxy-phenyl)-methyl]-carbamoyl}-cyclohexyl)-carbamic acid 3-methyl-benzyl ester | D | trans-2-(3-Methyl-benzyloxycarbonylamino)-cyclohexanecarboxylic acid | 2-Amino-2-(3-hydroxyphenyl) acetonitrile | 421.49 | 444 (MNa+) |
| 44 | cis-Biphenyl-4-carboxylic acid (2-{[(R) and (S)-cyano-(3,4-dimethoxy-phenyl)-methyl]-carbamoyl}-cyclohexyl)-amide | B | cis-2-Amino-cyclohexanecarboxylic acid [cyano-(3,4-dimethoxy-phenyl)-methyl]-amide; compound with trifluoro-acetic acid | 4-Biphenylcarbonyl chloride | 497.59 | 498 (MH+) |
| 45 | cis-{2-[(R) and (S)-(Cyano-phenyl-methyl-carbamoyl]-cyclohexyl}-carbamic acid phenyl ester | B | cis-2-Amino-cyclohexanecarboxylic acid (cyano-phenyl-methyl)-amide; compound with trifluoro-acetic acid | Phenyl chloroformate | 377.44 | 378 (MH+) |
| 46 | trans-2-(4-Acetylamino-benzenesulfonylamino)-cyclohexanecarboxylic acid [cyano-(3-hydroxy-phenyl)-methyl]-amide | C | trans-2-(4-Acetylamino-benzenesulfonylamino)-cyclohexanecarboxylic acid | Amino-(3-hydroxy-phenyl)-acetonitrile | 470.55 | 493 (MNa+) |
| 47 | cis-N-{2-[(R) and (S)-(Cyano-phenyl-methyl-carbamoyl]-cyclohexyl}-benzamide | B | cis-2-Amino-cyclohexanecarboxylic acid (cyano-phenyl-methyl)-amide; compound with trifluoro-acetic acid | Benzoic acid chloride | 361.44 | 362 (MH+) |
| 48 | trans-2-{[Cyano-(3-hydroxy-phenyl)-methyl]-carbamoyl}-cyclohexyl)-carbamic acid 3-methoxy-benzyl ester | D | trans-2-(3-Methoxy-benzyloxycarbonylamino)-cyclohexanecarboxylic acid | 2-Amino-2-(3-hydroxyphenyl) acetonitrile | 437.49 | 460 (MNa+) |
| 49 | trans-(2-{[Cyano-(3-hydroxy-phenyl)-methyl]-carbamoyl}-cyclohexyl)-carbamic acid 4-methyl-benzyl ester | D | trans-2-(4-Methyl-benzyloxycarbonylamino)-cyclohexanecarboxylic acid | 2-Amino-2-(3-hydroxyphenyl) acetonitrile | 421.49 | 441 (MNa+) |

-continued

| No. | Compound | Method | Educt 1 | Educt 2 | MW | MS |
|---|---|---|---|---|---|---|
| 50 | cis-{2-[(Benzo[1,3]dioxol-5-yl-cyano-methyl)-carbamoyl]-cyclohexyl}-carbamic acid benzyl ester | A-2 | cis-2-Benzyloxycarbonylamino-cyclohexane carboxylic acid | Amino-benzo[1,3]dioxol-5-yl-acetonitrile; hydrochloride | 435.48 | 453 (MNH4+) |
| 51 | trans-4-Cyano-N-(2-{[cyano-(3-hydroxy-phenyl)-methyl]-carbamoyl}-cyclohexyl)-benzamide | C | trans-2-(4-Cyano-benzoylamino)-cyclohexanecarboxylic acid | Amino-(3-hydroxy-phenyl)-acetonitrile | 402.45 | 425 (MNa+) |
| 52 | trans-(2-{[Cyano-(3-hydroxy-phenyl)-methyl]-carbamoyl}-cyclohexyl)-carbamic acid 4-methoxy-benzyl ester | D | trans-2-(4-Methoxy-benzyloxycarbonylamino)-cyclohexanecarboxylic acid | 2-Amino-2-(3-hydroxyphenyl)acetonitrile | 437.49 | 460 (MNa+) |
| 53 | cis-2-(3-Cyclopentyl-propionylamino)-cyclohexanecarboxylic acid [(R)-and (S)-cyano-(3,4-dimethoxy-phenyl)-methyl]-amide | B | cis-2-Amino-cyclohexanecarboxylic acid [cyano-(3,4-dimethoxy-phenyl)-methyl]-amide; compound with trifluoro-acetic acid | Cyclopentyl-propionyl chloride | 441.57 | 442 (MH+) |
| 54 | (2-{[Cyano-(3,4-dimethoxy-phenyl)-methyl]-carbamoyl}-cyclohexyl)-carbamic acid benzyl ester (1 cis-racemate) | A-2 | cis-2-Benzyloxycarbonylamino-cyclohexane carboxylic acid | Amino-(3,4-dimethoxy-phenyl)-acetonitrile; hydrochloride | 451.53 | 474 (MNa+) |
| 55 | cis-{2-[(R)-and (S)-(Cyano-phenyl-methyl-carbamoyl]-cyclohexyl}-carbamic acid 4-nitro-benzyl ester | B | cis-2-Amino-cyclohexanecarboxylic acid (cyano-phenyl-methyl)-amide; compound with trifluoro-acetic acid | 4-Nitrobenzyl chloroformate | 436.47 | 437 (MH+) |
| 56 | cis-(2-{[(R) and (S)-Cyano-(3,4-dimethoxy-phenyl)-methyl]-carbamoyl}-cyclohexyl)-carbamic acid 4-nitro-benzyl ester | B | cis-2-Amino-cyclohexanecarboxylic acid [cyano-(3,4-dimethoxy-phenyl)-methyl]-amide; compound with trifluoro-acetic acid | 4-Nitrobenzyl chloroformate | 496.52 | 497 (MH+) |
| 57 | cis-2-(3-Phenyl-propionylamino)-cyclohexanecarboxylic acid [(R)-and (S)-cyano-(3,4-dimethoxy-phenyl)-methyl]-amide | B | cis-2-Amino-cyclohexanecarboxylic acid [cyano-(3,4-dimethoxy-phenyl)-methyl]-amide; compound with trifluoro-acetic acid | 3-Phenylpropionyl chloride | 449.55 | 450 (MH+) |
| 58 | cis-2-(Cyclopropanecarbonyl-amino)-cyclohexanecarboxylic acid [(R)-and (S)-cyano-(3,4-dimethoxy-phenyl)-methyl]-amide | B | cis-2-Amino-cyclohexanecarboxylic acid [cyano-(3,4-dimethoxy-phenyl)-methyl]-amide; compound with trifluoro-acetic acid | Cyclopropanecarbonyl chloride | 385.46 | 386 (MH+) |
| 59 | cis-{2-[(R)-and (S)-(Cyano-phenyl-methyl-carbamoyl]-cyclohexyl}-carbamic acid cyclopentyl ester | B | cis-2-Amino-cyclohexanecarboxylic acid (cyano-phenyl-methyl)-amide; compound with trifluoro-acetic acid | Cyclopentyl chloroformate | 369.46 | 370 (MH+) |
| 60 | trans-(2-{[Cyano-(3-hydroxy-phenyl)-methyl]-carbamoyl}-cyclohexyl)-carbamic acid 3-p-tolyl-propyl ester | D | trans-2-(3-p-Tolyl-propoxycarbonylamino)-cyclohexanecarbonylic acid | 2-Amino-2-(3-hydroxyphenyl)acetonitrile | 449.55 | 472 (MNa+) |
| | cis-[2-((R)-and (S)-1-Cyano-3-methyl-butylcarbamoyl)-cyclohexyl]-carbamic acid benzyl ester | A | cis-2-Benzyloxycarbonylamino-cyclohexane carboxylic acid | 2-Amino-4-methyl-pentanenitrile; hydrochloride | 371.48 | 394 (MNa+) |
| 62 | cis-2-(2-Phenoxy-acetylamino)-cyclohexanecarboxylic acid [(R)-and (S)-cyano-(3,4-dimethoxy-phenyl)-methyl]-amide | B | cis-2-Amino-cyclohexanecarboxylic acid [cyano-(3,4-dimethoxy-phenyl)-methyl]-amide; compound with trifluoro-acetic acid | Phenoxyacetyl chloride | 451.52 | 452 (MH+) |
| 63 | trans-2-(2-Phenoxy-acetylamino)-cyclohexanecarboxylic acid [cyano-(3-hydroxy-phenyl)-methyl]-amide | C | trans-2-(2-Phenoxy-acetylamino)-cyclohexanecarboxylic acid | Amino-(3-hydroxy-phenyl)-acetonitrile | 407.47 | 408 (MH+) |
| 64 | cis-(2-{(R)-and (S)-[Cyano-(2,4-dimethyl-phenyl)-methyl]-carbamoyl}-cyclohexyl)-carbamic acid benzyl ester | A | cis-2-Benzyloxycarbonylamino-cyclohexane carboxylic acid | Amino-(2,4-dimethyl-phenyl)-acetonitrile; hydrochloride | 419.52 | 420 (MH+) |
| 65 | cis-2-[2-(4-Chloro-phenoxy)-acetylamino]-cyclohexanecarboxylic acid [(R)-and (S)-cyano-(3,4-dimethoxy-phenyl)-methyl]-amide | B | cis-2-Amino-cyclohexanecarboxylic acid [cyano-(3,4-dimethoxy-phenyl)-methyl]-amide; compound with trifluoro-acetic acid | 4-Chlorophenoxyacetyl chloride | 485.97 | 486 (MH+) |
| 67 | cis-2-(2-Phenylsulfanyl-acetylamino)-cyclohexanecarboxylic acid ((R)-and (S)-cyano-phenyl-methyl-amide | B | cis-2-Amino-cyclohexanecarboxylic acid (cyano-phenyl-methyl)-amide; compound with trifluoro-acetic acid | (Phenylthio)acetyl chloride | 407.54 | 408 (MH+) |
| 68 | trans-(2-{[Cyano-(3-hydroxy-phenyl)-methyl]-carbamoyl}-cyclohexyl)-carbamic acid 3-(4-chloro-phenyl)-propyl ester | D | trans-2-[3-(4-Chloro-phenyl)-propoxycarbonylamino]-cyclohexanecarboxylic acid | 2-Amino-2-(3-hydroxyphenyl)acetonitrile | 469.97 | 470 (MH+) |
| 69 | cis-2-(2-Phenylsulfanyl-acetylamino)-cyclohexanecarboxylic acid [(R)-and (S)-cyano-(3,4-dimethoxy-phenyl)-methyl]-amide | B | cis-2-Amino-cyclohexanecarboxylic acid [cyano-(3,4-dimethoxy-phenyl)-methyl]-amide; compound with trifluoro-acetic acid | (Phenylthio)acetyl chloride | 467.59 | 468 (MH+) |
| 70 | trans-2-(Benzo[1,2,5]oxadiazole-4-sulfonylamino)-cyclohexanecarboxylic acid [cyano-(3-hydroxy-phenyl)-methyl]-amide | C | trans-2-(Benzo[1,2,5]oxadiazole-4-sulfonylamino)-cyclohexanecarboxylic acid | Amino-(3-hydroxy-phenyl)-acetonitrile | 455.49 | 478 (MNa+) |
| 71 | trans-N-(2-{[Cyano-(3-hydroxy-phenyl)-methyl]-carbamoyl}-cyclohexyl)-4-fluoro-benzamide | C | trans-2-(4-Fluoro-benzoylamino)-cyclohexanecarboxylic acid | Amino-(3-hydroxy-phenyl)-acetonitrile | 395.43 | 396 (MH+) |

| No. | Compound | Method | Educt 1 | Educt 2 | MW | MS |
|---|---|---|---|---|---|---|
| 72 | cis-2-[2-(4-Chloro-phenoxy-acetylamino]-cyclohexanecarboxylic acid ((R)-and (S)-cyano-phenyl-methyl-amide | B | cis-2-Amino-cyclohexanecarboxylic acid (cyano-phenyl-methyl)-amide; compound with trifluoro-acetic acid | 4-Chlorophenoxyacetyl chloride | 425.91 | 426 (MH+) |
| 73 | cis-2-(3-Phenyl-propionylamino)-cyclohexanecarboxylic acid (cyano-phenyl-methyl)-amide | A-2 | cis-2-Benzyloxycarbonylamino-cyclohexane carboxylic acid | Amino-phenyl-acetonitrile; hydrochloride | 389.5 | 390 (MH+) |
| 74 | cis-2-Phenylacetylamino-cyclohexanecarboxylic acid [(R)-and (S)-cyano-(3,4-dimethoxy-phenyl)-methyl]-amide | B | cis-2-Amino-cyclohexanecarboxylic acid [cyano-(3,4-dimethoxy-phenyl)-methyl]-amide; compound with trifluoro-acetic acid | Phenylacetyl chloride | 435.52 | 436 (MH+) |
| 75 | cis-2-Phenylmethanesulfonylamino-cyclohexanecarboxylic acid [(R)-and {S)-cyano-(3,4-dimethoxy-phenyl)-methyl]-amide | B | cis-2-Amino-cyclohexanecarboxylic acid [cyano-(3,4-dimethoxy-phenyl)-methyl]-amide; compound with trifluoro-acetic acid | alpha-Toluenesulphonyl chloride | 471.58 | 489 (MNH4+) |
| 76 | trans-2-(2-Phenylsulfanyl-acetylamino)-cyclohexanecarboxylic acid [cyano-(3-hydroxy-phenyl)-methyl]-amide | C | trans-2-(2-Phenylsulfanyl-acetylamino)-cyclohexanecarboxylic acid | Amino-(3-hydroxy-phenyl)-acetonitrile | 423.53 | 424 (MH+) |
| 77 | cis-[2-((R)-and (S)-1-Cyano-hexylcarbamoyl)-cyclohexyl]-carbamic acid benzyl ester | A | cis-2-Benzyloxycarbonylamino-cydohexane carboxylic acid | 2-Amino-heptanenitrile; hydrochloride | 385.51 | 386 (MH+) |
| 78 | cis-2-(2-Phenoxy-acetylamino)-cyclohexanecarboxylic acid ((R)-and (S)-cyano-phenyl-methyl-amide | B | cis-2-Amino-cydohexanecarboxylic acid (cyano-phenyl-methyl)-amide; compound with trifluoro-acetic acid | Phenoxyacetyl chloride | 391.47 | 392 (MH+) |
| 79 | trans-Isoxazole-5-carboxylic acid (2-[cyano-(3-hydroxy-phenyl)-methyl]-carbamoyl)-cyclohexyl]-amide | C | trans-2- [(Isoxazole-5-carbonyl)-amino]-cyclohexanecarboxylic acid | Amino-(3 -hydroxy-phenyl)-acetonitrile | 368.39 | 368 (MH+) |
| 80 | cis-2-(3-Cyclohexylcarbonylamino)-cyclohexanecarboxylic acid [(R)-and (S)-cyano-(3,4-dimethoxy-phenyl)-methyl]-amide | B | cis-2-Amino-cyclohexanecarboxylic acid [cyano-(3,4-dimethoxy-phenyl)-methyl]-amide; compound with trifluoro-acetic acid | Cyclohexanecarboxy-licacid chloride | 427.54 | 428 (MH+) |
| 81 | (2-{[Cyano-(3-hydroxy-phenyl)-methyl]-carbamoyl}-cyclohexyl)-carbamic acid 4-trifluoromethyl-benzyl ester | D | 2-(4-Trifluoromethyl-benzyloxycarbonylamino)-cyclohexanecarboxylic acid | 2-Amino-2-(3-hydroxyphenyl) acetonitrile | 475.47 | 476 (MH+) |
| 82 | cis-2-(Cyclobutanecarbonyl-amino)-cyclohexanecarboxylic acid [(R)-and (S)-cyano-(3,4-dimethoxy-phenyl)-methyl]-amide | B | cis-2-Amino-cyclohexanecarboxylic acid [cyano-(3,4-dimethoxy-phenyl)-methyl]-amide; compound with trifluoro-acetic acid | Cyclobutanecarbonyl chloride | 399.49 | 400 (MH+) |
| 83 | cis-2- [2-(4-Chloro-phenyl-acetylamino]-cyclohexanecarboxylic acid ((R)-and (S)-cyano-phenyl-methyl-amide | B | cis-2-Amino-cyclohexanecarboxylic acid (cyano-phenyl-methyl)-amide; compound with trifluoro-acetic acid | 4-Chlorophenylacetyl chloride | 409.92 | 410 (MH+) |
| 84 | cis-2-(Cyclopentanecarbonyl-amino-cyclohexanecarboxylic acid ((R)-and (S)-cyano-phenyl-methyl)-amide | B | cis-2-Amino-cyclohexanecarboxylic acid (cyano-phenyl-methyl)-amide; compound with trifluoro-acetic acid | Cyclopentanecarbonyl chloride | 353.46 | 354 (MH+) |
| 85 | cis-2-[2-(4-Chloro-phenyl)-acetylamino]-cyclohexanecarboxylic acid [(R)-and (S)-cyano-(3,4-dimethoxy-phenyl)-methyl]-amide | B | cis-2-Amino-cyclohexanecarboxylic acid [cyano-(3,4-dimethoxy-phenyl)-methyl]-amide; compound with trifluoro-acetic acid | 4-Chlorophenylacetic acid chloride | 469.97 | 470 (MH+) |
| 86 | (1S,2R)-{2-(R)-and (S)-[(Cyano-phenyl-methyl)-carbamoyl]-cyclohexyl}-carbamic acid benzyl ester | A-2 | (1S,2R)-2-Benzyloxycarbonylamino-cyclohexane carboxylic acid | Amino-phenyl-acetonitrile; hydrochloride | 391.47 | 390 (M-H) |
| 87 | (1 S,2R)-(2-(R)-and (S)-{[Cyano-(3-niethoxy-phenyl)-methyl]-carbamoyl}-cyclohexyl)-carbamic acid benzyl ester | A-2 | (1S,2R)-2-Benzyloxycarbonylamino-cyclohexane carboxylic acid | Amino-(3-methoxy-phenyl)-acetonitrile; hydrochloride | 421.5 | 439 (MNH4+) |
| 88 | trans-N-(2-{[Cyano-(3-hydroxy-phenyl )-methyl]-carbamoyl}-cyclohexyl )-4-fluoro-benzamide | C | trans-2- [(Quinoxaline-2-carbonyl)-amino]-cyclohexanecarboxylic acid | Amino-(3-hydroxy-phenyl)-acetonitrile | 429.48 | 430 (MH+) |
| 89 | cis-2-(2-Benzyloxy-acetylamino)-cyclohexanecarboxylic acid [(R)-and (S)-cyano-(3,4-dimethoxy-phenyl)-methyl]-amide | B | cis-2-Amino-cyclohexanecarboxylic acid [cyano-(3,4-dimethoxy-phenyl)-methyl]-amide; compound with trifluoro-acetic acid | Benzyloxyacetyl chloride | 465.55 | 466 (MH+) |
| 90 | trans-2-(2-Thiophen-2-yl-acetylamino)-cyclohexanecarboxylic acid [cyano-(3-hydroxy-phenyl)-methyl]-amide | C | trans-2-(2-Thiophen-2-yl-acetylamino)-cyclohexanecarboxylic acid | Amino-(3-hydroxy-phenyl)-acetonitrile | 397.5 | 398 (MH+) |
| 91 | cis-[2-((R)-and (S)-1-Cyano-propylcarbamoyl)-cyclohexyl]-carbamic acid benzyl ester | A | cis-2-Benzyloxycarbonylamino-cyclohexane carboxylic acid hydrochloride | 2-Amino-butyronitrile; | 343.42 | 344 (MH+) |
| 92 | cis-2-Phenylacetylamino-cyclohexanecarboxylic acid ((R)-and (S)-cyano-phenyl-methyl)-amide | B | cis-2-Amino-cyclohexanecarboxylic acid (cyano-phenyl-methyl)-amide; compound with trifluoro-acetic acid | Phenylacetyl chloride | 375.47 | 376 (MH+)<br>398 (MNa+) |
| 93 | cis-2-(2- Benzyloxy-acetylamino)-cyclohexanecarboxylic acid ((R)-and (S)-cyano-phenyl-methyl)-amide | B | cis-2-Amino-cyclohexanecarboxylic acid (cyano-phenyl-methyl)-amide; compound with trifluoro-acetic acid | Benzyloxyacetyl chloride | 405.5 | 406 (MH+) |

-continued

| No. | Compound | Method | Educt 1 | Educt 2 | MW | MS |
|---|---|---|---|---|---|---|
| 94 | cis-2-(Cyclopropanecarbonyl-amino-cyclohexanecarboxylic acid ((R)-and (S)-cyano-phenyl-methyl-amide | B | cis-2-Amino-cyclohexanecarboxylic acid (cyano-phenyl-methyl)-amide; compound with trifluoro-acetic acid | Cyclopropanecarbonyl chloride | 325.41 | 326 (MH+) |
| 95 | cis-2-(3-Cyclopentyl-propionylamino-cyclohexanecarboxylic acid ((R)-and (S)-cyano-phenyl-methyl-amide | B | cis-2-Amino-cyclohexanecarboxylic acid (cyano-phenyl-methyl)-amide; compound with trifluoro-acetic acid | Cyclopentyl-propionyl chloride | 381.52 | 382 (MH+) |
| 96 | cis-2-(Cyclopentanecarbonyl-amino)-cyclohexanecarboxylic acid [(R)-and (S)-cyano-(3,4-dimethoxy-phenyl)-methyl]-amide | B | cis-2-Amino-cyclohexanecarboxylic acid (cyano-phenyl-methyl)-amide; compound with trifluoro-acetic acid | Cyclopentanecarbonyl chloride | 413.52 | 414 (MH+) |
| 97 | trans-Thiopllene-2-carb()xylic acid (2-[cyano-(3-hydroxy-phenyl)-methyl]-carbamoyl]-cyclohexyl)-amide | C | trans-2-[(Thiophene-2-carbonyl)-amino]-cyclohexanecarboxylic acid | Amino-(3-hydroxy-phenyl)-acetonitrile | 383.47 | 384 (MH+) |
| 98 | cis-2-(3-Phenyl-propionylamino-cyclohexanecarboxylic acid ((R)-and (S)-cyano-phenyl-methyl-amide | B | cis-2-Amino-cyclohexanecarboxylic acid (cyano-phenyl-methyl)-amide; compound with trifluoro-acetic acid | 3-Phenylpropionyl chloride | 389.5 | 390 (MH+) |
| 99 | cis-2-Phenylmethanesulfonylamino-cydohexanecarboxylic acid ((R)-and (S)-cyano-phenyl-methyl-amide | B | cis-2-Amino-cyclohexanecarboxylic acid (cyano-phenyl-methyl)-amide; compound with trifluoro-acetic acid | alpha-Toluenesulphonyl chloride | 411.52 | 412 (MH+) 434 (MNa+) |
| 100 | trans-(2-{[Cyano-(3-methoxy-phenyl)-methyl]-carbamoyl}-cyclohexyl)-carbamic acid benzyl ester | A-2 | trans-2-Benzyloxycarbonylamino-cyclohexane carboxylic acid | Amino-(3-methoxy-phenyl)-acetonitrile; hydrochloride | 421.5 | 439 (MNH4+) |
| 101 | cis-2-(4-Ethoxy-phenylamino)-cyclohexanecarboxylic acid [cyano-(3-hydroxy-phenyl)-methyl]-amide | E | 2-(4-Ethoxyphenylamino)-cyclohexane carboxylic acid | 2-Amino-2-(3-hydroxyphenyl)acetonitrile | 393.49 | 394 (MH+) |
| 102 | 2-(4-Ethoxy-phenylamino)-cyclohexanecarboxylic acid (cyano-phenyl-methyl)-amide | E | 2-(4-Ethoxyphenylamino)-cyclohexane carboxylic acid | Amino-phenyl-acetonitrile; hydrochloride | 377.49 | 378 (MH+) |
| 103 | cis-2-(4-Ethoxy-phenylamino)-cyclohexanecarboxylic acid [(3-bromo-phenyl)-cyano-methyl]-amide | E | 2-(4-Ethoxyphenylamino)-cydohexane carboxylic acid | Amino-(3-bromo-phenyl)-acetonitrile hydrochloride | 456.39 | 456 (MH+) |
| 104 | cis-2-(4-Ethoxy-phenylamino)-cyclohexanecarboxylic acid (benzo[1,3]dioxol-5-yl-cyano-methyl)-amide | E | 2-(4-Ethoxyphenylamino)-cyclohexane carboxylic acid | Amino-benzo[1,3]dioxol-5-yl-acetonitrile; hydrochloride | 421.5 | 422 (MH+) |
| 105 | cis-2-(4-Ethoxy-phenylamino)-cyclohexanecarboxylic acid cyano-(4-methoxy-phenyl)-methyl]-amide | E | 2-(4-Ethoxyphenylamino)-cyclohexane carboxylic acid | Amino-(4-methoxy-phenyl)-acetonitrile; hydrochloride | 407.52 | 408 (MH+) |
| 106 | cis-2-Phenylamino-cyclohexanecarboxylic acid (benzo[1,3]dioxol-5-yl-cyano-methyl)-amide | E | cis-2-Phenylamino-cyclohexane carboxylic acid | Amino-benzo[1,3]dioxol-5-yl-acetonitrile; hydrochloride | 377.45 | 378 (MH+) |
| 107 | 2-Phenylamino-cyclohexanecarboxylic acid (cyano-phenyl-methyl)-amide | E | cis-2-Phenylamino-cyclohexane carboxylic acid hydrochloride | Amino-phenyl-acetonitrile; | 333.44 | 334 (MH+) |
| 108 | cis-(2-{(R)-and (S)-[Cyano-(3,4-dimethoxy-phenyl)-methyl-carbamoyl}-cyclopentyl)-carbamic acid benzyl ester | A | cis-2-Benzyloxycarbonylamino-cyclopentane carboxylic acid acetonitrile; | Amino-(3,4-dimethoxy-phenyl)-hydrochloride | 437.49 | 438 (MH+) |
| 109 | trans-(2-{[(3-Chloro-phenyl-cyano-methyl]-carbamoyl}-cyclopentyl-carbamic acid benzyl ester | A | trans-2-Benzyloxycarbonylamino-cyclopentane carboxylic acid | Amino-(3-chloro-phenyl)-acetonitrile hydrochloride | 411.89 | 412 (MH+) |
| 110 | trans-(2-{[Cyano-(3-methoxy-phenyl)-methyl]-carbamoxyl}-cydopentyl)-carbamic acid benzyl ester | A | trans-2-Benzyloxycarbonylamino-cyclopentane carboxylic acid | Amino-(3-methoxy-phenyl)-acetonitrile; hydrochloride | 407.47 | 425 (MNH+) |
| 111 | trans-{2-[(Cyano-phenyl-methyl-carbamoyl]-cyclopentyl}-carbamic acid benzyl ester | A | trans-2-Benzyloxycarbonylamino-cyclopentane carboxylic acid | Amino-phenyl-acetonitrile; hydrochloride | 377.44 | 395 (MH+) |
| 112 | trans-{2-[(Cyano-m-tolyl-methyl-carbamoyl]-cyclopentyl}-carbamic acid benzyl ester | A | trans-2-Benzyloxycarbonylamino-cyclopentane carboxylic acid | Amino-m-tolyl-acetonitrile; hydrochloride | 391.47 | 492 (MH+) |
| 113 | Cis{2-[(Cyano-cyclopropyl-methyl)-carbamoyl]-cyclohexyl}-carbamic acid benzyl ester | A | Cis-2-Benzyloxycarbonylamino-cyclohexanecarboxylic acid | Amino-cyclopropyl-acetonitrile | 355.44 | 356 (M+H) |
| 114 | Cis-[2-(Cyanomethyl-carbamoyl)-cyclohexyl]-carbamic acid 2-chloro-benzyl ester | G | Cis-2-(9H-Fluoren-9-ylmethoxycarbonylamino)-cydohexanecarboxylic acid | Carbonic acid 2-chloro-benzyl ester 2,5-dioxo-pyrrolidin-1-yl ester | 349.82 | 351 (M+H) |
| 115 | Cis-[2-(Cyanomethyl-carbamoyl)-cyclohexyl]-carbamic acid 2-bromo-benzyl ester | G | Cis-2-(9H-Fluoren-9-ylmethoxycarbonylamino)-cydohexanecarboxylic acid | Carbonic acid 2-bromo-benzyl ester 2)5-dioxo-pyrrolidin-1-yl ester | 394.27 | 395 (M+H) |
| 116 | Cis-[2-(Cyanomethyl-carbamoyl)-cyclohexyl]-carbamic acid 3-nitro-benzyl ester | G | Cis-2-(9H-Fluoren-9-ylmethoxycarbonylamino)-cyclohexanecarboxylic acid | Carbonic acid 3-nitro-benzyl ester 2,5-dioxo-pyrrolidin-1-yl ester | 360.37 | 361 (M+H) |

-continued

| No. | Compound | Method | Educt 1 | Educt 2 | MW | MS |
|---|---|---|---|---|---|---|
| 117 | Cis-[4-(Cyanomethyl-carbamoyl)-cyclohexyl]-carbamic acid 4-chloro-benzyl ester | G | Cis-2-(9H-Fluoren-9-ylmethoxycarbonylamino)-cyclohexanecarboxylic acid | Carbonic acid 4-chloro-benzyl ester 2,5-dioxo-pyrrolidin-1-yl ester | 349.82 | 351 (M+H) |
| 118 | Cis-[4-(Cyanomethyl-carbamoyl)-cyclohexyl]-carbamic acid 3,4-dichloro-benzyl ester | G | Cis-2-(9H-Fluoren-9-ylmethoxycarbonylamino)-cyclohexanecarboxylic acid | Carbonic acid 3,4-dichloro-benzyl ester 2,5-dioxo-pyrrolidin-1-yl ester | 384.27 | 385 (M+H) |
| 119 | Cis-[4-(Cyanomethyl-carbamoyl)-cyclohexyl]-carbamic acid 3-chloro-benzyl ester | G | Cis-2-(9H-Fluoren-9-ylmethoxycarbonylamino)-cyclohexanecarboxylic acid | Carbonic acid 3-chloro-benzyl ester 2,5-dioxo-pyrrolidin-1-yl ester | 349.82 | 351 (M+H) |
| 120 | Trans-[4-(Cyanomethyl-carbamoyl)-cyclohexyl]-carbamic acid 2-chloro-benzyl ester | G | Trans-2-(9H-Fluoren-9-ylmethoxycarbonylamino)-cyclohexanecarboxylic acid | Carbonic acid 2-chloro-benzyl ester 2,5-dioxo-pyrrolidin-1-yl ester | 349.82 | 351 (M+H) |
| 121 | Trans-[4-(Cyanomethyl-carbamoyl)-cyclohexyl]-carbamic acid 2-bromo-benzyl ester | G | Trans-2-(9H-Fluoren-9-ylmethoxycarbonylamino)-cydohexanecarboxylic acid | Carbonic acid 2-bromo-benzyl ester 2,5-dioxo-pyrrolidin-1-yl ester | 394.27 | 395 (M+H) |
| 122 | Trans-[4-(Cyanomethyl-carbamoyl)-cyclohexyl]-carbamic acid 3-nitro-benzyl ester | G | Trans-2-(9H-Fluoren-9-ylmethoxycarbonylamino)-cyclohexanecarboxylic acid | Carbonic acid 3-nitro-benzyl ester 2,5-dioxo-pyrrolidin-1-yl ester | 360.37 | 361 (M+H) |
| 123 | Trans-[4-(Cyanomethyl-carbamoyl)-cyclohexyl]-carbamic acid phenyl ester | G | Trans-2-(9H-Fluoren-9-ylmethoxycarbonylamino)-cyclohexanecarboxylic acid | Carbonic acid phenyl ester 2,5-dioxo-pyrrolidin-1-yl ester | 301.35 | 302 (M+H) |
| 124 | Trans-[4-(Cyanomethyl-carbamoyl)-cyclohexyl]-carbamic acid 3,4-dichloro-benzyl ester | G | Trans-2-(9H-Fluoren-9-ylmethoxycarbonylamino)-cyclohexanecarboxylic acid | Carbonic acid 3,4-dichloro-benzyl ester 2,5-dioxo-pyrrolidin-1-yl ester | 384.27 | 385 (M+H) |
| 125 | Cis-5-Methoxy-benzofuran-2-carboxylic acid [2-(cyanomethyl-carbamoyl)-cyclohexyl]-amide | H | Cis-2-(9H-Fluoren-9-ylmethoxycarbonylamino)-cyclohexanecarboxylic acid | 5-Methoxy-benzofuran-2-carboxylic acid | 355.4 | 356 (M+H) |
| 126 | Trans-5-Methoxy-benzofuran-2-carboxylic acid [2-(cyanomethyl-carbamoyl)-cyclohexyl]-amide | H | Trans-2-(9H-Fluoren-9-ylmethoxycarbonylamino)-cyclohexanecarboxylic acid | 5-Methoxy-benzofuran-2-carboxylic acid | 355.4 | 356 (M+H) |
| 127 | Trans-N-[2-(Cyanomethyl-carbamoyl)-cyclohexyl]-2-chloro-4-fluoro-benzamide | H | Trans-2-(9H-Fluoren-9-ylmethoxycarbonylamino)-cydohexanecarboxylic acid | 2-chloro-4-fluoro-benzoic acid | 337.78 | 339 (M+H) |
| 128 | Trans-N-[2-(Cyanomethyl-carbamoyl)-cyclohexyl]-2-methoxy-3-methyl-benzamide | H | Trans-2-(9H-Fluoren-9-Ylmethoxycarbonylamino)-cydohexanecarboxylic acid | 2-Methoxy-3-methyl-benzoic acid | 329.4 | 330 (M+H) |
| 129 | Trans-N-[2-(Cyanomethyl-carbamoyl)-cyclohexyl]-2,6-dichloro-4-methoxy-benzamide | H | Trans-2-(9H-Fluoren-9-ylmethoxycarbonylamino)-cyclohexanecarboxylic acid | 2,6-dichloro-4-methoxy-benzoic acid | 368.27 | 369 (M+H) |
| 130 | Cis-N-[2-(Cyanomethyl-carbamoyl)-cyclohexyl]-3-fluoro-4-methyl-benzamide | H | Cis-2-(9H-Fluoren-9-ylmethoxycarbonylamino)-cyclohexanecarboxylic acid | 3-fluoro-4-methyl-benzoic acid | 317.37 | 318 (M+H) |
| 131 | Cis-N-[2-(Cyanomethyl-carbamoyl)-cyclohexyl]-3-chloro-4-methyl-benzamide | H | Cis-2-(9H-Fluoren-9-ylmethoxycarbonylamino)-cyclohexanecarboxylic acid | 3-chloro-4-methyl-benzoic acid | 333.82 | 335 (M+H) |
| 132 | Trans-N-[2-(Cyanomethyl-carbamoyl)-cyclohexyl]-3-bromo-4-methyl-benzamide | H | Trans-2-(9H-Fluoren-9-ylmethoxycarbonylamino)-cyclohexanecarboxylic acid | 3-bromo-4-methyl-benzoic acid | 378.27 | 379 (M+H) |
| 133 | Trans-N-[2-(Cyanomethyl-carbamoyl)-cyclohexyl]-4-cyanomethyl-benzamide | H | Trans-2-(9H-Fluoren-9-ylmethoxycarbonylamino)-cyclohexanecarboxylic acid | 4-cyanomethyl-benzoic acid | 324.39 | 325 (M+H) |
| 134 | Cis-N-[2-(Cyanomethyl-carbamoyl)-cyclohexyl]-3,5-di-trifluoromethyl-benzamide | H | Cis-2-(9H-Fluoren-9-ylmethoxycarbonylamino)-cydohexanecarboxylic acid | 3,5-di-trifluoromethyl-benzoic acid | 421.35 | 422 (M+H) |
| 135 | Cis-N-[2-(Cyanomethyl-carbamoyl)-cyclohexyl]-4-tert-butyl-benzamide | H | Cis-2-(9H-Fluoren-9-ylmethoxycarbonylamino)-cyclohexanecarbonylic acid | 4-tert-butyl-benzoic acid | 341.46 | 342 (M+H) |
| 136 | Cis-N-[2-(Cyanomethyl-carbamoyl)-cyclohexyl]-3-chloro-6-methoxy-benzamide | H | Cis-2-(9H-Fluoren-9-ylmethoxycarbonylamino)-cydohexanecarboxylic acid | 3-chloro-6-methoxy-benzoic acid | 349.82 | 351 (M+H) |
| 137 | Trans-N-[2-(Cyanomethyl-carbamoyl)-cyclohexyl]-3-chloro-6-methoxy-benzamide | H | Trans-2-(9H-Fluoren-9-ylmethoxycarbonylamino)-cyclohexanecarboxylic acid | 3-chloro-6-methoxy-benzoic acid | 349.82 | 351 (M+H) |
| 138 | Cis-N-[2-(Cyanomethyl-carbamoyl)-cyclohexyl]-3-chloro-benzamide | H | Cis-2-(9H-Fluoren-9-ylmethoxycarbonylamino)-cyclohexanecarboxylic acid | 3-chloro-benzoic acid | 319.79 | 321 (M+H) |
| 139 | Cis-N-[2-(Cyanomethyl-carbamoyl)-cyclohexyl]-3-acetylamino-benzamide | H | Cis-2-(9H-Fluoren-9-ylmethoxycarbonylamino)-cyclohexanecarboxylic acid | 3-Acetylamino-benzoic acid | 342.4 | 343 (M+H) |

| No. | Compound | Method | Educt 1 | Educt 2 | MW | MS |
|---|---|---|---|---|---|---|
| 140 | Trans-N-[2-(Cyanomethyl-carbamoyl)-cyclohexyl]-3-acetylamino-benzamide | H | Trans-2-(9H-Fluoren-9-ylmethoxycarbonylamino)-cyclohexanecarboxylic acid | 3-Acetylamino-benzoic acid | 342.4 | 343 (M+H) |
| 141 | Cis-N-[2-(Cyanomethyl-carbamoyl)-cyclohexyl]-4-acetylamino-benzamide | H | Cis-2-(9H-Fluoren-9-ylmethoxycarbonylamino)-cyclohexanecarboxylic acid | 4-Acetylamino-benzoic acid | 342.4 | 343 (M+H) |
| 142 | Trans-N-[2-(Cyanomethyl-carbamoyl)-cyclohexyl]-4-acetylamino-benzamide | H | Trans-2-(9H-Fluoren-9-ylmethoxycarbonylamino)-cyclohexanecarboxylic acid | 4-Acetylamino-benzoic acid | 342.4 | 343 (M+H) |
| 143 | Cis-N-[2-(Cyanomethyl-carbamoyl)-cyclohexyl]-4-acetyl-benzamide | H | Cis-2-(9H-Fluoren-9-ylmethoxycarbonylamino)-cyclohexanecarboxylic acid | 4-Acetyl-benzoic acid | 327.39 | 328 (M+H) |
| 144 | Trans-N-[2-(Cyanomethyl-carbamoyl)-cyclohexyl]-4-acetyl-benzamide | H | Trans-2-(9H-Fluoren-9-ylmethoxycarbonylamino)-cyclohexanecarboxylic acid | 4-Acetyl-benzoic acid | 327.39 | 328 (M+H) |
| 145 | Cis-N-[2-(Cyanomethyl-carbamoyl)-cydohexyl]-2-chloro-5-(methylthio)-benzamide | H | Cis-2-(9H-Fluoren-9-ylmethoxycarbonylamino)-cyclohexanecarboxylic acid | 2-chloro-5-(methlylthio)-benzoic acid | 365.88 | 367 (M+H) |
| 146 | Cis-N-[2-(Cyanomethyl-carbamoyl)-cyclohexyl]-2,3-dichloro-benzamide | H | Cis-2-(9H-Fluoren-9-ylmethoxycarbonylamino)-cyclohexanecarboxylic acid | 2,3-dichloro-benzoic acid | 354.24 | 355 (M+H) |
| 147 | Trans-N-[2-(Cyanomethyl-carbamoyl)-cyclohexyl]-2,3-dichloro-benzamide | H | Trans-2-(9H-Fluoren-9-ylmethoxycarbonylamino)-cyclohexanecarboxylic acid | 2,3-dichloro-benzoic acid | 354.24 | 355 (M+H) |
| 148 | Cis-N-[2-(Cyanomethyl-carbamoyl)-cyclohexyl]-2,4-dichloro-benzamide | H | Cis-2-(9H-Fluoren-9-ylmethoxycarbonylamino)-cyclohexanecarboxylic acid | 2,4-dichloro-benzoic acid | 354.24 | 355 (M+H) |
| 149 | Cis-N-[2-(Cyanomethyl-carbamoyl)-cyclohexyl]-2,5-dichloro-benzamide | H | Cis-2-(9H-Fluoren-9-ylmethoxycarbonylamino)-cyclohexanecarboxylic acid | 2,5-dichloro-benzoic acid | 354.24 | 355 (M+H) |
| 150 | Cis-N-[2-(Cyanomethyl-carbamoyl)-cyclohexyl]-2,6-dichloro-benzamide | H | Cis-2-(9H-Fluoren-9-ylmethoxycarbonylamino)-cyclohexanecarboxylic acid | 2,6-dichloro-benzoic acid | 354.24 | 355 (M+H) |
| 151 | Cis-N-[2-(Cyanomethyl-carbamoyl)-cyclohexyl]-3,4-dichloro-benzamide | H | Cis-2-(9H-Fluoren-9-ylmethoxycarbonylamino)-cyclohexanecarboxylic acid | 3,4-dichloro-benzoic acid | 354.24 | 355 (M+H) |
| 152 | Trans-N-[2-(Cyanomethyl-carbamoyl)-cyclohexyl]-3,4-dichloro-benzamide | H | Trans-2-(9H-Fluoren-9-ylmethoxycarbonylamino)-cyclohexanecarboxylic acid | 3,4-dichloro-benzoic acid | 354.24 | 355 (M+H) |
| 153 | Cis-N-[2-(Cyanomethyl-carbamoyl)-cyclohexyl]-3,4-dichloro-benzamide | H | Cis-2-(9H-Fluoren-9-ylmethoxycarbonylamino)-cyclohexanecarboxylic acid | 3,5-dichloro-benzoic acid | 354.24 | 355 (M+H) |
| 154 | Trans-N-[2-(Cyanomethyl-carbamoyl)-cyclohexyl]-3,5-dichloro-benzamide | H | Trans-2-(9H-Fluoren-9-ylmethoxycarbonylamino)-cyclohexanecarboxylic acid | 3,5-dichloro-benzoic acid | 354.24 | 355 (M+H) |
| 155 | Cis-2-{[(4-chlorophenyl)acetyl]amino}-N-[cyano(cyclopropyl) methyl cyclohexanecarboxamide | I | Cis-2-Amino-cyclohexanecarboxylic acid(1-cyano-1-cyclopropyl-methyl)-amide acetic acid salt | 4-Chlorophenyl-acetic acid | 373.89 | 375 (M+H) |
| 156 | Cis-N-[cyano(cyclopropyl) methyl]-2-{[3-(3-methoxyphenyl)propanoyl]amino}cyclohexanecarboxamide | I | Cis-2-Amino-cyclohexanecarboxylic acid(1-cyano-1-cyclopropyl-methyl)-amide acetic acid salt | 3-(3-Methoxyphenyl)-propionic acid | 383.49 | 384 (M+H) |
| 157 | Cis-N-[2-({[cyano(cyclopropyl)methyl]amino}carbonyl)cyclohexyl]-4-ethylbenzamide | I | Cis-2-Amino-cyclohexanecarboxylic acid(1-cyano-1-cyclopropyl-methyl)-amide acetic acid salt | 4-Ethylbenzoic acid | 353.47 | 354 (M+H) |
| 158 | Cis-N-[2-(t [cyano(cyclopropyl)methyl]amino}carbonyl)cyclohexyl]-4-ethoxybenzamide | I | Cis-2-Amino-cyclohexanecarboxylic acid(1-cyano-1-cyclopropyl-methyl)-amide acetic acid salt | 4-Ethoxybenzoic acid | 369.47 | 370 (M+H) |
| 159 | Cis-N-[2-({f cyano(cyclopropyl)methyl]amino}carbonyl)cyclohexyl]-4-methoxybenzamide | F | Cis-2-Amino-cyclohexanecarboxylic acid(1-cyano-1-cyclopropyl-methyl)-amide acetic acid salt | 4-Methoxybenzoyl chloride | 355.44 | 356 (M+H) |
| 160 | Trans-N-[2-({[cyano(cyclopropyl)methyl]amino}carbonyl)cyclohexyl]-4-methoxybenzamide | F | Trans-2-Amino-cyclohexanecarboxylic acid(1-cyano-1-cyclopropyl-methyl)-amide acetic acid salt | 4-Methoxybenzoyl chloride | 355.44 | 356 (M+H) |
| 161 | Trans-N-[2-({[cyano(cyclopropyl)methyl]amino}carbonyl)cyclohexyl]-4-ethylbenzamide | F | Trans-2-Amino-cyclohexanecarboxylic acid(1-cyano-1-cyclopropyl-methyl)-amide acetic acid salt | 4-Ethylbenzoyl chloride | 353.47 | 354 (M+H) |
| 162 | Cis-N-[2-({[cyano(cyclopropyl)methyl]amino}carbonyl)cyclohexyl]-3,4-difluorobenzamide | F | Cis-2-Amino-cyclohexanecarboxylic acid(1-cyano-1-cyclopropyl-methyl)-amide acetic acid salt | 3,4-Difluorobenzoyl chloride | 361.39 | 362 (M+H) |
| 163 | Cis-N-[2-({[cyano(cyclopropyl)methyl]amino}carbonyl)cyclohexyl]-4-cyanobenzamide | F | Cis-2-Amino-cyclohexanecarboxylic acid(1-cyano-1-cyclopropyl-methyl)-amide acetic acid salt | 4-Cyanobezoyl chloride | 350.42 | 351 (M+H) |

| No. | Compound | Method | Educt 1 | Educt 2 | MW | MS |
|---|---|---|---|---|---|---|
| 164 | Cis-N-[2-({[cyano(cyclopropyl)methyl]amino}carbonyl)cyclohexyl]-4-tert-butylbenzamide | F | Cis-2-Amino-cyclohexanecarboxylic acid(1-cyano-1-cyclopropyl-methyl)-amide acetic acid salt | 4-tert-Butylbenzoyl chloride | 381.52 | 383 (M+H) |
| 165 | Cis-N-[2-({[cyano(cyclopropyl)methyl]amino}carbonyl)cyclohexyl]-3,4,5-trimethoxybenzamide | F | Cis-2-Amino-cydohexanecarboxylic acid(1-cyano-1-cyclopropyl-methyl)-amide acetic acid salt | 3,4,5-Trimethoxy benzoyl chloride | 415.49 | 416 (M+H) |

The following methods were used:

Method A:

Coupling of protected amino acids with amino nitriles

A solution of 1eq cis-2-Benzyloxycarbonylamino-cyclohexane carboxylic acid, 7 eq N-methylmorpholin, 0.2 eq HOBT and 2.4 eq EDCI in 7 ml $CH_2Cl_2$ is added to 1.1–1.3 eq amino nitrile-HCl. After shaking overnight the reaction mixture is extracted with 1N HCl and the $CH_2Cl_2$ is evaporated. The compounds are purified by HPLC:

| column: | HP-CombiHT XDB-C18, 21.2 mmI.D. × 50 mm, Series No DN 1020 |
|---|---|
| method: | Flow: 40 ml/min |
| 0 min | 80% water, 20% acetonitrile |
| 0.2 min | 80% water, 20% acetonitrile |
| 3.5 min | 5% water, 95% acetonitrile |
| 4.7 min | 5% water, 95% acetonitrile |
| 4.8 min | 80% water, 20% acetonitrile |
| 4.9 min | 80% water, 20% acetonitrile |
| machine: | Prep HPLC System Dynamax Model SD-1, UV-1 |

Method A-2:

The protected amino acid, the amino nitrile, TPTU (O-1,2-Dihydro-2-oxo-1-pyridyl)-N,N,N',N'-tetramethyluronium tetrafluoroborate) and Hünigsbase (N-Ethyldiisopropylamine) are dissolved in MeCN. The mixture is stirred at RT for 6–16 h. The solution is concentrated and the residue is dissolved in ethyl acetate and extracted with $H_2O$. The $H_2O$ layers are extracted with ethyl acetate. The combined ethyl acetate layers are washed with $NaHCO_3$, brine, dried over $Na_2SO_4$ and evaporated. The crude product is purified by column chromatography.

Yield 60–90%

Method B:

Crude mixture of amino acid-amide-trifluoroacetate (educt 1)+a. Carbonylchloride (educt 2) or b. sulfonylchloride (educt 2)+triethylamine To a solution of 1 eq 2-Amino-cyclohexanecarboxylic acid amide; compound with trifluoro-acetic acid (educt 1) in $CH_2Cl_2$ is added a solution of 1.1 eq carbonylchloride (educt 2) or sulfonylchloride (educt 2) or isothiocyanate (educt 2) in $CH_2Cl_2$. To this mixture is added 2.1 eq triethylamine. After shaking overnight at RT formic acid is added, $CH_2Cl_2$ is evaporated and the compound purified by HPLC:

| column: | HP-CombiHT XDB-C18, 21.2 mmI.D. × 50 mm, Series No DN 1020 |
|---|---|
| method: | Flow: 40 ml/min |
| 0 min | 80% water, 20% acetonitrile |
| 0.2 min | 80% water, 20% acetonitrile |
| 3.5 min | 5% water, 95% acetonitrile |
| 4.7 min | 5% water, 95% acetonitrile |
| 4.8 min | 80% water, 20% acetonitrile |
| 4.9 min | 80% water, 20% acetonitrile |
| machine: | Prep HPLC System Dynamax Model SD-1, UV-1 |

Method C:

The trans-cyclohexane carboxylic acid (educt1, 1 equiv) is dissolved in dry $CH_3CN$ (0.2M). A solution of TPTU (1 equiv), DIPEA (4 equiv) in dry $CH_3CN$ (0.2M) is added to the solution at rt. The amino-(3-hydroxy-phenyl)-acetonitrile (educt 2, 1 equiv) dissolved in $CH_3CN$ (0.2M) is added and the mixture is stirred overnight. The reaction mixture is filtered and concentrated. The residue is dissolved in 1 mL of $CH_3CN$ and purified by HPLC.

| column: | YMC; CombiPrep ODS_AQ; 50*20 mmI.D; S-5 um, 120A |
|---|---|
| method: | Flow: 40 ml/min |
| 0 min | 90% water, 10% acetonitrile |
| 0.1 L | 90% water, 10% acetonitrile |
| 3.5 min | 5% water, 95% acetonitrile |
| 5.5 min | 5% water, 95% acetonitrile |
| 5.7 min | 80% water, 20% acetonitrile |
| 5.8 min | 80% water, 20% acetonitrile |
| machine: | Prep HPLC System Dynamax Model SD-1, UV-1. |

Method D:

The reaction can be conveniently carried out by dissolving the trans-amino carbonyloxy-cyclohexane carboxylic acid (educt 1) in DMPF and adding TPTU (1 equiv), Hunigsbase (4 equiv), the 2-Amino-2-(3-hydroxy-phenyl)-acetonitrile (educt 2, 1 equiv) in DMF and stirring the mixture at room temperature for 16 hours. The reaction mixture can be filtered and the product can be obtained by HPLC.

| column: | YMC; CombiPrep ODS_AQ; 50*20 mmI.D; S-5 um, 120A |
|---|---|
| method: | Flow: 40 ml/min |
| 0 min | 90% water, 10% acetonitrile |
| 0.1 L | 90% water, 10% acetonitrile |
| 3.5 min | 5% water, 95% acetonitrile |
| 5.5 min | 5% water, 95% acetonitrile |
| 5.7 min | 80% water, 20% acetonitrile |
| 5.8 min | 80% water, 20% acetonitrile |
| machine: | Prep HPLC System Dynamax Model SD-1, UV-1. |

Conveniently, the trans-amino carbonyloxy-cyclohexane carboxylic acid (educt 1) is obtained by adding the mixed carbonate in THF (prepared from the corresponding alcohol, 4-Nitrophenylchloroformate and pyridine in $CH_2Cl_2$) to the corresponding amino acid dissolved in aqueous 10% $NaHCO_3$. The reaction mixture is vigorously stirred at room temperature for 16 hours. After completion of the reaction, the resulting compound is isolated by methods known to the person skilled in the art, e.g. by extraction.

Method E:

A solution of 2-Phenylamino-cyclohexane carboxylic acid (educt 1, 1 eq), 3 eq N-ethyldiisopropylamine and 1 eq TPTU in acetonitrile is added to 1 eq Amino-phenyl-acetonitrile hydrochloride (educt 2). After stirring overnight the solvent is evaporated. The residue is dissolved in ethyl acetate, washed with sodium hydrogencarbonate solution (3×) and brine. The solution is dried over sodium sulfate and evaporated. The compound is purified by flash chromatography (silicagel).

Method F:

DIPEA (diisopropylethylamine) (3 equivalents) is added to a solution of 2-Amino-cyclohexanecarboxylic acid(1-cyano-1-cyclopropyl-methyl)-amide acetic acid salt (1 equivalent) in $CH_2Cl_2$ (anhydrous, 5 ml) and the mixture is stirred at room temperature for 45 minutes. The acid chloride (1 equivalent) is added and the reaction mixture is stirred at room temperature under $N_2$ overnight. The reaction mixture is diluted with $CH_2Cl_2$, washed with 1N aqueous HCl and saturated $NaHCO_3$, dried over $MgSO_4$, filtered and concentrated. The residue is purified by preparative TLC (silica; hexane: EtOAc 1:1) to give the product as a white solid. Yield: 60–85%.

Method G:

To 1 eq of Rink resin bound glycine in DMF is added 3 eq. of Educt 1, 3 eq. EDCI, 1 eq. HOBT, and 9 eq. NMM. The reaction is shaken overnight at RT. The solvent is removed and the resin washed three times with dichloromethane, 3 times with methanol, and again three times with dichloromethane. The resin is then suspended in DMF and 20% piperidine is added. After 30 minutes reaction time at RT, the solvent is removed by filtration. The resin is washed three times with dichloromethane, 3 times with methanol, and again three times with dichloromethane. The resin is again suspended in DMF and 3 eq. of the succinimidyl carbonate (educt 2) is added. The reaction is shaken overnight at RT. The resin is then filtered and washed three times with dichloromethane, 3 times with methanol, and again three times with dichloromethane. The resin is then suspended in a 10% solution of trifluoroacetic acid in dichloromethane. After 30 minutes reaction time at room temperature, the resin is filtered and washed once with dichloromethane. The filtrate is concentrated to dryness to yield the amide. The amide is subjected to dehydration using Burgess reagent. The amide is diluted in dichloromethane or in the trans case 1,4-dioxane. One eq. of Burgess is added and the reaction stirred for 2 h at RT, after which a second eq. of Burgess is added and the reaction stirred for an additional 2 h. The crude reaction mixture is evaporated to dryness and then diluted in ethyl acetate. The organic layer is washed with 10% bicarbanate solution, water, and brine. The organic layer is then dryed, filtered and evaporated to dryness. When purification is necessary, it is carried out using HPLC.

| Shimadzu HPLC Pump Initial Conditions | |
|---|---|
| A % | 80, (H2O (0.1 TFA)) |
| B % | 20, (CH3CN) |
| Flow (mL/min): | 2.500 |
| Stop time (mins): | 10.0 |
| High pressure (psi): | 4000 |
| Low Pressure (psi): | 0 |
| Set Temp (C): | 40 |
| Temperature Limit (C): | 45 |

Shimadzu HPLC Pump Gradient Timetable

The gradient timetable contains 5 entries which are:

Time, A%, B%, Flow, Curve 1.00, 80, 20, 2.50, 6

3.00, 65, 35, 2.50, 6

5.00, 45, 55, 2.50, 6

7.00, 75, 25, 2.50, 6

10.00, 80, 20, 2.50, 6

Method H:

To 1 eq of Rink resin bound glycine in DMF is added 3 eq. of Educt 1, 3 eq. EDCI, 1 eq. HOBT, and 9 eq. NMM. The reaction is shaken overnight at RT. The solvent is removed and the resin washed three times with dichloromethane, 3 times with methanol, and again three times with dichloromethane. The resin is then suspended in DMF and 20% piperidine is added. After 30 minutes reaction time at RT, the solvent is removed by filtration. The resin is washed three times with dichloromethane, 3 times with methanol, and again three times with dichloromethane. The resin is again suspended in DMF and 3 eq. of the carboxylic acid (educt 2) is added, along with 3 eq. EDCI, 1 eq. HOBT, and 9 eq. NMM. The reaction is shaken overnight at RT. The resin is then filtered and washed three times with dichloromethane, 3 times with methanol, and again three times with dichloromethane. The resin is then suspended in a 10% solution of trifluoroacetic acid in dichloromethane. After 30 minutes reaction time at RT, the resin is filtered and washed once with dichloromethane. The filtrate is concentrated to dryness to yield the amide. The amide is subjected to dehydration using Burgess reagent. The amide is diluted in dichloromethane or in the trans case 1,4-dioxane. One eq. of Burgess is added and the reaction stirred for 2 h at RT, after which a second eq. Of Burgess is added and the reaction stirred for an additional 2 h. The crude reaction mixture is evaporated to dryness and then diluted in ethyl acetate. The organic layer is washed with 10% bicarbanate solution, water, and brine. The organic layer is then dryed, filtered and evaporated to dryness. When purification is necessary, it is carried out using HPLC.

Method I

HOBT (2 equivalents) is added to the solution of the acid (educt 2, 1 equivalent) in DMF (anhydrous, 5 ml) and the mixture is stirred at room temperature for 1 hour. 2-amino-cyclohexanecarboxylic acid(1-cyano-1-cyclopropyl-methyl)-amide acetic acid salt (1 equivalent), EDCI (2 equivalents) and NMM (6 equivalents) are added and the mixture is stirred at room temperature under $N_2$ overnight and concentrated. The residue is dissolved in $CH_2Cl_2$, washed with dilute aqueous HCl and saturated $NaHCO_3$, dried over $MgSO_4$, filtered and concentrated. The residue is purified by preparative TLC (silica; hexane: EtOAc 2:1) to give the product as a white solid. Yield: 65–85%.

EXAMPLE 9

Preparation of 2-Amino-2-cyclopropyl-acetonitrile Hydrochloride

Sodium cyanide (3.5 g, 71.4 mmol) and ammonium chlorid (3.82 g, 71.4 mmol) are dissolved in $H_2O$ (20 ml) and MeOH (20 ml) and the solution is cooled to 0° C. A solution of cyclopropanecarboxaldehyde (5.0 g, 71.3 mmol) in MeOH (15 ml) and $CH_2Cl_2$ (15 ml) is added dropwise to the above cooled mixture over 20 minutes. The mixture is stirred at 0° C. for 30 minutes and ammonium hydroxide (28% $NH_3$ in $H_2O$, 8.64 ml, 142.8 mmol) is added. The reaction mixture is allowed to warm to room temperature overnight and concentrated. The residue is partitioned between $H_2O$ and $CH_2Cl_2$. The organic layer is separated, dried over $MgSO_4$, filtered and concentrated to give a clear oil. This clear oil is dissolved in $Et_2O$ (50 ml) and 4N HCl in dioxane is added slowly. The white precipitate is filtered, washed with $Et_2O$, and dried in vacuo for 2 hours to give the product as a white powder. Yield: 7.89 g, 83.9%.

Preparation of {2-[(1-Cyano-1-cyclopropyl-methyl)-carbamoyl]-cyclohexyl}-carbamic Acid Benzyl Ester A solution of 2-Benzyloxycarbonyl-amino-cyclohexane carboxylic acid (1.46 g, 5.26 mmol), 2-Amino-2-cyclopropyl-acetonitrile hydrochloride (0.70 g, 5.27 mmol), 1-hydroxybenzotriazole (0.89 g, 5.82 mmol) and N-methylmorpholine (1.07 g, 10.58 mmol) in DMF is cooled to 0° C. and treated with 1-ethyl-3-(3-dimethylamino)propyl carbodiimide hydrochloride (2.02 g, 10.54 mmol). The reaction mixture is allowed to warm to room temperature overnight and concentrated. The residue is dissolved in $CH_2Cl_2$, washed with dilute aqueous HCl and saturated aqueous $NaHCO_3$, dried over $MgSO_4$, filtered and concentrated to give a brown oil. This brown oil is purified via flash chromatograhy with hexane:EtOAc 6:1 to 3:1 to give the product as a white foam.

Yield: 1.55 g, 82.8%.

Preparation of 2-Amino-cyclohexanecarboxylic Acid(1-Cyano-1-cyclopropyl-methyl)-amide Acetic Acid Salt To a solution of 2-[(1-cyano-1-cyclopropyl-methyl)-carbamoyl]-cyclohexyl-carbamic acid benzyl ester (0.15 g, 0.42 mmol) in 50 ml EtOAc with 1% HOAc (v/v) is added Pd/C (10%) (0.05 g) carefully under nitrogen. The mixture is degassed completely before the reaction flask is filled with $H_2$ through a balloon. The reaction mixture is stirred for 45 minutes. TLC showed that the starting material has disappeared. The reaction mixture is filtered through Celite. The filtrate is concentrated to give a yellow oil. Yield: 0.17 g, 100%. The isolated cis- and trans-forms of the product are obtained by starting from the corresponding cis- or trans-form of the cyclohexane derivative.

EXAMPLE 10

Preparation Cis-2-(9H-Fluoren-9-ylmethoxycarbonylamino)-cyclohexanecarboxylic Acid Cis Beta amino cyclohexane carboxylic acid (1 g, 7 mmol) is dissolved in 18 mL of a 10% solution of $NaCO_3$ in water. Dioxane (10.5 mL) is added and the solution is cooled in an ice bath. FMOC chloride (1.8 g, 7 mmol.) is added in portions and stirring is continued for 4 h in the ice bath. The reaction mixture is allowed to warm to room temperature overnight. The reaction is quenched by the addition of water to homogeneity. The aqueous layer is washed with ether twice and then acidified. The acidic layer is extracted with dichloromethane 3×100 mL. The combined organic layers are dried with sodium sulfate and the reaction mixture is condensed in vacuo. The solid material is purified using flash chromatography 1:1:0.16 hexanes:ethyl acetate:acetic acid. A 50% yield of pure material is obtained MS 366.2 (M+H).

Preparation Trans-2-(9H-Fluoren-9-ylmethoxycarbonylamino)-cyclohexanecarboxylic Acid Trans beta amino cyclohexane carboxylic acid (1 g, 7 mmol) is dissolved in 18 mL of a 10% solution of $NaCO_3$ in water. Dioxane (10.5 mL) is added and the solution is cooled in an ice bath. FMOC chloride (1.8 g, 7 mmol.) is added in portions and stirring is continued for 4 h in the ice bath. The reaction mixture is allowed to warm to room temperature overnight. The reaction is quenched by the addition of water to homogeneity. The aqueous layer is washed with ether twice and then acidified. Upon acidification the desired material precipitates. The precipitate is filtered and washed and the white product is used without purification.

Example A

Tablets containing the following ingredients can be manufactured in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

Example C

Injection solutions can have the following composition:

| | |
| --- | --- |
| Compound of formula I | 3.0 mg |
| Gelatine | 150.0 mg |
| Phenol | 4.7 mg |
| Water for injection solutions | ad 1.0 ml |

What is claimed is:

1. A compound selected from the group consisting of compounds of formula (I)

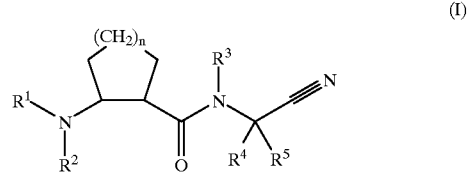

wherein
  $R^1$ is hydrogen, aryl, —CO—$R^a$ or —$SO_2$—$R^b$, wherein
    $R^a$ represents lower-alkyl, lower-alkoxy, cycloalkyl, cycloalkyl-lower-alkyl, cycloalkyl-lower-alkoxy, cycloalkyloxy, aryl, aryloxy, aryl-lower-alkyl, aryllower-alkoxy, aryloxy-lower-alkyl, aryl-S-lower-alkyl, aryl-lower-alkenyl, heteroaryl, heteroaryl-lower-alkyl, or heteroaryl-lower-alkoxy, and $R^b$ represents aryl, aryl-lower-alkyl, or heteroaryl, $R^2$ is hydrogen or lower-alkyl, $R^3$ is hydrogen or lower-alkyl, $R^4$ is hydrogen or lower-alkyl, $R^5$ is hydrogen, lower-alkyl, cycloalkyl, or aryl, and n is 1 or 2;

pharmaceutically acceptable salts of compounds of formula (I); and pharmaceutically acceptable esters of compounds of formula (I).

2. The compound of claim 1, wherein n is 1.

3. The compound of claim 2, wherein $R^2$ is H.

4. The compound of claim 3, wherein $R^3$ is H.

5. The compound of claim 4, wherein $R^4$ is H.

6. The compound of claim 5, wherein $R^1$ is —CO—$R^a$.

7. The compound of claim 6, wherein $R^a$ is selected from the group consisting of benzyloxy, phenylvinylene, thiophen-2-yl-methylene-oxy and thiophen-3-yl-methylene-oxy.

8. The compound of claim 7, wherein $R^a$ is benzyloxy.

9. The compound of claim 8, which is cis-(2-{(R)- and (S)-[cyano-(3,4-dimethoxy-phenyl)-methyl]-carbamoyl}-cyclopentyl)-carbamic acid benzyl ester.

10. The compound of claim 8, which is trans-(2-{[(3-chloro-phenyl-cyano-methyl]-carbamoyl}-cyclopentyl-carbamic acid benzyl ester.

11. The compound of claim 8, which is trans-(2-{[cyano-(3-methoxy-phenyl-methyl]-carbamoyl}-cyclopentyl-carbamic acid benzyl ester.

12. The compound of claim 8, which is trans-{2-[(cyano-phenyl-methyl-carbamoyl]-cyclopentyl}-carbamic acid benzyl ester.

13. The compound of claim 8, which is trans-{2-[(cyano-m-tolyl-methyl-carbamoyl]-cyclopentyl} -carbamic acid benzyl ester.

14. The compound of claim 5, wherein $R^5$ is aryl.

15. The compound of claim 14, wherein $R^5$ is selected from the group consisting of benzo[1,3]dioxyl, phenyl and napthyl, wherein the phenyl or napthyl is optionally substituted with lower-alkyl, halogen, hydroxy, lower-alkoxy or lower-alkyl-carbonyloxy.

16. The compound of claim 15, wherein $R^5$ is selected from the group consisting of phenyl,3-hydroxy-phenyl, 3-methoxy-phenyl, 4-methoxyl-phenyl, 3-methyl-phenyl, 2,4-dimethoxy-phenyl, 3,4-dimethoxy-phenyl, 3-chloro-phenyl, 3-bromo-phenyl, 4-bromo-phenyl and benzo[1,3] dioxol-5-yl.

17. The compound of claim 5, wherein $R^5$ is hydrogen.

18. The compound of claim 5, wherein $R^5$ is cycloalkyl.

19. The compound of claim 1, wherein n is 2.

20. The compound of claim 19, wherein $R^2$ is hydrogen.

21. The compound of claim 20, wherein $R^3$ is hydrogen.

22. The compound of claim 21, wherein $R^4$ is hydrogen.

23. The compound of claim 22, wherein $R^5$ is lower-alkyl.

24. The compound of claim 23, wherein $R^1$ is —CO—$R^a$.

25. The compound of claim 24, wherein $R^a$ is selected from the group consisting of benzyloxy, phenylvinylene, thiophen-2-yl-methylene-oxy and thiophen-3-yl-methylene-oxy.

26. The compound of claim 25, wherein $R^a$ is benzyloxy.

27. The compound of claim 26, which is cis-[2-((R)- and (S)-1-cyano-3-methyl-butylcarbamoyl)-cyclohexyl]-carbamic acid benzyl ester.

28. The compound of claim 26, which is cis-[2-((R)- and (S)-1-cyano-hexylcarbamoyl)-cyclohexyl]-carbamic acid benzyl ester.

29. The compound of claim 26, which is cis-[2-((R)- and (S)-1-cyano-propylcarbamoyl)-cyclohexyl]-carbamic acid benzyl ester.

30. The compound of claim 22, wherein $R^5$ is aryl.

31. The compound of claim 30, wherein $R^5$ is phenyl or naphthyl, optionally substituted with lower-alkyl, halogen, hydroxy, lower-alkoxy or lower-alkyl-carbonyloxy, or wherein $R^5$ represents benzo[1,3]dioxyl.

32. The compound of claim 31, wherein $R^5$ represents phenyl or naphthyl, optionally substituted with hydroxy, methoxy, methyl, acetoxy, chlorine or bromine or wherein $R^5$ represents benzo[1,3]dioxyl.

33. The compound of claim 32, wherein $R^5$ is napthyl optionally substituted with hydroxy, methoxy, methyl, acetoxy, chlorine or bromine.

34. The compound of claim 33, wherein $R^5$ is napthyl.

35. The compound of claim 34, which is cis-{2-[(R)- and (S)-(cyano-naphthalene-2-yl-methyl)-carbamoyl]-cyclohexyl}-carbamic acid benzyl ester.

36. The compound of claim 34, which is cis-{2-[(R)- and (S)-(cyano-naphthalene-1-yl-methyl)-carbamoyl]-cyclohexyl}-carbamic acid benzyl ester.

37. The compound of claim 32, wherein $R^5$ is phenyl optionally substituted with hydroxy, methoxy, methyl, acetoxy, chlorine or bromine.

38. The compound of claim 37, which is cis-(2-{(R)- and (S)-[(4-chloro-phenyl)-cyano-methyl]-carbamoyl}-cyclohexyl)-carbamic acid benzyl ester.

39. The compound of claim 37, which is cis-acetic acid 4-(R)-and (S)-[(2-benzyloxycarbonylamino-cyclohexanecarbonyl)-amino]-cyano-methyl}-phenyl ester.

40. The compound of claim 37, which is trans-(2-{[(3-bromo-4-methoxy-phenyl)-cyano-methyl]-carbamoyl}-cyclohexyl)-carbamic acid benzyl ester.

41. The compound of claim 37, which is trans-(2-{[(3-bromo-4-methoxy-phenyl)-cyano-methyl]-carbamoyl}-cyclohexyl)-carbamic acid benzyl ester.

42. The compound of claim 37, which is cis-(2-{(R)- and (S)-[cyano-(2,4-dimethyl-phenyl)-methyl]-carbamoyl}-cyclohexyl)-carbamic acid benzyl ester.

43. The compound of claim 32, wherein $R^5$ is selected from the group consisting of phenyl, 3-hydroxy-phenyl, 3-methoxy-phenyl, 4-methoxy-phenyl, 3-methyl-phenyl, 2,4-dimethoxy-phenyl, 3,4-dimethoxy-phenyl, 3-chloro-phenyl, 3-bromo-phenyl, 4-bromo-phenyl and benzo[1,3] dioxol-5-yl.

44. The compound of claim 43, wherein $R^5$ is phenyl.

45. The compound of claim 44, wherein $R^1$ is —CO—$R^a$.

46. The compound of claim 45, wherein $R^a$ is cycloalkyl, cycloalkyl-lower-alkyl, cycloalkyloxy, aryl, aryloxy, aryl-lower-alkyl, aryl-lower-alkoxy, aryloxy-lower-alkyl, aryl-S-lower-alkyl, aryl-lower-alkenyl, or heteroaryl-lower-alkoxy.

47. The compound of claim 46, which is cis-2-(2-phenylsulfanyl-acetylamino-cyclohexanecarboxylic acid ((R)- and (S)-cyano-phenyl-methyl-amide.

48. The compound of claim 46, which is cis-2-(3-cyclopentyl-propionylamino-cyclohexanecarboxylic acid ((R)- and (S)-cyano-phenyl-methyl-amide.

49. The compound of claim 46, wherein $R^a$ is cycloalkyl.

50. The compound of claim 49, which is cis-2-(cyclopentanecarbonyl-amino-cyclohexanecarboxylic acid ((R)- and (S)-cyano-phenyl-methyl-amide.

51. The compound of claim 49, which is cis-2-(cyclopropanecarbonyl-amino-cyclohexanecarboxylic acid ((R)- and (S)-cyano-phenyl-methyl-amide.

52. The compound of claim 46, wherein $R^a$ is aryl-lower-alkyl.

53. The compound of claim 52, which is cis-2-(3-phenyl-propionylamino)-cyclohexanecarboxylic acid (cyano-phenyl-methyl)-amide.

54. The compound of claim 52, which is cis-2-(3-phenyl-propionylamino-cyclohexanecarboxylic acid ((R)- and (S)-cyano-phenyl-methyl-amide.

55. The compound of claim 46, wherein $R^a$ is aryloxy-lower-alkyl.

56. The compound of claim 55, which is cis-2-[2-(4-chloro-phenoxy-acetylamino]-cyclohexanecarboxylic acid ((R)- and (S)-cyano-phenyl-methyl-amide.

57. The compound of claim 55, which is cis-2-(2-phenoxy-acetylamino-cyclohexanecarboxylic acid ((R)- and (S)-cyano-phenyl-methyl-amide.

58. The compound of claim 55, which is cis-2-(2-benzyloxy-acetylamino-cyclohexanecarboxylic acid ((R)- and (S)-cyano-phenyl-methyl-amide.

59. The compound of claim 46, wherein $R^a$ is phenyl optionally substituted with at least one group selected from phenyl, cyano, and fluoro; or $R^a$ is benzyloxy optionally substituted with at least one group selected from methyl, chloro, fluoro, methoxy, nitro, and $CF_3$; or $R^a$ is phenylvinylene, thiophenyl-methylene-oxy, cyclopentyloxy, thiophenyl-ethylene-oxy, naphthyloxy, thiophenyl-trimethylene-oxy, or phenoxy.

60. The compound of claim 59, which is cis-{2-[(R)- and (S)-(cyano-phenyl-methyl-carbamoyl]-cyclohexyl}-carbamic acid naphthalene-2-yl ester.

61. The compound of claim 59, which is cis-{2-[(R)- and (S)-(cyano-phenyl-methyl-carbamoyl]-cyclohexyl}-carbamic acid phenyl ester.

62. The compound of claim 59, which is cis-{2-[(R)- and (S)-(cyano-phenyl-methyl-carbamoyl]-cyclohexyl}-carbamic acid 4-nitro-benzyll ester.

63. The compound of claim 59, which is cis-{2-[(R)- and (S)-(cyano-phenyl-methyl-carbamoyl]-cyclohexyl}-carbamic acid cyclopentyl ester.

64. The compound of claim 59, wherein $R^a$ is benzyloxy, phenylvinylene, thiophen-2-yl-methylene-oxy, or thiophen-3-yl-methylene-oxy.

65. The compound of claim 64, which is cis-2-(3-phenyl-acryloylamino-cyclohexanecarboxylic acid ((R)- and (S)-cyano-phenyl-methyl-amide.

66. The compound of claim 64, wherein $R^a$ is benzyloxy.

67. The compound of claim 66, which is (R)-{2-[(S)-(cyano-phenyl-methyl)-(R)-carbamoyl]-cyclohexyl}-carbamic acid benzyl ester.

68. The compound of claim 66, which is syn-{2-[(S)-(cyano-phenyl-methyl)-carbamoyl]-cyclohexyl}-carbamic acid benzyl ester.

69. The compound of claim 66, which is cis-{2-[(cyano-phenyl-methyl)-carbamoyl]-cyclohexyl}-carbamic acid benzyl ester.

70. The compound of claim 66 which is trans-{2-[(cyano-phenyl-methyl)-carbamoyl]-cyclohexyl}-carbamic acid benzyl ester.

71. The compound of claim 66, which is (1S,2R)-{2-(R)- and (S)-[(cyano-phenyl-methyl)-carbamoyl]-cyclohexyl}-carbamic acid benzyl ester.

72. The compound of claim 46, wherein $R^a$ is benzyl optionally substituted with chloro, or phenyl optionally substituted with lower-alkyl, lower-alkoxy, or cyano.

73. The compound of claim 72, which is cis-N-{2-[(R)- and (S)-(cyano-phenyl-methyl-carbamoyl]-cyclohexyl}-benzamide.

74. The compound of claim 72, which is cis-2-[2-(4-chloro-phenyl-acetylamino]-cyclohexanecarboxylic acid ((R)- and (S)-cyano-phenyl-methyl-amide.

75. The compound of claim 72, which is cis-2-phenylacetylamino-cyclohexanecarboxylic acid ((R)- and (S)-cyano-phenyl-methyl-amide.

76. The compound of claim 72, wherein $R^a$ is 4-ethyl-phenyl, 4-methoxy-phenyl, 4-ethoxy-phenyl, 4-cyano-phenyl, 4-tert.-butyl-phenyl, or 4-chloro-benzyl.

77. The compound of claim 46, wherein $R^a$ is heteroaryl.

78. The compound of claim 46, wherein $R^a$ is 5-methoxy-benzofuran-2-yl.

79. The compound of claim 44, wherein $R^1$ is $—SO_2—R^b$.

80. The compound of claim 79, which is cis-2-phenylmethanesulfonylamino-cyclohexanecarboxylic acid ((R)- and (S)-cyano-phenyl-methyl-amide.

81. The compound of claim 44, wherein $R^1$ is phenyl, optionally substituted with ethoxy.

82. The compound of claim 81, which is 2-(4-ethoxy-phenylamino)-cyclohexanecarboxylic acid (cyano-phenyl-methyl)-amide.

83. The compound of claim 81, which is 2-phenylamino-cyclohexanecarboxylic acid (cyano-phenyl-methyl)-amide.

84. The compound of claim 43, wherein $R^5$ is 3-hydroxy-phenyl.

85. The compound of claim 84, wherein $R^1$ is $—CO—R^a$.

86. The compound of claim 85, which is trans-2-(2-thiophen-2-yl-acetylamino)-cyclohexanecarboxylic acid [cyano-(3-hydroxy-phenyl)-methyl]-amide.

87. The compound of claim 85, wherein $R^a$ is cycloalkyl, cycloalkyl-lower-alkyl, cycloalkyloxy, aryl, aryloxy, aryl-lower-alkyl, aryl-lower-alkoxy, aryloxy-lower-alkyl, aryl-S-lower-alkyl, aryl-lower-alkenyl, or heteroaryl-lower-alkoxy.

88. The compound of claim 87, which is trans-(2-{[cyano-(3-hydroxy-phenyl)-methyl]-carbamoyl}-cyclohexyl)-carbamic acid 3-thiophen-2-yl-propyl ester.

89. The compound of claim 87, which is trans-(2-{[cyano-(3-hydroxy-phenyl)-methyl]-carbamoyl}-cyclohexyl)-carbamic acid 3-p-tolyl-propyl ester.

90. The compound of claim 87, which is trans-(2-{[cyano-(3-hydroxy-phenyl)-methyl]-carbamoyl}-cyclohexyl)-carbamic acid 3-(4-chloro-phenyl)-propyl ester.

91. The compound of claim 87, which is trans-2-(2-phenylsulfanyl-acetylamino)-cyclohexanecarboxylic acid [cyano-(3-hydroxy-phenyl)-methyl]-amide.

92. The compound of claim 87, wherein $R^a$ is cycloalkyl.

93. The compound of claim 87, wherein $R^a$ is aryl-lower-alkyl.

94. The compound of claim 87, wherein $R^a$ is aryloxy-lower-alklyl.

95. The compound of claim 94, which is trans-2-(2-phenoxy-acetylamino)-cyclohexanecarboxylic acid [cyano-(3-hydroxy-phenyl)-methyl]-amide.

96. The compound of claim 87, wherein $R^a$ is phenyl optionally substituted with at least one group selected from phenyl, cyano and fluoro; or $R^a$ is benzyloxy optionally substituted with at least one group selected from methyl, chloro, fluoro, methoxy, nitro, and $CF_3$; or $R^a$ is phenylvinylene, thiophenyl-methylene-oxy, cyclopentyloxy, thiophenyl-ethylene-oxy, naphthyloxy, thiophenyl-trimethylene-oxy, or phenoxy.

97. The compound of claim 96 wherein $R^a$ is phenyl optionally substituted with at least one group selected from phenyl, cyano and fluoro.

98. The compound of claim 97, which is trans-N-(2-{[cyano-(3-hydroxy-phenyl)-methyl]-carbamoyl}-cyclohexyl)-4-fluoro-benzamide.

99. The compound of claim 96, wherein $R^a$ is benzyloxy optionally substituted with at least one group selected from methyl, chloro, fluoro, methoxy, nitro and $CF_3$.

100. The compound of claim 99, which is trans-(2-{[cyano-(3-hydroxy-phenyl)-methyl]-carbamoyl}-cyclohexyl)-carbamic acid 2-methyl-benzyl ester.

101. The compound of claim 99, which is trans-(2-{[cyano-(3-hydroxy-phenyl)-methyl]-carbamoyl}-cyclohexyl)-carbamic acid 2-chloro-benzyl ester.

102. The compound of claim 99, which is (2-{[cyano-(3-hydroxy-phenyl)-methyl]-carbamoyl}-cyclohexyl)-carbamic acid 4-fluoro-benzyl ester.

103. The compound of claim 99, which is trans-(2-{[cyano-(3-hydroxy-phenyl)-methyl]-carbamoyl}-cyclohexyl)-carbamic acid 2-methoxy-benzyl ester.

104. The compound of claim 99, which is trans-(2-{[cyano-(3-hydroxy-phenyl)-methyl]-carbamoyl}-cyclohexyl)-carbamic acid 3-chloro-benzyl ester.

105. The compound of claim 99, which is trans-(2-{[cyano-(3-hydroxy-phenyl)-methyl]-carbamoyl}-cyclohexyl)-carbamic acid 3-methyl-benzyl ester.

106. The compound of claim 99, which is trans-(2-{[cyano-(3-hydroxy-phenyl)-methyl]-carbamoyl}-cyclohexyl)-carbamic acid 3-methoxy-benzyl ester.

107. The compound of claim 99, which is trans-(2-{[cyano-(3-hydroxy-phenyl)-methyl]-carbamoyl}-cyclohexyl)-carbamic acid 4-methyl-benzyl ester.

108. The compound of claim 99, which is trans-(2-{[cyano-(3-hydroxy-phenyl)-methyl]-carbamoyl}-cyclohexyl)-carbamic acid 4-methoxy-benzyl ester.

109. The compound of claim 96, wherein $R^a$ is phenylvinylene, thiophenyl-methylene-oxy, cyclopentyloxy, thiophenyl-ethylene-oxy, naphthyloxy, thiophenyl-trimethylene-oxy, or phenoxy.

110. The compound of claim 109, which is trans-(2-{[cyano-(3-hydroxy-phenyl)-methyl]-carbamoyl}-cyclohexyl)-carbamic acid 2-thiophen-2-yl-ethyl ester.

111. The compound of claim 109, which is (2-{[cyano-(3-hydroxy-phenyl)-methyl]-carbamoyl}-cyclohexyl)-carbamic acid 4-trifluoromethyl-benzyl ester.

112. The compound of claim 96, wherein $R^a$ is benzyloxy, phenylvinylene, thiophen-2-yl-methylene-oxy, or thiophen-3-yl-methylene-oxy.

113. The compound of claim 112, which is (2-{[cyano-(3-hydroxy-phenyl)-methyl]-carbamoyl}-cyclohexyl)-carbamic acid thiophen-3-ylmethyl ester.

114. The compound of claim 112, which is trans-(2-{[cyano-(3-hydroxy-phenyl)-methyl]-carbamoyl}-cyclohexyl)-carbamic acid thiophen-2-ylmethyl ester.

115. The compound of claim 112, wherein $R^a$ is benzyloxy.

116. The compound of claim 115, which is (1R,2R)-(2-{(S)-[cyano-(3-hydroxy-phenyl)-methyl]-carbamoyl}-cyclohexyl)-carbamic acid benzyl ester.

117. The compound of claim 115, which is cis-(2-{[cyano-(3-hydroxy-phenyl)-methyl]-carbamoyl}-cyclohexyl)-carbamic acid benzyl ester.

118. The compound of claim 115, which is trans-(2-{[cyano-(3-hydroxy-phenyl)-methyl]-carbamoyl}-cyclohexyl)-carbamic acid benzyl ester.

119. The compound of claim 115, which is (1R,2R)-(2-{(R)-[cyano-(3-hydroxy-phenyl)-methyl]-carbamoyl}-cyclohexyl)-carbamic acid benzyl ester.

120. The compound of claim 87, wherein $R^a$ is benzyl optionally substituted with chloro, or phenyl optionally substituted with lower-alkyl, lower-alkoxy, or cyano.

121. The compound of claim 120, wherein $R^a$ is 4-ethyl-phenyl, 4-methoxy-phenyl, 4-ethoxy-phenyl, 4-cyano-phenyl, 4-tert.-butyl-phenyl, or 4-chloro-benzyl.

122. The compound of claim 121, which is trans-4-cyano-N-(2-{[cyano-(3-hydroxy-phenyl)-methyl]-carbamoyl}-cyclohexyl)-benzamide.

123. The compound of claim 121, which is cis-2-(4-ethoxy-phenylamino)-cyclohexanecarboxylic acid [cyano-(3-hydroxy-phenyl)-methyl]-amide.

124. The compound of claim 85, wherein $R^a$ is heteroaryl.

125. The compound of claim 124, which is trans-isoxazole-5-carboxylic acid (2-{[cyano-(3-hydroxy-phenyl)-methyl]-carbamoyl}-cyclohexyl)-amide.

126. The compound of claim 124 which is trans-thiophene-2-carboxylic acid (2-{[cyano-(3-hydroxy-phenyl)-methyl]-carbamoyl}-cyclohexyl)-amide.

127. The compound of claim 87, wherein $R^a$ is 5-methoxy-benzofuran-2-yl.

128. The compound of claim 84, wherein $R^1$ is —$SO_2$—$R^b$.

129. The compound of claim 128, which is trans-2-(4-chloro-benzenesulfonylamino)-cyclohexanecarboxylic acid [cyano-(3-hydroxy-phenyl)-methyl]-amide.

130. The compound of claim 128, which is trans-2-phenylmethanesulfonylamino-cyclohexanecarboxylic acid [cyano-(3-hydroxy-phenyl)-methyl]-amide.

131. The compound of claim 128, which is trans-2-(4-cyano-benzenesulfonylamino)-cyclohexanecarboxylic acid [cyano-(3-hydroxy-phenyl)-methyl]-amide.

132. The compound of claim 128, which is trans-2-(4-acetylamino-benzenesulfonylamino)-cyclohexanecarboxylic acid [cyano-(3-hydroxy-phenyl)-methyl]-amide.

133. The compound of claim 128, which is trans-2-(benzo[1,2,5]oxadiazole-4-sulfonylamino)-cyclohexanecarboxylic acid [cyano-(3-hydroxy-phenyl)-methyl]-amide.

134. The compound of claim 84, wherein $R^1$ is phenyl, optionally substituted with ethoxy.

135. The compound of claim 43, wherein $R^5$ is 3-methoxy-phenyl.

136. The compound of claim 135, which is cis-(2-{(R)- and (S)-[cyano-(3-methoxy-phenyl)-methyl]-carbamoyl}-cyclohexyl)-carbamic acid benzyl ester.

137. The compound of claim 135, which is (1S,2R)-(2-(R)- and (S)-{[cyano-(3-methoxy-phenyl)-methyl]-carbamoyl}-cyclohexyl)-carbamic acid benzyl ester.

138. The compound of claim 135, which is trans-(2-{[cyano-(3-methoxy-phenyl)-methyl]-carbamoyl}-cyclohexyl)-carbamic acid benzyl ester.

139. The compound of claim 43, wherein $R^5$ is 4-methoxy-phenyl.

140. The compound of claim 139, which is cis-(2-{(R)- and (S)-[cyano-(4-methoxy-phenyl)-methyl]-carbamoyl}-cyclohexyl)-carbamic acid benzyl ester.

141. The compound of claim 139, which is cis-2-(4-ethoxy-phenylamino)-cyclohexanecarboxylic acid [cyano-(4-methoxy-phenyl)-methyl]-amide.

142. The compound of claim 43, wherein $R^5$ is 3-methyl-phenyl.

143. The compound of claim 142, which is cis-{2-[(R)- and (S)-(cyano-m-tolyl-methyl)-carbamoyl]-cyclohexyl}-carbamic acid benzyl ester.

144. The compound of claim 43, wherein $R^5$ is 2,4-dimethoxy-phenyl.

145. The compound of claim 144, which is cis-(2-{(R)- and (S)-[cyano-(2,4-dimethoxy-phenyl)-methyl]-carbamoyl}-cyclohexyl)-carbamic acid benzyl ester.

146. The compound of claim 43, wherein $R^5$ is 3,4-dimethoxy-phenyl.

147. The compound of claim 146, wherein $R^1$ is —CO—$R^a$.

148. The compound of claim 147, which is cis-2-(2-benzyloxy-acetylamino)-cyclohexanecarboxylic acid [(R)- and (S)-cyano-(3,4-dimethoxy-phenyl)-methyl]-amide.

149. The compound of claim 147, wherein $R^a$ is cycloalkyl, cycloalkyl-lower-alkyl, cycloalkyloxy, aryl, aryloxy, aryl-lower-alkyl, aryl-lower-alkoxy, aryloxy-lower-alkyl, aryl-S-lower-alkyl, aryl-lower-alkenyl, or heteroaryl-lower-alkoxy.

150. The compound of claim 149, which is cis-2-(3-cyclopentyl-propionylamino)-cyclohexanecarboxylic acid [(R)- and (S)-cyano-(3,4-dimethoxy-phenyl)-methyl]-amide.

151. The compound of claim 149, which is cis-2-(2-phenylsulfanyl-acetylamino)-cyclohexanecarboxylic acid (R)- and (S)-cyano-(3,4-dimethoxy-phenyl)-methyl]-amide.

152. The compound of claim 149, wherein $R^a$ is cycloalkyl.

153. The compound of claim 152, which is cis-2-(cyclopropanecarbonyl-amino)-cyclohexanecarboxylic acid [(R)- and (S)-cyano-(3,4-dimethoxy-phenyl)-methyl]-amide.

154. The compound of claim 152, which is cis-2-(3-cyclohexylcarbonylamino)-cyclohexanecarboxylic acid [(R)- and (S)-cyano-(3,4-dimethoxy-phenyl)-methyl]-amide.

155. The compound of claim 152, which is cis-2-(cyclobutanecarbonyl-amino)-cyclohexanecarboxylic acid [(R)- and (S)-cyano-(3,4-dimethoxy-phenyl)-methyl]-amide.

156. The compound of claim 152, which is cis-2-(cyclopentanecarbonyl-amino)-cyclohexanecarboxylic acid [(R)- and (S)-cyano-(3,4-dimethoxy-phenyl)-methyl]-amide.

157. The compound of claim 149, wherein $R^a$ is aryl-lower-alkyl.

158. The compound of claim 157, which is cis-2-(3-phenyl-propionylamino)-cyclohexanecarboxylic acid [(R)- and (S)-cyano-(3,4-dimethoxy-phenyl)-methyl]-amide.

159. The compound of claim 149, wherein $R^a$ is aryloxy-lower-alkyl.

160. The compound of claim 159, which is cis-2-(2-phenoxy-acetylamino)-cyclohexanecarboxylic acid [(R)- and (S)-cyano-(3,4-dimethoxy-phenyl)-methyl]-amide.

161. The compound of claim 159, which is cis-2-[2-(4-chloro-phenoxy)-acetylamino]-cyclohexanecarboxylic acid [(R)- and (S)-cyano-(3,4-dimethoxy-phenyl)-methyl]-amide.

162. The compound of claim 149, wherein $R^a$ is phenyl optionally substituted with at least one group selected from phenyl, cyano, and fluoro; or $R^a$ is benzyloxy optionally substituted with at least one group selected from methyl, chloro, fluoro, methoxy, nitro, and $CF_3$; or $R^a$ is phenylvinylene, thiophenyl-methylene-oxy, cyclopentyloxy, thiophenyl-ethylene-oxy, naphthyloxy, thiophenyl-trimethylene-oxy, or phenoxy.

163. The compound of claim 162, which is cis-(2-{[(R)- and (S)-cyano-(3,4-dimethoxy-phenyl)-methyl]-carbamoyl}-cyclohexyl)-carbamic acid cyclopentyl ester.

164. The compound of claim 162, which is cis-biphenyl-4-carboxylic acid (2-{[(R)- and (S)-cyano-(3,4-dimethoxy-phenyl)-methyl]-carbamoyl}-cyclohexyl)-amide.

165. The compound of claim 162, which is cis-(2-{[(R)- and (S)-cyano-(3,4-dimethoxy-phenyl)-methyl]-carbamoyl}-cyclohexyl)-carbamic acid 4-nitro-benzyl ester.

166. The compound of claim 162, wherein $R^a$ is benzyloxy, phenylvinylene, thiophen-2-yl-methylene-oxy, or thiophen-3-yl-methylene-oxy.

167. The compound of claim 166, which is cis-2-(3-phenyl-acryloylamino)-cyclohexanecarboxylic acid [(R)- and (S)-cyano-(3,4-dimethoxy-phenyl)-methyl]-amide.

168. The compound of claim 166, wherein $R^a$ is benzyloxy.

169. The compound of claim 168, which is (2-{[cyano-(3,4-dimethoxy-phenyl)-methyl]-carbamoyl}-cyclohexyl)-carbamic acid benzyl ester (1 cis-racemate).

170. The compound of claim 168, which is (2-{[cyano-(3,4-dimethoxy-phenyl)-methyl]-carbamoyl}-cyclohexyl)-carbamic acid benzyl ester (1 cis-racemate).

171. The compound of claim 149, wherein $R^a$ is benzyl optionally substituted with chloro, or phenyl optionally substituted with lower-alkyl, lower-alkoxy, or cyano.

172. The compound of claim 171, which is cis-2-phenylacetylamino-cyclohexanecarboxylic acid [(R)- and (S)-cyano-(3,4-dimethoxy-phenyl)-methyl]-amide.

173. The compound of claim 171, which is cis-2-[2-(4-chloro-phenyl)-acetylamino]-cyclohexanecarboxylic acid [(R)- and (S)-cyano-(3,4-dimethoxy-phenyl)-methyl]-amide.

174. The compound of claim 171, wherein $R^a$ is 4-ethyl-phenyl, 4-methoxy-phenyl, 4-ethoxy-phenyl, 4-cyano-phenyl, 4-tert.-butyl-phenyl, or 4-chloro-benzyl.

175. The compound of claim 147, wherein $R^a$ is heteroaryl.

176. The compound of claim 175, wherein $R^a$ is 5-methoxy-benzofuran-2-yl.

177. The compound of claim 146, wherein $R^1$ is —$SO_2$—$R^b$.

178. The compound of claim 177, which is cis-2-phenylmethanesulfonylamino-cyclohexanecarboxylic acid [(R)- and (S)-cyano-(3,4-dimethoxy-phenyl)-methyl]-amide.

179. The compound of claim 177, wherein $R^1$ is phenyl, optionally substituted with ethoxy.

180. The compound of claim 179, which is cis-N-(2-{[(R)- and (S)-cyano-(3,4-dimethoxy-phenyl)-methyl]-carbamoyl}-cyclohexyl)-benzamide.

181. The compound of claim 43, wherein $R^5$ is 3-chloro-phenyl.

182. The compound of claim 181, which is cis-(2-{(R)- and (S)-[(3-chloro-phenyl)-cyano-methyl]-carbamoyl}-cyclohexyl)-carbamic acid benzyl ester.

183. The compound of claim 43, wherein $R^5$ is 3-bromo-phenyl.

184. The compound of claim 183, which is trans-(2-{[(3-bromo-phenyl)-cyano-methyl]-carbamoyl}-cyclohexyl)-carbamic acid benzyl ester.

185. The compound of claim 183, which is (2-{[(3-bromo-phenyl)-cyano-methyl]-carbamoyl}-cyclohexyl)-carbamic acid benzyl ester.

186. The compound of claim 183, which is cis-2-(4-ethoxy-phenylamino)-cyclohexanecarboxylic acid [(3-bromo-phenyl)-cyano-methyl]-amide.

187. The compound of claim 43, wherein $R^5$ is 4-bromo-phenyl.

188. The compound of claim 187, which is cis-(2-{(R)- and (S)-[(4-bromo-phenyl)-cyano-methyl]-carbamoyl}-cyclohexyl)-carbamic acid.

189. The compound of claim 43, wherein $R^5$ is benzo[1,3]dioxol-5-yl.

190. The compound of claim 189, which is trans-{2-[(benzo[1,3]dioxol-5-yl-cyano-methyl)-carbamoyl]-cyclohexyl}-carbamic acid benzyl ester.

191. The compound of claim 189, which is cis-{2-[(benzo[1,3]dioxol-5-yl-cyano-methyl)-carbamoyl]-cyclohexyl}-carbamic acid benzyl ester.

192. The compound of claim 189, which is cis-2-(4-ethoxy-phenylamino)-cyclohexanecarboxylic acid (benzo[1,3]dioxol-5-yl-cyano-methyl)-amide.

193. The compound of claims 189, which is cis-2-phenylamino-cyclohexanecarboxylic acid (benzo[1,3]dioxol-5-yl-cyano-methyl)-amide.

194. The compound of claim 22, wherein $R^5$ is hydrogen.

195. The compound of claim 194, wherein $R^1$ is —CO—$R^a$.

196. The compound of claim 195, wherein $R^a$ is cycloalkyl, cycloalkyl-lower-alkyl, cycloalkyloxy, aryl, aryloxy, aryl-lower-alkyl, aryl-lower-alkoxy, aryloxy-lower-alkyl, aryl-S-lower-alkyl, aryl-lower-alkenyl, or heteroaryl-lower-alkoxy.

197. The compound of claim 196, wherein $R^a$ is aryl.

198. The compound of claim 197, which is cis-[2-(cyanomethyl-carbamoyl)-cyclohexyl]-carbamic acid 2-bromo-benzyl ester.

199. The compound of claim 197, which is trans-[4-(cyanomethyl-carbamoyl)-cyclohexyl]-carbamic acid 2-bromo-benzyl ester.

200. The compound of claim 197, wherein $R^a$ is phenyl, optionally substituted with at least one of lower-alkyl, fluorine, -CF₃, -SCH₃, acetylamino, chlorine, bromine, hydroxy, cyano, lower-alkoxy, lower-alkylcarbonyloxy, phenyl, phenoxy, aryl-lower-alkyl or aryl-lower-alkoxy.

201. The compound of claim 200, which is trans-N-[2-(cyanomethyl-carbamoyl)-cyclohexyl]-2-chloro-4-fluoro-benzamide.

202. The compound of claim 200, which is cis-N-[2-(cyanomethyl-carbamoyl)-cyclohexyl]-3-fluoro-4-methyl-benzamide.

203. The compound of claim 200, which is trans-N-[2-(cyanomethyl-carbamoyl)-cyclohexyl]-4-cyanomethyl-benzamide.

204. The compound of claim 200, which is cis-N-[2-(cyanomethyl-carbamoyl)-cyclohexyl]-3,5-ditrifluoromethyl-benzamide.

205. The compound of claim 200, which is cis-N-[2-(cyanomethyl-carbamoyl)-cyclohexyl]-4-tert-butyl-benzamide.

206. The compound of claim 200, which is cis-N-[2-(cyanomethyl-carbamoyl)-cyclohexyl]-3-acetylamino-benzamide.

207. The compound of claim 200, which is trans-N-[2-(cyanomethyl-carbamoyl)-cyclohexyl]-3-acetylamino-benzamide.

208. The compound of claim 200, which is cis-N-[2-(cyanomethyl-carbamoyl)-cyclohexyl]-4-acetylamino-benzamide.

209. The compound of claim 200, which is trans-N-[2-(cyanomethyl-carbamoyl)-cyclohexyl4-acetylamino-benzamide.

210. The compound of claim 200, which is cis-N-[2-(cyanomethyl-carbamoyl)-cyclohexyl]-4-acetyl-benzamide.

211. The compound of claim 200, which is trans-N-[2-(cyanomethyl-carbamoyl)-cyclohexyl]-4-acetyl-benzamide.

212. The compound of claim 200, which is cis-N-[2-(cyanomethyl-carbamoyl)-cyclohexyl]-2-chloro-5-(methylthio)-benzamide.

213. The compound of claim 200, wherein $R^a$ is phenyl, optionally substituted with at least one of hydroxy, methyl, chlorine, bromine or methoxy.

214. The compound of claim 213, which is trans-N-[2-(cyanomethyl-carbamoyl)-cyclohexyl]-2-methoxy-3-methyl-benzamide.

215. The compound of claim 213, which is trans-N-[2-(cyanomethyl-carbamoyl)-cyclohexyl]-2,6-dichloro-4-methoxy-benzamide.

216. The compound of claim 213, which is cis-N-[2-(cyanomethyl-carbamoyl)-cyclohexyl]-3-chloro-4-methyl-benzamide.

217. The compound of claim 213, which is trans-N-[2-(cyanomethyl-carbamoyl)-cyclohexyl]-3-bromo-4-methyl-benzamide.

218. The compound of claim 213, which is cis-N-[2-(cyanomethyl-carbamoyl)-cyclohexyl]-3-chloro-6-methoxy-benzamide.

219. The compound of claim 213, which is trans-N-[2-(cyanomethyl-carbamoyl)-cyclohexyl]-3-chloro-6-methoxy-benzamide.

220. The compound of claim 213, which is cis-N-[2-(cyanomethyl-carbamoyl)-cyclohexyl]-3-chloro-benzamide.

221. The compound of claim 213, which is cis-N-[2-(cyanomethyl-carbamoyl)-cyclohexyl]-2,3-dichloro-benzamide.

222. The compound of claim 213, which is trans-N-[2-(cyanomethyl-carbamoyl)-cyclohexyl]-2,3-dichloro-benzamide.

223. The compound of claim 213, which is cis-N-[2-(cyanomethyl-carbamoyl)-cyclohexyl]-2,4-dichloro-benzamide.

224. The compound of claim 213, which is cis-N-[2-(cyanomethyl-carbamoyl)-cyclohexyl]-2,5-dichloro-benzamide.

225. The compound of claim 213, which is cis-N-[2-(cyanomethyl-carbamoyl)-cyclohexyl]-2,6-dichloro-benzamide.

226. The compound of claim 213, which is cis-N-[2-(cyanomethyl-carbamoyl)-cyclohexyl]-3,4-dichloro-benzamide.

227. The compound of claim 213, which is trans-N-[2-(cyanomethyl-carbamoyl)-cyclohexyl]-3,4-dichloro-benzamide.

228. The compound of claim 213, which is cis-N-[2-(cyanomethyl-carbamoyl)-cyclohexyl]-3,5-dichloro-benzamide.

229. The compound of claim 213, which is trans-N-[2-(cyanomethyl-carbamoyl)-cyclohexyl]-3,5-dichloro-benzamide.

230. The compound of claim 196, wherein $R^a$ is cycloalkyl.

231. The compound of claim 196, wherein $R^a$ is aryl-lower-alkyl.

232. The compound of claim 196, wherein $R^a$ is aryloxy-lower-alkyl.

233. The compound of claim 196, wherein $R^a$ is phenylvinylene, thiophenyl-methylene-oxy, cyclopentyloxy, thiophenyl-ethylene-oxy, naphthyloxy, thiophenyl-trimethylene-oxy, or phenoxy.

234. The compound of claim 233, which is trans-[4-(cyanomethyl-carbamoyl)-cyclohexyl]-carbamic acid phenyl ester.

235. The compound of claim 196, wherein $R^a$ is benzyloxy optionally substituted with at least one group selected from methyl, chloro, fluoro, methoxy, nitro and CF₃.

236. The compound of claim 235, wherein $R^a$ is benzyloxy substituted with methyl.

237. The compound of claim 235, wherein $R^a$ is benzyloxy substituted with chloro.

238. The compound of claim 237, which is cis-[2-(cyanomethyl-carbamoyl)-cyclohexyl]-carbamic acid 2-chloro-benzyl ester.

239. The compound of claim 237, which is cis-[4-(cyanomethyl-carbamoyl)-cyclohexyl]-carbamic acid 4-chloro-benzyl ester.

240. The compound of claim 237, which is cis-[4-(cyanomethyl-carbamoyl)-cyclohexyl]-carbamic acid 3,4-dichloro-benzyl ester.

241. The compound of claim 237, which is cis-[4-(cyanomethyl-carbamoyl)-cyclohexyl]-carbamic acid 3-chloro-benzyl ester.

242. The compound of claim 237, which is trans-[4-(cyanomethyl-carbamoyl)-cyclohexyl]-carbamic acid 2-chloro-benzyl ester.
243. The compound of claim 237, which is trans-[4-(cyanomethyl-carbamoyl)-cyclohexyl]-carbamic acid 3,4-dichloro-benzyl ester.
244. The compound of claim 235, wherein $R^a$ is benzyloxy substituted with fluoro.
245. The compound of claim 235, wherein $R^a$ is benzyloxy substituted with methoxy.
246. The compound of claim 235, wherein $R^a$ is benzyloxy substituted with nitro.
247. The compound of claim 246, which is cis-[2-(cyanomethyl-carbamoyl)-cyclohexyl]-carbamic acid 3-nitro-benzyl ester.
248. The compound of claim 246, which is trans-[4-(cyanomethyl-carbamoyl)-cyclohexyl]-carbamic acid 3-nitro-benzyl ester.
249. The compound of claim 235, wherein $R^a$ is benzyloxy substituted with $CF_3$.
250. The compound of claim 196, wherein $R^a$ is benzyloxy, phenylvinylene, thiophen-2-yl-methylene-oxy, or thiophen-3-yl-methylene-oxy.
251. The compound of claim 250, wherein $R^a$ is benzyloxy.
252. The compound of claim 251, which is trans-[2-(cyanomethyl-carbamoyl)-cyclohexyl]-carbamic acid benzyl ester.
253. The compound of claim 196, wherein $R^a$ is benzyl optionally substituted with chloro, or phenyl optionally substituted with lower-alkyl, lower-alkoxy, or cyano.
254. The compound of claim 253, wherein $R^a$ is 4-ethyl-phenyl, 4-methoxy-phenyl, 4-ethoxy-phenyl, 4-cyano-phenyl, 4-tert.-butyl-phenyl, or 4-chloro-benzyl.
255. The compound of claim 195, wherein $R^a$ is heteroaryl.
256. The compound of claim 255, which is cis-5-methoxy-benzofuran-2-carboxylic acid [2-(cyanomethyl-carbamoyl)-cyclohexyl]-amide.
257. The compound of claim 255, which is trans-5-methoxy-benzofuran-2-carboxylic acid [2-(cyanomethyl-carbamoyl)-cyclohexyl]-amide.
258. The compound of claim 255, wherein $R^a$ is 5-methoxy-benzofuran-2-yl.
259. The compound of claim 194, wherein $R^1$ is —$SO_2$—$R^b$.
260. The compound of claim 194, wherein $R^1$ is phenyl, optionally substituted with ethoxy.
261. The compound of claim 22, wherein $R^5$ is cycloalkyl.
262. The compound of claim 261, wherein $R^5$ is cyclopropyl.
263. The compound of claim 262, wherein $R^1$ is —CO—$R^a$.
264. The compound of claim 263, wherein $R^a$ is cycloalkyl, cycloalkyl-lower-alkyl, cycloalkyloxy, aryl, aryloxy, aryl-lower-alkyl, aryl-lower-alkoxy, aryloxy-lower-alkyl, aryl-S-lower-alkyl, aryl-lower-alkenyl, or heteroaryl-lower-alkoxy.
265. The compound of claim 264, wherein $R^a$ cycloalkyl.
266. The compound of claim 264, wherein $R^a$ is aryl-lower-alkyl.
267. The compound of claim 266, which is cis-N-[cyano (cyclopropyl)methyl]-2-{[3-(3-methoxyphenyl) propanoyl] amino}cyclohexanecarboxamide.
268. The compound of claim 264, wherein $R^a$ is aryloxy-lower-alkyl.
269. The compound of claim 264, wherein $R^a$ is phenyl optionally substituted with at least one group selected from phenyl, cyano, and fluoro; or $R^a$ is benzyloxy optionally substituted with at least one group selected from methyl, chloro, fluoro, methoxy, nitro, and $CF_3$; or $R^a$ is phenylvinylene, thiophenyl-methylene-oxy, cyclopentyloxy, thiophenyl-ethylene-oxy, naphthyloxy, thiophenyl-trimethylene-oxy, or phenoxy.
270. The compound of claim 269, which is cis-N-[2-({[cyano(cyclopropyl)methyl]-amino}carbonyl)cyclohexyl]-3,4-difluorobenzamide.
271. The compound of claim 269, wherein $R^a$ is benzyloxy, phenylvinylene, thiophen-2-yl-methylene-oxy, or thiophen-3-yl-methylene-oxy.
272. The compound of claim 271, wherein $R^a$ is benzyloxy.
273. The compound of claim 272, which is cis{2-[(cyano-cyclopropyl-methyl)-carbamoyl]-cyclohexyl}-carbamic acid benzyl ester.
274. The compound of claim 264, wherein $R^a$ is benzyl optionally substituted with chloro, or phenyl optionally substituted with lower-alkyl, lower-alkoxy, or cyano.
275. The compound of claim 274, which is cis-2-{[(4-chlorophenyl)acetyl]amino}-N-[cyano(cyclopropyl)methyl]cyclo-hexanecarboxamide.
276. The compound of claim 274, which is cis-N-[2-({[cyano(cyclopropyl)methyl]amino}carbonyl)cyclohexyl]-3,4,5-trimethoxybenzamide.
277. The compound of claim 274, wherein $R^a$ is 4-ethyl-phenyl, 4-methoxy-phenyl, 4-ethoxy-phenyl, 4-cyano-phenyl, 4-tert.-butyl-phenyl, or 4-chloro-benzyl.
278. The compound of claim 277, which is cis-N-[2-({[cyano(cyclopropyl)methyl]amino}carbonyl)cyclohexyl]-4-ethylbenzamide.
279. The compound of claim 277, which is cis-N-[2-({[cyano(cyclopropyl)methyl]amino}carbonyl)cyclohexyl]-4-ethoxybenzamide.
280. The compound of claim 277, which is cis-N-[2-({[cyano(cyclopropyl)methyl]amino}carbonyl)cyclohexyl]-4-methoxybenzamide.
281. The compound of claim 277, which is trans-N-[2-({[cyano(cyclopropyl)-methyl]amino}carbonyl)cyclohexyl]-4-methoxybenzamide.
282. The compound of claim 277, which is trans-N-[2-({[cyano(cyclopropyl)methyl]amino}carbonyl)cyclohexyl]-4-ethylbenzamide.
283. The compound of claim 277, which is cis-N-[2-({[cyano(cyclopropyl)methyl]amino}carbonyl)cyclohexyl]-4-tert-butylbenzamide.
284. The compound of claim 277, which is cis-N-[2-({[cyano(cyclopropyl)methyl]amino}carbonyl)cyclohexyl]-4-cyanobenzamide.
285. The compound of claim 263, wherein $R^a$ is heteroaryl.
286. The compound of claim 285, wherein $R^a$ is 5-methoxy-benzofuran-2-yl.
287. The compound of claim 262, wherein $R^1$ is —$SO_2$—$R^b$.
288. The compound of claim 262, wherein $R^1$ is phenyl, optionally substituted with ethoxy.
289. An isolated stereoisomer selected from the group consisting of compounds of formula (Ia)

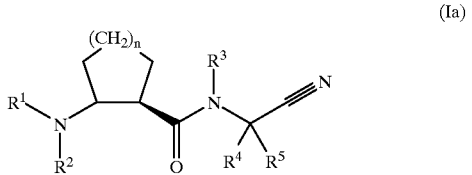

(Ia)

wherein
  $R^1$ is hydrogen, aryl, —CO—$R^a$ or —$SO_2$—$R^b$, wherein
    $R^a$ represents lower-alkyl, lower-alkoxy, cycloalkyl, cycloalkyl-lower-alkyl, cycloalkyl-lower-alkoxy, cycloalkyloxy, aryl, aryloxy, aryl-lower-alkyl, aryl-lower-alkoxy, aryloxy-lower-alkyl, aryl-S-lower-alkyl, aryl-lower-alkenyl, heteroaryl, heteroaryl-lower-alkyl, or heteroaryl-lower-alkoxy, and $R^b$ represents aryl, aryl-lower-alkyl, or heteroaryl, $R^2$ is hydrogen or lower-alkyl, $R^3$ is hydrogen or lower-alkyl, $R^4$ is hydrogen or lower-alkyl, $R^5$ is hydrogen, lower-alkyl, cycloalkyl, or aryl, and n is 1 or 2;

pharmaceutically acceptable salts of compounds of formula (Ia); and pharmaceutically acceptable esters of compounds of formula (Ia).

290. An isolated stereoisomer selected from the group consisting of compounds of formula (Ib)

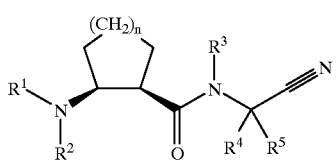

(Ib)

wherein $R^1$ is hydrogen, aryl, —CO—$R^a$ or —SO$_2$—$R^b$, wherein $R^a$ represents lower-alkyl, lower-alkoxy, cycloalkyl, cycloalkyl-lower-alkyl, cycloalkyl-lower-alkoxy, cycloalkyloxy, aryl, aryloxy, aryl-lower-alkyl, aryl-lower-alkoxy, aryloxy-lower-alkyl, aryl-S-lower-alkyl, aryl-lower-alkenyl, heteroaryl, heteroaryl-lower-alkyl, or heteroaryl-lower-alkoxy, and $R^b$ represents aryl, aryl-lower-alkyl, or heteroaryl, $R^2$ is hydrogen or lower-alkyl, $R^3$ is hydrogen or lower-alkyl, $R^4$ is hydrogen or lower-alkyl, $R^5$ is hydrogen, lower-alkyl, cycloalkyl, or aryl, and n is 1 or 2;

pharmaceutically acceptable salts of compounds of formula (Ib); and pharmaceutically acceptable esters of compounds of formula (Ib).

291. An isolated stereoisomer selected from the group consisting of compounds of formula (Ic)

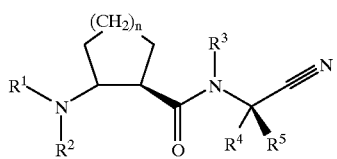

(Ic)

wherein $R^1$ is hydrogen, aryl, —CO—$R^a$ or —SO$_2$—$R^b$, wherein $R^a$ represents lower-alkyl, lower-alkoxy, cycloalkyl, cycloalkyl-lower-alkyl, cycloalkyl-lower-alkoxy, cycloalkyloxy, aryl, aryloxy, aryl-lower-alkyl, aryl-lower-alkoxy, aryloxy-lower-alkyl, aryl-S-lower-alkyl, aryl-lower-alkenyl, heteroaryl, heteroaryl-lower-alkyl, or heteroaryl-lower-alkoxy, and $R^b$ represents aryl, aryl-lower-alkyl, or heteroaryl, $R^2$ is hydrogen or lower-alkyl, $R^3$ is hydrogen or lower-alkyl, $R^4$ is hydrogen or lower-alkyl, $R^5$ is hydrogen, lower-alkyl, cycloalkyl, or aryl, and n is 1 or 2;

pharmaceutically acceptable salts of compounds of formula (Ic); and pharmaceutically acceptable esters of compounds of formula (Ic).

292. A process for the manufacture of compounds compounds of formula (I)

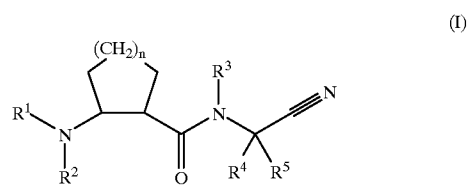

(I)

wherein $R^1$ is hydrogen, aryl, —CO—$R^a$ or —SO$_2$—$R^b$, wherein $R^a$ represents lower-alkyl, lower-alkoxy, cycloalkyl, cycloalkyl-lower-alkyl, cycloalkyl-lower-alkoxy, cycloalkyloxy, aryl, aryloxy, aryl-lower-alkyl, aryl-lower-alkoxy, aryloxy-lower-alkyl, aryl-S-lower-alkyl, aryl-lower-alkenyl, heteroaryl, heteroaryl-lower-alkyl, or heteroaryl-lower-alkoxy, and $R^b$ represents aryl, aryl-lower-alkyl, or heteroaryl, $R^2$ is hydrogen or lower-alkyl, $R^3$ is hydrogen or lower-alkyl, $R^4$ is hydrogen or lower-alkyl, $R^5$ is hydrogen, lower-alkyl, cycloalkyl, or aryl, and n is 1 or 2;

the process comprising:

reacting a compound of formula (II)

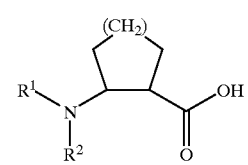

(II)

wherein $R^1$ is hydrogen, aryl, —CO—$R^a$ or —SO$_2$—$R^b$, wherein $R^a$ represents lower-alkyl, lower-alkoxy, cycloalkyl, cycloalkyl-lower-alkyl, cycloalkyl-lower-alkoxy, cycloalkyloxy, aryl, aryloxy, aryl-lower-alkyl, aryl-lower-alkoxy, aryloxy-lower-alkyl, aryl-S-lower-alkyl, aryl-lower-alkenyl, heteroaryl, heteroaryl-lower-alkyl, or heteroaryl-lower-alkoxy, and $R^b$ represents aryl, aryl-lower-alkyl, or heteroaryl, $R^2$ is hydrogen or lower-alkyl, and n is 1 or 2;

with a compound of formula (III)

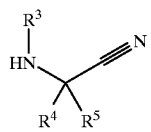
(III)

wherein
R³ is hydrogen or lower-alkyl,
R⁴ is hydrogen or lower-alkyl, and
R⁵ is hydrogen, lower-alkyl, cycloalkyl, or aryl;
to form the compound of formula (I).

293. A process for the manufacture of compounds compounds of formula (I)

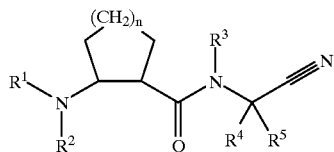
(I)

wherein
R¹ is hydrogen, aryl, —CO—Rᵃ or —SO₂—Rᵇ, wherein
  Rᵃ represents lower-alkyl, lower- alkoxy, cycloalkyl, cycloalkyl-lower-alkyl, cycloalkyl-lower-alkoxy, cycloalkyloxy, aryl, aryloxy, aryl-lower-alkyl, aryl-lower-alkoxy, aryloxy-lower-alkyl, aryl-S-lower-alkyl, aryl-lower-alkenyl, heteroaryl, heteroaryl-lower-alkyl, or heteroaryl-lower-alkoxy, and
  Rᵇ represents aryl, aryl-lower-alkyl, or heteroaryl,
R² is hydrogen or lower-alkyl,
R³ is hydrogen or lower-alkyl,
R⁴ is hydrogen or lower-alkyl,
R⁵ is hydrogen, lower-alkyl, cycloalkyl, or aryl, and
n is 1 or 2;

the process comprising:
reacting a compound of formula (IV)

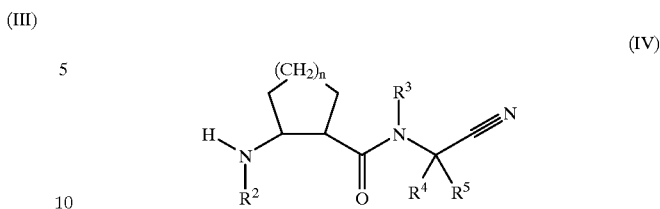
(IV)

wherein
R² is hydrogen or lower-alkyl,
R³ is hydrogen or lower-alkyl,
R⁴ is hydrogen or lower-alkyl,
R⁵ is hydrogen, lower-alkyl, cycloalkyl, or aryl, and
n is 1 or 2;
with a compound of formula (V) or (VI)

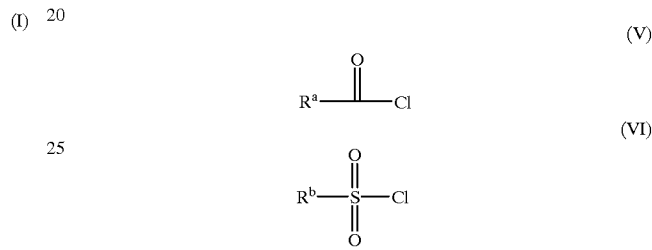

wherein
  Rᵃ represents lower-alkyl, lower-alkoxy, cycloalkyl, cycloalkyl-lower-alkyl, cycloalkyl-lower-alkoxy, cycloalkyloxy, aryl, aryloxy, aryl-lower-alkyl, aryl-lower-alkoxy, aryloxy-lower-alkyl, aryl-S-lower-alkyl, aryl-lower-alkenyl, heteroaryl, heteroaryl-lower-alkyl, or heteroaryl-lower-alkoxy, and
  Rᵇ represents aryl, aryl-lower-alkyl, or heteroaryl,
to form the compound of formula (I).

294. A method for treatment of a human or animal having osteoporosis, instable angina pectoris and/or plaque rupture, comprising administering a therapeutically effective amound of the compound of claim 1 to the human or animal.

* * * * *

UNITED STATES PATENT AND TRADEMARK OFFICE
CERTIFICATE OF CORRECTION

PATENT NO. : 6,462,076 B2
DATED : October 8, 2002
INVENTOR(S) : Tobias Gabriel, Michael Pech and Rosa Maria Rodriguez Sarmiento It is certified that error appears in the above-identified patent and that said Letters Patent is hereby corrected as shown below:

<u>Title page,</u>
Item [30], Foreign Application Priority Data, reads "Jun. 14, 2000 (EP)..........112577" it should read -- Jun. 14, 2000 (EP)..........00112577 --.

<u>Column 49,</u>
Line 36, "benzyll" should read -- benzyl --.

<u>Column 53,</u>
Line 15, "(R)-" should read -- [(R)- --.

<u>Column 55,</u>
Line 48, "cyclohexyl4-" should read -- cyclohexyl]-4- --.

<u>Column 60,</u>
Lines 46-54, formula II reads

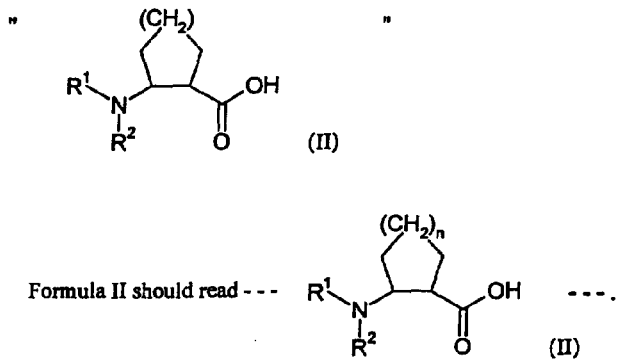

Formula II should read ---

UNITED STATES PATENT AND TRADEMARK OFFICE
CERTIFICATE OF CORRECTION

PATENT NO.    : 6,462,076 B2
DATED         : October 8, 2002
INVENTOR(S)   : Tobias Gabriel, Michael Pech and Rosa Maria Rodriguez Sarmiento It is certified that error appears in the above-identified patent and that said Letters Patent is hereby corrected as shown below:

Column 62,
Line 43, "amound" should read -- amount --.

Signed and Sealed this

Eleventh Day of February, 2003

JAMES E. ROGAN
*Director of the United States Patent and Trademark Office*